US009498787B2

(12) United States Patent
Fenton et al.

(10) Patent No.: US 9,498,787 B2
(45) Date of Patent: Nov. 22, 2016

(54) FIRE PROTECTION APPARATUS, SYSTEMS AND METHODS FOR ADDRESSING A FIRE WITH A MIST

(75) Inventors: Marcus Brian Mayhall Fenton, Cambridgeshire (GB); James Oliver French, Cambridgeshire (GB); Zachary L. Magnone, Cumberland, RI (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 1495 days.

(21) Appl. No.: 12/742,046

(22) PCT Filed: Nov. 7, 2008

(86) PCT No.: PCT/US2008/012571
§ 371 (c)(1),
(2), (4) Date: Apr. 22, 2011

(87) PCT Pub. No.: WO2009/061471
PCT Pub. Date: May 14, 2009

(65) Prior Publication Data
US 2011/0203813 A1  Aug. 25, 2011

Related U.S. Application Data

(60) Provisional application No. 60/987,021, filed on Nov. 9, 2007, provisional application No. 60/989,083, filed on Nov. 19, 2007.

(30) Foreign Application Priority Data

Mar. 3, 2008  (GB) .................................. 0803959.6

(51) Int. Cl.
*B05B 7/06* (2006.01)
*A61L 2/22* (2006.01)
(Continued)

(52) U.S. Cl.
CPC ................. *B05B 7/065* (2013.01); *A61L 2/22* (2013.01); *A62C 5/008* (2013.01); *A62C 31/05* (2013.01);
(Continued)

(58) Field of Classification Search
CPC ... B05B 7/0475; B05B 7/0466; B05B 7/067; B05B 7/065; B05B 7/0433; A62C 31/07; A62C 31/05; A62C 5/008; A62C 35/023; A62C 99/0072; A61L 2202/25; A61L 2/22
USPC ......... 239/433, 10, 398, 418, 421, 423, 424, 239/424.5, 425, 434.5
See application file for complete search history.

(56) References Cited

U.S. PATENT DOCUMENTS 1,779,680 A * 10/1930 Rayfield ....................... 239/425
2,990,885 A *  7/1961 Brazier .......................... 169/44
(Continued)

FOREIGN PATENT DOCUMENTS

CN      1211703 A      3/1999
FR      2 120 393      8/1972
(Continued)

OTHER PUBLICATIONS

International Searching Authority, International Search Report and Written Opinion issued in International Application No. PCT/GB2008/012571, Jan. 9, 2009, 24 pages.
(Continued)

*Primary Examiner* — Arthur O Hall
*Assistant Examiner* — Viet Le
(74) *Attorney, Agent, or Firm* — Perkins Coie LLP

(57) ABSTRACT

Fire protection apparatus, systems, and methods for addressing a fire with a mist are provided. More particularly, the invention provides systems and their method of design which provide a water mist to address and preferably suppress a fire. The invention further provides systems and methods for total flooding volume protection of a space to address a fire, preferably control, suppress, and more preferably extinguish a fire. The invention further provides atomizing devices for use in such systems and methods.

44 Claims, 25 Drawing Sheets

(51) Int. Cl.
*A62C 5/00* (2006.01)
*A62C 31/05* (2006.01)
*A62C 31/07* (2006.01)
*A62C 35/02* (2006.01)
*A62C 99/00* (2010.01)
*B05B 7/04* (2006.01)

(52) U.S. Cl.
CPC ............ *A62C 31/07* (2013.01); *A62C 35/023* (2013.01); *A62C 99/0072* (2013.01); *B05B 7/0433* (2013.01); *B05B 7/067* (2013.01); *A61L 2202/25* (2013.01); *B05B 7/0466* (2013.01); *B05B 7/0475* (2013.01); *Y10T 29/49401* (2015.01)

(56) References Cited

U.S. PATENT DOCUMENTS

| | | | |
|---|---|---|---|
| 3,073,534 A | | 1/1963 | Hampshire |
| 3,684,188 A | | 8/1972 | Miller et al. |
| 4,314,670 A | | 2/1982 | Walsh, Jr. |
| 4,337,618 A | * | 7/1982 | Hughes et al. ............... 60/39.55 |
| 4,634,054 A | * | 1/1987 | Grusha ........................ 239/423 |
| 4,646,848 A | | 3/1987 | Bruensicke |
| 4,903,895 A | | 2/1990 | Mathewson et al. |
| RE33,464 E | | 11/1990 | Gitman |
| 5,176,324 A | | 1/1993 | Furuse et al. |
| 5,462,229 A | | 10/1995 | Tanaka et al. |
| 5,899,387 A | | 5/1999 | Haruch |
| 6,378,787 B1 | | 4/2002 | Buchi et al. |
| 6,405,944 B1 | | 6/2002 | Benalikhoudja |
| 6,662,549 B2 | | 12/2003 | Burns |
| 6,899,184 B2 | | 5/2005 | Reynolds |
| 7,967,221 B2 | | 6/2011 | Snyder et al. |
| 2006/0102749 A1 | * | 5/2006 | Crabtree et al. ............. 239/410 |
| 2007/0210186 A1 | | 9/2007 | Fenton et al. |
| 2008/0230632 A1 | | 9/2008 | Fenton et al. |
| 2009/0314500 A1 | | 12/2009 | Fenton et al. |
| 2010/0230119 A1 | | 9/2010 | Worthy et al. |
| 2010/0230516 A1 | * | 9/2010 | Solie et al. .................. 239/428 |
| 2010/0301129 A1 | | 12/2010 | Fenton et al. |
| 2011/0127347 A1 | | 6/2011 | Worthy et al. |
| 2012/0018531 A1 | | 1/2012 | Fenton et al. |

FOREIGN PATENT DOCUMENTS

| | | |
|---|---|---|
| GB | 1 320 016 A | 6/1973 |
| GB | 1475771 | 6/1977 |
| WO | WO 94/08724 A | 4/1994 |
| WO | WO 01/76764 A | 10/2001 |
| WO | WO 03/072952 A | 9/2003 |
| WO | WO 2005/082546 A | 9/2005 |

OTHER PUBLICATIONS

International Searching Authority, International Preliminary Report on Patentability issued in International Application No. PCT/GB2008/012571, May 11, 2010, 24 pages.
European Application No. 08846644, Mar. 26, 2014 from the EPO Patent Register.
First Office Action (w/English translation) issued in related co-pending Chinese Application No. 200880115456.5, Nov. 28, 2011, 10 pages.
Second Office Action (w/English translation issued in related co-pending Chinese Application No. 200880115456.5, Jun. 18, 2012, 7 pages.
Official Notification on the Merits (w/English translation) issued in related co-pending Israeli Application No. 205631, Oct. 10, 2012, 4 pages.
Substantive Examination Examiner's Report issued in related co-pending Malaysian Application No. PI2010002147, May 29, 2013, 2 pages.
Examiner's Report issued in related co-pending New Zealand Application No. 585365, Jul. 3, 2012, 2 pages.
Examination Report issued in related co-pending Australian Application No. 2008325164, Feb. 5, 2013, 3 pages.
Examination Report issued in related co-pending Gulf Cooperation Council Application No. GCC/P/2008/12115, Jan. 7, 2014, 10 pages.
Technical Report issued in related co-oending Peruvian Application No. 001907-2008/DIN, Jun. 19, 2013, 10 pages.
First Office Action (w/English translation) issued in related co-pending Chilean Patent Application No. 3342-2008, Nov. 8, 2010, 7 pages.
AU Patent Office for related co-pending Australian Application No. 2008325164, Aug. 13, 2014, 481 pages.
Response to substantive Examination Examiner's Report issued in related co-pending Malaysian Application No. PI2010002147, Dec. 13, 2013, 19 pages.
International Searching Authority, International Search Report and Written Opinion issued in International Application No. PCT/GB2008/51042, Mar. 5, 2009, 8 pages.
International Searching Authority, International Preliminary Report on Patentability issued in Internation Application No. PCT/GB2008/51042, May 11, 2010, 6 pages.
Co-pending related U.S. Appl. No. 12/741,941, filed Aug. 17, 2010.
European Application No. 08848325.0, Nov. 26, 2013 from EPO Patent Register.

* cited by examiner

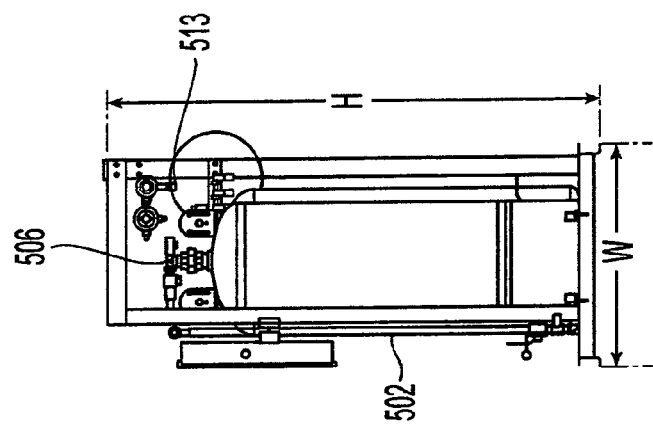
Fig. 7
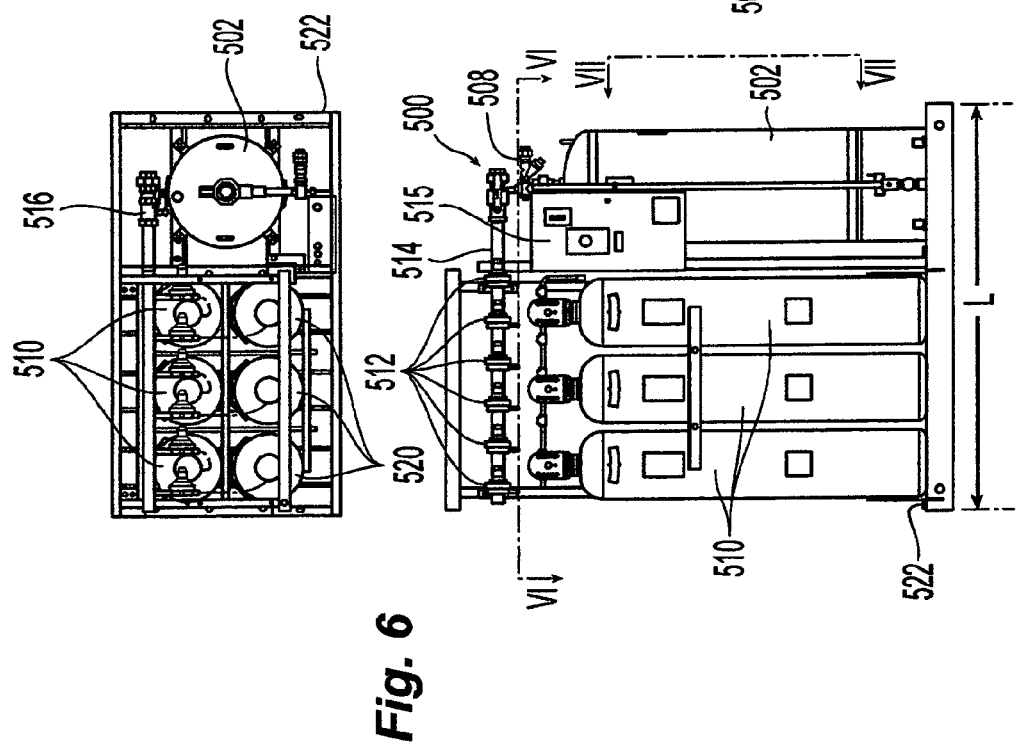
Fig. 6
Fig. 5

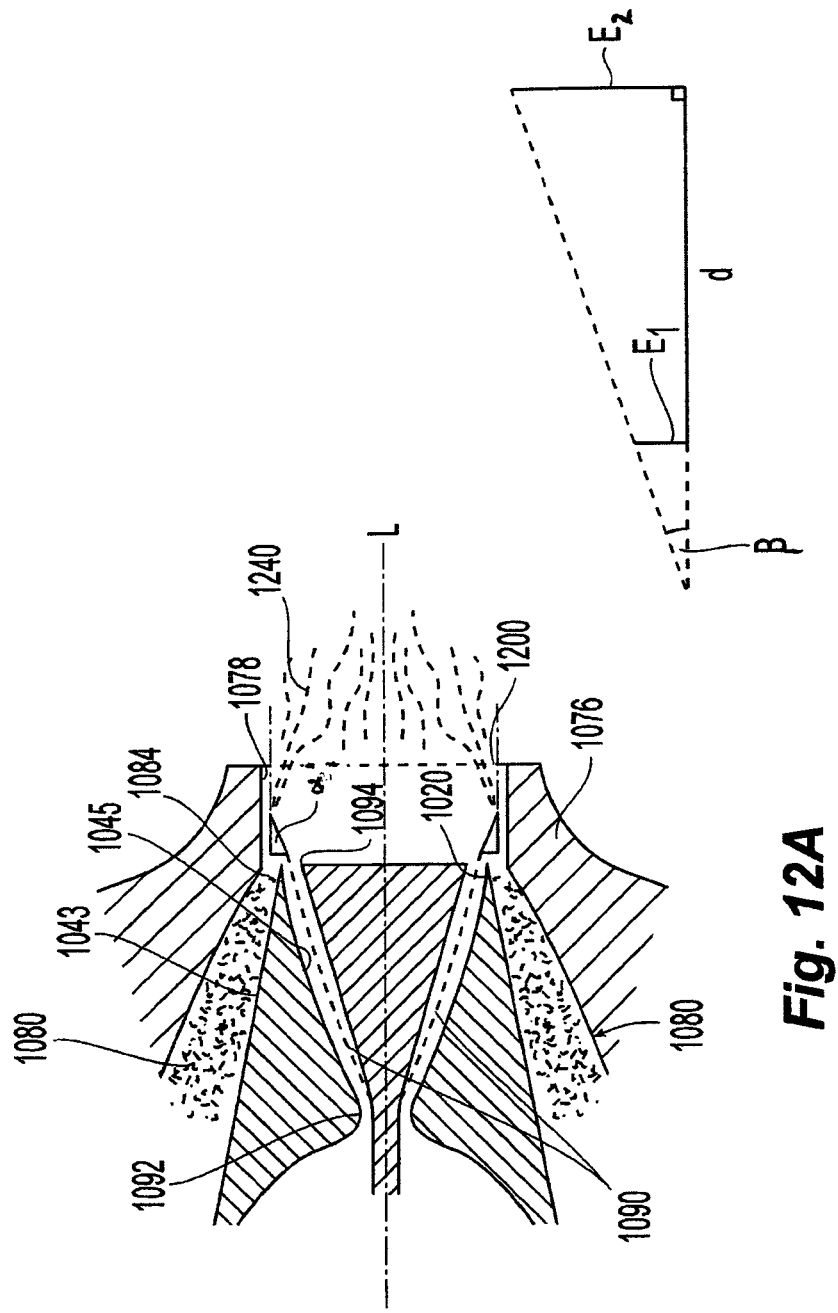

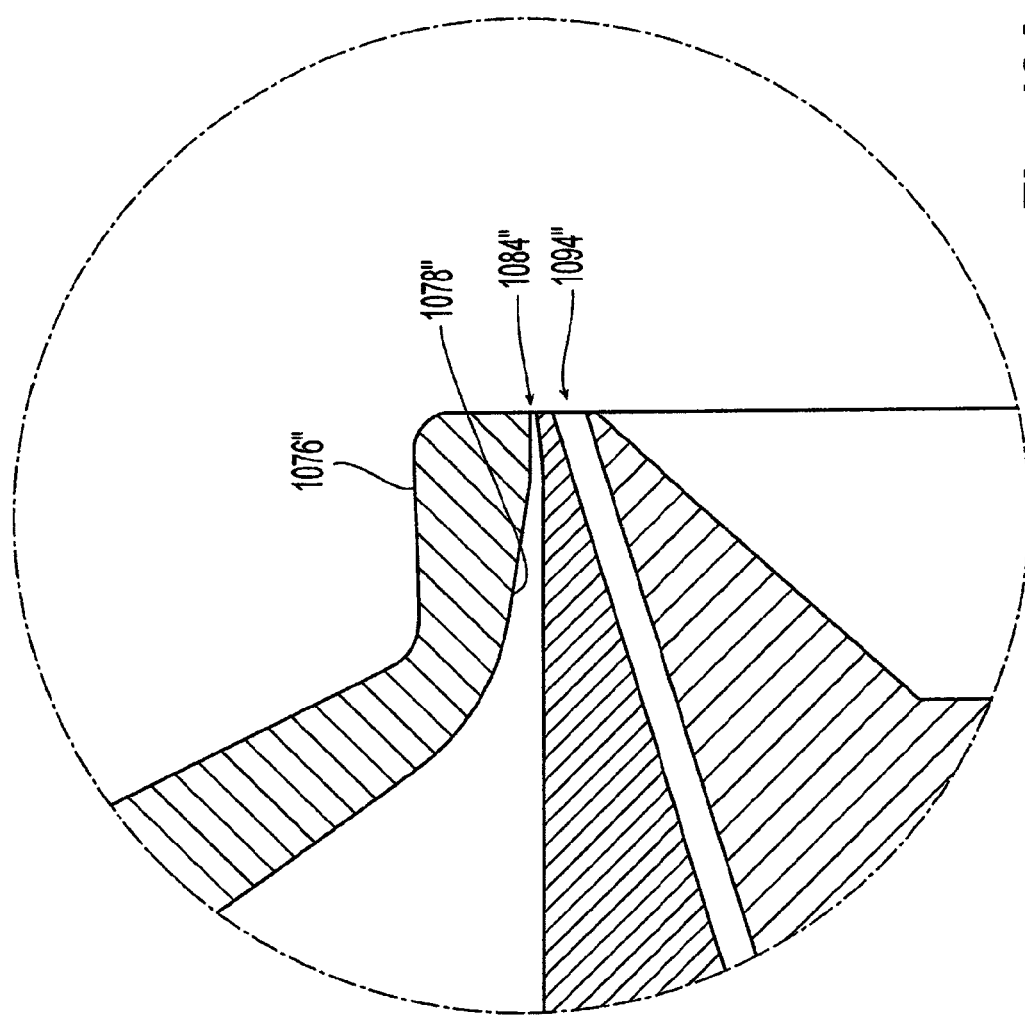

FIRE PROTECTION APPARATUS, SYSTEMS AND METHODS FOR ADDRESSING A FIRE WITH A MIST

PRIORITY DATA AND INCORPORATION BY REFERENCE

This application is a U.S. National Stage Application of International Application No. PCT/US2008/012571, which was filed on Nov. 7, 2008, and which claims priority to U.S. Provisional Application No. 60/987,021, which was filed on Nov. 9, 2007, U.S. Provisional Application No. 60/989,083, which was filed on Nov. 19, 2007, and Great Britain Application No. 0803959.6, which was filed on Mar. 3, 2008, all of which are incorporated by reference in their entireties as if recited in full herein.

TECHNICAL FIELD

This invention relates generally to liquid mist spray systems and methods for fire protection. More specifically, the invention is directed to systems and their method of design which provide a water mist to address and preferably suppress a fire. Even more preferably, the invention relates to systems and methods for total flooding volume protection of a space to address a fire, preferably control, suppress, and more preferably extinguish a fire. The invention further provides devices for use in the systems and methods.

BACKGROUND OF THE INVENTION

Known high pressure water mist systems, such as for example, HI-FOG® by MARIOFF CORPORATION rely on the production of water droplets, ranging between 50 μm-120 μm (microns), in which larger droplets entrain smaller droplets into the critical combustion region of a fire. Providing a desired mix of droplet sizes in the protected area using such as high pressure system requires careful location of the discharge points and a large quantity of water. The HI-FOG® system is a single fluid (water) system in which the fluid is delivered to the discharging nozzles at a high pressure for the 50 μm-120 μm droplet generation.

One type of device for use in such a system is described in WO 92/20453. Shown and described therein is a spray head arranged with a number of nozzles arranged close to each other for a continuous directional fog spray.

Another water mist system and method is described in U.S. Patent Publication No. 20050000700. Therein is described a fire extinguishing method for high spaces such as engine rooms of ships in which a mist is provided in an unevenly distributed manner so that a circulating motion of the mist is created in the space.

Twin or dual fluid fire protection nozzles are shown and described in U.S. Pat. No. 5,312,041 and U.S. Pat. No. 5,520,331. In U.S. Pat. No. 5,312,041, shown and described is a dual fluid method and apparatus for extinguishing fires in which a nozzle discharges a first fluid in a path surrounded by a second fluid. In U.S. Pat. No. 5,520,331, shown and described is a convergent/divergent gas nozzle that atomizes a liquid provided through a liquid delivery tube having an aperture centered within a central gas conduit of an upstream mixing block connected to the nozzle.

Other water mist systems and nozzles are described in International Patent Application Publication Nos. WO 2003/030995; WO 2005/115555 and International Patent Application Publication No. WO 2006/132557 and U.S. Pat. No. 7,080,793. Other Mist generating devices are shown and described in International Patent Publication No. WO 2005/082545 and International Patent Publication No. WO 2005/082546, each of which is assigned to Pursuit Dynamics PLC, a named applicant in the instant application (outside of the U.S.).

WO 2001/76764 shows a mist generating apparatus which uses two fluids, primarily for use in fire suppression. In WO 2001/76764, a spray of first fluid droplets is created by forcing the first fluid through a number of aerosol nozzles in a conventional manner. The droplets are then carried by a stream of a second fluid through a convergent-divergent nozzle which sprays the combined stream of first fluid droplets and second fluid from the apparatus. The purpose of WO 2001/76764 is to reduce the pressure required to create the aerosol spray of the first fluid by using the second stream of fluid to carry the first fluid droplets out of the apparatus. The second stream also reduces frictional forces which can in some cases cause the first fluid droplets forming the aerosol spray to evaporate.

WO 2001/76764 does not use the second fluid in order to create the first fluid droplet regime. Instead, the droplets are created via an array of aerosol nozzles which create the droplets in a conventional manner. The stream of second fluid then carries the droplets through the spray nozzle without any atomization mechanism being applied to the first fluid by the second fluid. Thus, WO 2001/76764 still requires the first fluid to be supplied at relatively high pressure in order to create the aerosol droplets.

DISCLOSURE OF INVENTION

Installation Methods

One embodiment of the invention is a method of mist fire protection for fixed equipment within a substantially enclosed space having a ceiling, a plurality of walls so as to define a plurality of corners and an enclosure volume of at least 130 cu. m. (4590 cu. ft.). This method includes disposing at least one mist generating device in the substantially enclosed space, the disposing at least one mist generating device may be selected from (i) mounting at least two mist generating devices in the enclosed space, wherein the at least 130 cu. m. (4590 cu. ft.) (4590 cu. ft.) is at least 260 cu. m. (9180 cu. ft.), the at least two mist generating devices being disposed in diagonally opposed corners so as to define a minimum spacing therebetween of about 3.4 m. (11 ft.), (ii) mounting the at least one mist generating device in a pendent configuration where the enclosure height ranges between about 3.0 m. (9.8 ft.) to about 8.0 m. (26.2 ft.) with a clearance from any wall of the enclosed space ranging from 0.3 m. (1 ft.) to about 3.4 m. (11 ft.), (iii) mounting the at least one mist generating device in a sidewall configuration where the enclosure height ranges between about 1.0 m. (3.3 ft.) to about 8.0 m. (26.2 ft.), the mounting being beneath the ceiling at a distance from the ceiling ranging from about 1.0 m. (3.3 ft.) to about one half the enclosure height and with a clearance of at least 1.0 m. (3.3 ft.) from any of the plurality of corners of the enclosed space, (iv) mounting at least two mist generating devices in a pendent configuration where the enclosure height ranges between about 3.0 m. (9.8 ft.) to about 8.0 m. (26.2 ft.) with a clearance from any of the plurality of walls of the enclosed space ranging from 0.3 m. (1 ft.) to about 3.4 m. (11 ft.) and spaced from one another by a distance ranging from about 3.4 m. (11 ft.) to about 30.4 ft; and (v) mounting at least two mist generating devices in a sidewall configuration where the sidewall enclosure height ranges between about 1.0 m.

(3.3 ft.) to about 8.0 m. (26.2 ft.) beneath the ceiling at a distance from the ceiling ranging from about 1.0 m. (3.3 ft.) to about one half the ceiling enclosure height and with a clearance of at least 1.0 m. (3.3 ft.) from any of the plurality of corners of the enclosed space such that the at least two mist generating devices each define a center line of discharge having an unobstructed discharge path with a diameter of about 1.5 m. (5 ft.) from the device to an opposing wall of the plurality of walls, the device being mounted from the opposing wall at a distance ranging between about 3.8 m. (12.5 ft.) to about 12.0 m. (39.3 ft.) with the center lines of discharge of the at least two devices having a perpendicular spacing ranging between about 1.0 m. (3.3 ft.) to about 4.6 m. (15 ft.).

The method further includes piping a self-contained fluid supply source to the mist generating device. The piping may include coupling an outlet of a liquid supply tank having a capacity of at least 25 gallons to the mist generating device. The piping may also include coupling in parallel a gas supply having a bank of at least three pressurized 11.3 cu. m. (400 cu. ft.) tanks with the liquid supply tank and the mist generating device.

The method further includes interlocking an actuator to release the gas from the cylinders to the tank and the at least one mist generating device. The interlocking may include coupling the actuator with a heat release detector disposed in the enclosed space, the heat detector being responsive to a fire in the enclosed space such that upon detection of a fire, the heat detector signals the actuator to release the gas from the cylinders to pressurize the tank and to deliver the gas to the mist generating device.

In another embodiment, the invention is a kit to provide mist fire protection for fixed equipment within a substantially enclosed space having a ceiling, a plurality of walls so as to define a plurality of corners and an enclosure volume of at least 130 cu. m. (4590 cu. ft.). The kit comprises at least one mist generating device selected from (i) at least two mist generating devices to be mounted in the enclosed space, wherein the at least 130 cu. m. (4590 cu. ft.) is at least 260 cu. m. (9180 cu. ft.), the at least two mist generating devices to be disposed in diagonally opposed corners so as to define a minimum spacing therebetween of about 3.4 m. (11 ft.), (ii) at least one mist generating device to be mounted in a pendent configuration in the enclosed space where the enclosure height ranges between about 3.0 m. (9.8 ft.) to about 5.0 m. (16.4 ft.) with a clearance from any wall of the enclosed space ranging from 0.3 m. (1 ft.) to about 3.4 m. (11 ft.), (iii) at least one mist generating device to be mounted in a sidewall configuration in the enclosed space where the enclosure height ranges between about 1.0 m. (3.3 ft.) to about 5.0 m. (16.4 ft.), the at least one mist generating device to be mounted being beneath the ceiling at a distance from the ceiling ranging from about 1.0 m. (3.3 ft.) to about one half the enclosure height and with a clearance of at least 1.0 m. (3.3 ft.) from any of the plurality of corners of the enclosed space, (iv) at least two mist generating devices to be mounted in a pendent configuration in the enclosed space where the enclosure height ranges between about 3.0 m. (9.8 ft.) to about 5.0 m. (16.4 ft.) with a clearance from any of the plurality of walls of the enclosed space ranging from 0.3 m. (1 ft.) to about 3.4 m. (11 ft.) and spaced from one another by a distance ranging from about 3.4 m. (11 ft.) to about 30.4 ft; and (v) at least two mist generating devices to be mounted in a sidewall configuration in the enclosed space where the sidewall enclosure height ranges between about 1.0 m. (3.3 ft.) to about 5.0 m. (16.4 ft.) beneath the ceiling at a distance from the ceiling ranging from about 1.0 m. (3.3 ft.) to about one half the ceiling enclosure height and with a clearance of at least 1.0 m. (3.3 ft.) from any of the plurality of corners of the enclosed space such that the at least two mist generating devices each define a center line of discharge having an unobstructed discharge path with a diameter of about 1.5 m. (5 ft.) from the device to an opposing wall of the plurality of walls, the device being mounted from the opposing wall at a distance ranging between about 3.8 m. (12.5 ft.) to about 12.0 m. (39.3 ft.) with the center lines of discharge of the at least two devices having a perpendicular spacing ranging between about 1.0 m. (3.3 ft.) to about 4.6 m. (15 ft.).

The kit further comprises a self-contained fluid supply source. The self-contained fluid supply source includes a liquid supply tank having a capacity of about 25 gallons and a gas supply including a bank of at least three (3) 11.3 cu. m. (400 cu. ft.) nitrogen gas cylinders coupled to a manifold having an outlet for connection to the at least one atomizer. The manifold is connected to the liquid supply tank to pressurize the tank. The tank includes an outlet for connection to the at least one mist generating device. The kit further includes an orifice for locating in-line between the outlet of the tank and the at least one atomizer to provide a substantially constant flow of the liquid from the tank to the at least one mist generating device.

Fire Protection Systems

The present invention also provides a mist fire protection system for a substantially enclosed space of any volume, such as, e.g., a space having a volume of at least one hundred thirty cubic meters (130 cu. m.) or four thousand five hundred and ninety cubic feet (4590 cu. ft), including at least 260 cu. m., such as e.g., 1040 cu. m. The system includes at least one mist generating device coupled to a fluid supply source to deliver to the at least one device, a first fluid and a second fluid for generation of the mist.

The first fluid is preferably a liquid and is more preferably water acting as a fire fighting agent. The second fluid is preferably a gas and more preferably an inert gas for both atomizing and entrainment of the first fluid for generation and distribution of the mist. Preferably, the liquid and gas are delivered to the device at a sufficient flow rate and pressure for the device to generate a mist to address a fire in the enclosed space. One preferred mist fire protection system generates and distributes the mist in one of a volume, concentration, and/or density to address, preferably control or suppress, and more preferably extinguish a fire.

One exemplary embodiment of this aspect of the present invention is a fire protection system for addressing a fire with a mist. This system includes at least one mist generating device disposed in an enclosed space having a volume of at least 130 cu. m. (4590 cu. ft.). The at least one mist generating device includes (1) a first fluid passage having a first fluid inlet and a first fluid outlet disposed about a longitudinal axis of the device, the first fluid passage defining a working nozzle and a second fluid passage having a second fluid inlet, (2) a second fluid outlet, the second fluid passage disposed about the longitudinal axis of the device and co-axial with the first fluid passage, the second fluid passage defining a transport nozzle, (3) a solid protrusion disposed in the second fluid passage so that the transport nozzle defines a divergent flow pattern with respect to the longitudinal axis, and (4) a chamber in communication with the working nozzle and transport nozzle. The system also includes a self-contained fluid supply source including a liquid supply coupled to the first fluid inlet for discharge of liquid from the working nozzle as an annulus. The fluid supply further includes a gas supply coupled to the second fluid inlet at a pressure ranging from about 2.1 bar (30 psi.) to about 24.1 bar (350 psi.) for discharge from the transport nozzle to mix with the liquid annulus in the chamber so as to form the mist to address the fire. The fluid supply has a property selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage; (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

In this embodiment, the mist further has a property, which is selected from the group consisting of: (i) a majority of droplets having a diameter ranging from 1 to 10 microns, more preferably, substantially all of the droplets having a diameter ranging from 1 to 10 microns; (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space; (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about 1 kW/cu. m. to about 8 kW/cu. m.

Another embodiment of this aspect of the invention is a fire protection system for addressing a fire with a mist. This system comprises at least one mist generating device disposed in an enclosed space having a volume of at least 130 cu. m. (4590 cu. ft.), the at least one mist generating device including (1) a first fluid passage having a first fluid inlet and a first fluid outlet disposed about a longitudinal axis of the device, the first fluid passage defining a working nozzle, (2) a second fluid passage having a second fluid inlet and a second fluid outlet, the second fluid passage disposed about the longitudinal axis of the device and co-axial with the first fluid passage, the second fluid passage defining a transport nozzle, (3) a solid protrusion disposed in the second fluid passage so that the transport nozzle defines a divergent flow pattern with respect to the longitudinal axis and (4) a chamber in communication with the working nozzle and transport nozzle In this embodiment, the at least one mist generating device is mounted within the enclosed space in a manner selected from the group consisting of: (i) at least two mist generating devices disposed in the enclosed space, wherein the at least 130 cu. m. (4590 cu. ft.) is at least 260 cu. m. (9180 cu. ft.), the at least two mist generating devices disposed in diagonally opposed corners so as to define a minimum spacing therebetween of about 3.4 m. (11 ft.); (ii) being mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.), (iii) being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space; (iv) at least two mist generating devices mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.) and spaced from one another by a distance ranging from about 3.4 m. (11 ft.) to about 6.7 m. (22 ft.); and (v) at least two mist generating devices being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space such that the at least two mist generating devices each define a center line of discharge having an unobstructed discharge path with a diameter of about 1.5 m. (5 ft.) from the device to an opposing wall, the device being mounted from the opposing wall at a distance ranging between about 3.8 m. (12.5 ft.) to about 12.0 m. (39.3 ft.) with the center lines of discharge of the at least two devices having a perpendicular spacing ranging between 1.0 m. (3.3 ft.) to about 4.6 m. (15 ft.).

This system further includes a self-contained fluid supply source including a liquid supply coupled to the first fluid inlet for discharge of liquid from the working nozzle as an annulus, the fluid supply further including a gas supply coupled to the second fluid inlet at a pressure ranging from about 2.1 bar (30 psi.) to about 24.1 bar (350 psi.) for discharge from the transport nozzle to mix with the liquid annulus in the chamber so as to form the mist to address the fire. The fluid supply further has a property that is selected from the group consisting of: (i) the liquid supply pressurized by the gas supply, the liquid supply being coupled to the first fluid inlet to provide the liquid to the inlet at a pressure of at least 0.5 bar (7 psi) for liquid flow through the first fluid passage, (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, defines a total extinguishing volume of less than about 8 gallons (8 gal.) for each 130 cu. m. (4590 cu. ft.) of enclosed space, and an extinguishment time ranging from about 780 seconds to about 80 seconds for a normalized sized fires ranging between about (1 kW/cu. m.) to about (8 kW/cu. m.).

Another embodiment of the invention is a fire protection system for addressing a fire with a mist. This system comprises: at least one atomizing device disposed in an enclosed space having a volume of at least 130 cu. m. (4590 cu. ft.), the at least one atomizing device including: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between 119,000 cu. mm and 121,500 cu. mm., a second fluid passage having a second fluid inlet and a second fluid outlet through which a second fluid passes, the second fluid passage disposed about the longitudinal axis concentric, or substantially concentric, with the first fluid passage, the second fluid passage defining an equivalent angle of expansion ranging from about 1 to about 40 degrees, the second fluid passage defining a total volume ranging between about 24,300 cu. mm. to about 25,500 cu. mm., and a chamber in communication with the first and second fluid outlets, wherein the first and second fluid outlets are oriented relative to one another such that they have an angle of incidence between about 5 degrees and about 30 degrees.

The system further includes a self-contained fluid supply source including a liquid supply coupled to the first fluid inlet for discharge of liquid from the first fluid outlet as an annulus. The fluid supply also includes a gas supply coupled to the second fluid inlet at a pressure ranging from about 2.1 bar (30 psi.) to about 24.1 bar (350 psi.) for discharge from the second fluid outlet to mix with the liquid annulus in the chamber so as to form the mist to address the fire. The fluid supply further has a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage; (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fire ranging between about 1 kW/cu. m. to about 8 kW/cu. m.

A further embodiment of the invention is a fire protection system for addressing a fire with a mist. This system comprises: at least one atomizing device disposed in an enclosed space having a volume of at least 130 cu. m. (4590 cu. ft.). The at least one atomizing device includes: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm., a second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between about 24,300 cu. mm. to about 25,500 cu. mm., and a chamber in communication with the first and second fluid outlets, wherein the first and second fluid outlets are oriented relative to one another such that they have an angle of incidence between about 5 degrees and about 30 degrees.

In this system, the device may be mounted within the enclosed space in a manner that is selected from the group consisting of: (i) at least two mist generating devices disposed in the enclosed space, wherein the at least 130 cu. m. (4590 cu. ft.) is at least 260 cu. m. (9180 cu. ft.), the at least two mist generating devices are disposed in diagonally opposed corners so as to define a minimum spacing therebetween of about 3.4 m. (11 ft.), (ii) being mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.), (iii) being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space, (iv) at least two mist generating devices mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.) and spaced from one another by a distance ranging from about 3.4 m. (11 ft.) to about 6.7 m. (22 ft.), and (v) at least two mist generating devices being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space such that the at least two mist generating devices each define a center line of discharge having an unobstructed discharge path with a diameter of about 1.5 m. (5 ft.) from the device to an opposing wall, the device being mounted from the opposing wall at a distance ranging between about 3.8 m. (12.5 ft.) to about 12.0 m. (39.3 ft.) with the center lines of discharge of the at least two devices having a perpendicular spacing ranging between 1.0 m. (3.3 ft.) to about 4.6 m. (15 ft.).

This system further includes a self-contained fluid supply source, which has a liquid supply coupled to the first fluid inlet for discharge of liquid from the first fluid outlet as an annulus. The fluid supply further including a gas supply coupled to the second fluid inlet at a pressure ranging from about 2.1 bar (30 psi.) to about 24.1 bar (350 psi.) for discharge from the second fluid outlet to mix with the liquid annulus in the chamber so as to form the mist to address the fire. The fluid supply further having a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage, (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet, and (iii) the liquid and gas being provided to the device in a liquid-to-gas mass flow ratio ranging from about 1:1 to about 3:1.

In this system, the mist has a property selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about 1 kW/cu. m. to about 8 kW/cu. m.

Another embodiment of the invention is a fire protection system for addressing a fire with a mist. This system comprises: at least one atomizing device disposed in an enclosed space having a volume of at least 130 cu. m. (4590 cu. ft.). The at least one atomizing device includes: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm., a second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between 24,300 cu. mm. to about 25,500 cu. mm., and a self-contained fluid supply source including a liquid supply coupled to the first fluid inlet for discharge of liquid from the first fluid outlet as an annulus, the fluid supply further including a gas supply coupled to the second fluid inlet at a pressure ranging from about 2.1 bar (30 psi.) to about 24.1 bar (350 psi.) for discharge from the second fluid outlet to mix with the liquid annulus in an optional chamber as, e.g., disclosed herein, so as to form the mist to address the fire.

In this system, the fluid supply further has a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage, (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about 1 kW/cu. m. to about 8 kW/cu. m.

A further embodiment of the invention is a fire protection system for addressing a fire with a mist. This system comprises at least one atomizing device disposed in an enclosed space having a volume of at least 130 cu. m. (4590 cu. ft.). The at least one atomizing device includes: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm. and a second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between 24,300 cu. mm. to about 25,500 cu. mm.

In this system, the device is mounted within the enclosed space in a manner that is selected from the group consisting of: (i) at least two mist generating devices disposed in the enclosed space, wherein the at least 130 cu. m. (4590 cu. ft.) is at least 260 cu. m. (9180 cu. ft.), the at least two mist generating devices disposed in diagonally opposed corners so as to define a minimum spacing therebetween of about 3.4 m. (11 ft.); (ii) being mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.), (iii) being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space, (iv) at least two mist generating devices mounted in a pendent configuration for an enclosure height ranging between about 3.0 m. (9.8 ft.) to about 5.0 m. (16.4 ft.) with a clearance from any wall of the enclosed space ranging from about 1.2 m. (4 ft.) to about 3.4 m. (11 ft.) and spaced from one another by a distance ranging from about 3.4 m. (11 ft.) to about 6.7 m. (22 ft.), and (v) at least two mist generating devices being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space such that the at least two mist generating devices each define a center line of discharge having an unobstructed discharge path with a diameter of about 1.5 m. (5 ft.) from the device to an opposing wall, the device being mounted from the opposing wall at a distance ranging between about 3.8 m. (12.5 ft.) to about 12.0 m. (39.3 ft.) with the center lines of discharge of the at least two devices having a perpendicular spacing ranging between 1.0 m. (3.3 ft.) to about 4.6 m. (15 ft.).

The system further includes a self-contained fluid supply source including a liquid supply coupled to the first fluid inlet for discharge of liquid from the first fluid outlet as an annulus, the fluid supply further including a gas supply coupled to the second fluid inlet at a pressure ranging from about 2.1 bar (30 psi.) to about 24.1 bar (350 psi.) for discharge from the second fluid outlet to mix with the liquid annulus in an optional chamber as, e.g., disclosed herein, so as to form the mist to address the fire. The fluid supply further has a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage; (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space, and (iv) an extinguishment time ranging from about 780 seconds to about 80 seconds for normalized sized fires ranging between about (1 kW/cu. m.) to about (8 kW/cu. m.).

Another embodiment of the invention is a fire protection system for addressing a fire with a mist. This system comprises at least one atomizing device disposed in an enclosed space having a volume of at least 130 cu. m. (4590 cu. ft.). The at least one atomizing device includes: a first fluid inlet and a second fluid inlet, means for atomizing a first fluid and with a second fluid, and a self-contained fluid supply source including a liquid supply coupled to the first fluid inlet for discharge of liquid from the atomizing device as an annulus, the fluid supply further including a gas supply coupled to the second fluid inlet at a pressure ranging from about 2.1 bar (30 psi.) to about 24.1 bar (350 psi.) for discharge from the atomizing device to mix with the liquid annulus in the chamber so as to form the mist to address the fire. The fluid supply further having a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage, (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet, and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about (1 kW/cu. m.) to about (8 kW/cu. m.).

A further embodiment of the invention is a fire protection system for addressing a fire with a mist. This system comprises at least one atomizing device disposed in an enclosed space having a volume of at least 130 cu. m. (4590 cu. ft.). The at least one atomizing device includes: a first fluid inlet and a second fluid inlet and means for atomizing a first fluid and with a second fluid. In this system, the atomizing device is mounted within the enclosed space in a manner that is selected from the group consisting of: (i) at least two mist generating devices disposed in the enclosed space, wherein the at least 130 cu. m. (4590 cu. ft.) is at least 260 cu. m. (9180 cu. ft.), the at least two mist generating devices disposed in diagonally opposed corners so as to define a minimum spacing therebetween of about 3.4 m. (11 ft.), (ii) being mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.), (iii) being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space, (iv) at least two mist generating devices mounted in a pendent configuration for an enclosure height ranging between about 3.0 m. (9.8 ft.) to about 5.0 m. (16.4 ft.) with a clearance from any wall of the enclosed space ranging from 1.2 m. (4 ft.) to about 3.4 m. (11 ft.) and spaced from one another by a distance ranging from about 3.4 m. (11 ft.) to about 6.7 m. (22 ft.), and (v) at least two mist generating devices being mounted in a sidewall configuration for a sidewall enclosure height ranging between about 1.0 m. (3.3 ft.) to about 5.0 m. (16.4 ft.) beneath a ceiling of the enclosed space ranging from about 1.0 m. (3.3 ft.) to about one half the ceiling enclosure height and with a clearance of at least 1.0 m. (3.3 ft.) from any corner of the enclosed space such that the at least two mist generating devices each define a center line of discharge having an unobstructed discharge path with a diameter of about 1.5 m. (5 ft.) from the device to an opposing wall, the device being mounted from the opposing wall at a distance ranging between about 3.8 m. (12.5 ft.) to about 12.0 m. (39.3 ft.) with the center lines of discharge of the at least two devices having a perpendicular spacing ranging between 1.0 m. (3.3 ft.) to about 4.6 m. (15 ft.).

This system further includes a self-contained fluid supply source including a liquid supply coupled to the first fluid inlet for discharge of liquid from the atomizing device as an annulus, the fluid supply further including a gas supply coupled to the second fluid inlet at a pressure ranging from about 2.1 bar (30 psi.) to about 24.1 bar (350 psi.) for discharge from the atomizing device to mix with the liquid annulus in an optional chamber as, e.g., disclosed herein, so as to form the mist to address the fire. The fluid supply further having a property that is selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage, (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet, and (iii) the liquid and gas being provided to the device in a liquid-to-gas mass flow ratio ranging from about 1:1 to about 3:1.

In this system, the mist further has a property that is selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about (1 kW/cu. m.) to about (8 kW/cu. m.).

In another embodiment of this aspect of the invention, there is provided a fire protection system for addressing a fire with a mist, the fire having a normalized fire size ranging between about (1 kW/cu. m.) to about (8 kW/cu. m.). This system comprises: an atomizer disposed in an enclosed space having a volume of about 130 cu. m. (4590 cu. ft.). The atomizer includes: a first fluid passage having a first fluid inlet and a first fluid outlet disposed about a longitudinal axis of the apparatus, the first fluid passage defining a working nozzle, a second fluid passage having a second fluid inlet and a second fluid outlet, the second fluid passage disposed about the longitudinal axis of the apparatus and co-axial with the first fluid passage, the second fluid passage defining a transport nozzle, a solid protrusion disposed in the second fluid passage so that the transport nozzle defines a divergent flow pattern with respect to the longitudinal axis, and a chamber in communication with the working nozzle and transport nozzle, a fluid supply source including a liquid supply coupled to the first fluid inlet at a flow rate of about 5.7 lpm (1.5 gpm) from the working nozzle, the fluid supply further including a gas supply coupled to the second fluid inlet at a pressure ranging from about 6.9 bar (100 psi) for discharge from the transport nozzle to mix with the liquid in the chamber so as to form the mist to extinguish the fire.

In this system, the mist further has a property that is selected from the group consisting of: (i) a majority of droplets having a diameter ranging from 1 to 10 micron, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space; and (iv) an extinguishment time ranging from about 780 seconds to about 80 seconds for normalized sized fires ranging between about (1 kW/cu. m.) to about (8 kW/cu. m.).

A further embodiment of the invention is a water mist fire protection system to extinguish a fire including an exposed, shielded, pool, spray and/or cascading fire. This system comprises at least one atomizer installed for introduction of a water mist volume into an occupancy, the at least one atomizer coupled to a fluid supply and a gas supply, the fluid supply being a water supply and the gas supply being a volume of nitrogen gas ($N_2$), wherein the water mist volume generated is defined by the gas being delivered at a pressure ranging from about 2.1 bar (30 psi.) to about 24.1 bar (350 psi).

Moreover, each of the systems disclosed herein is preferably scalable to address either an increasing or decreasing enclosure volume. More specifically, one preferred system is preferably configured to discharge a volume in relation to the size of the enclosed space to be protected. Thus, in one preferred aspect of this embodiment, the at least one atomizer is a single atomizer that provides substantially equivalent fire protection compared to two or more of the same atomizer, when the total volume discharged in the single atomizer is equivalent to the total volume discharged by the two or more atomizers.

Methods of Mist Fire Protection

One embodiment of this aspect of the present invention is a method of mist fire protection to address a fire in a substantially enclosed space having a volume of at least one hundred thirty cubic meters (130 cu. m. (4590 cu. ft.)), which comprises using at least one atomizing device disposed in the space for discharge of a mist into the space, the at least one atomizing device being a twin fluid atomizing device for a first fluid and a second fluid that includes a first fluid passage and a second fluid passage, the first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm., the second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between 24,300 cu. mm. to about 25,500 cu. mm., the second fluid passage defining a transport nozzle. This method further includes generating a liquid mist using the at least one atomizing device including: delivering a liquid as the first fluid to the first fluid inlet through the first fluid passage for a discharge of the liquid from the first fluid outlet as an annulus, delivering a gas as the second fluid of to the second fluid inlet of the device at an operating pressure ranging between about 2.1 bar (30 psi.) to about 24.1 bar (350 psi.). for gas flow through the second fluid passage and discharge from the second fluid outlet to mix with the liquid annulus so as to form the mist, and distributing the mist throughout the enclosed space. In this method, the distributing includes discharging the liquid and the gas from the atomizing device for a discharge time of at least ten minutes. The discharging the gas includes discharging the gas at a velocity of at least sonic velocity such that the mist has a property selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.)

(twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space, and (iv) an extinguishment time ranging from about 780 seconds to about 80 seconds for normalized sized fires ranging between about (1 kW/cu. m.) to about (8 kW/cu. m.).

Another embodiment of this aspect of the present invention is a method of total flooding mist fire protection for an enclosed space. This method comprises: discharging a volume of mist from at least one atomizing device into the enclosed space, distributing the volume of mist so as to define a density for each unit of volumetric space in the room capable of extinguishing a fire located anywhere in the room, and providing a self-contained fluid supply source. The self contained fluid supply source includes: a liquid supply coupled to the at least one atomizing device for discharge of liquid from the device as an annulus; and a gas supply coupled to the at least one atomizing device at a pressure ranging from about 2.1 bar (30 psi.) to about 24.1 bar (350 psi.) for discharge from the device to mix with the liquid annulus so as to form the mist. In this method, the providing further being selected from the group consisting of: (i) the liquid supply pressurized by the gas supply, the liquid supply being coupled to the first fluid inlet to provide the liquid to the inlet at a pressure of at least 0.5 bar (7 psi.) for liquid flow through the first fluid passage; (ii) a pressurized gas supply that includes a bank of at least three (3) 11.3 cu. m. (400 cu. ft.) nitrogen gas cylinders, each cylinder being coupled to a piping manifold coupled to the second fluid outlet with a regulated discharge pressure from the manifold of at least 6.9 bar (100 psi.), and a liquid supply that includes at least one ninety-five liter (95 L.) (twenty-five gallon (25 gal.)) tank of fire fighting liquid pressurized by the gas supply discharge pressure, the tank being coupled to the first fluid inlet; and (iii) the liquid and gas being provided to the device in a liquid-to-gas mass flow ratio ranging from about 1:1 to about 3:1.

This method may further comprise generating the mist by means of one of the parameters selected from the group consisting of: (i) a majority of droplets having a diameter ranging from 1 to 10 microns, (ii) a total liquid supply ranging between about fifty-seven liters (57 L.) (fifteen gallons (15 gal.)) to about ninety-five liters (95 L.) (twenty-five gallons (25 gal.)) for each 130 cu. m. (4590 cu. ft.) of enclosed space, (iii) defines a total extinguishing volume of less than about 8 gallons (8 gal.) for each 130 cu. m. (4590 cu. ft.) of enclosed space, and (iv) an extinguishment time ranging from about 780 seconds to about 80 seconds for normalized sized fires ranging between about (1 kW/cu. m.) to about (8 kW/cu. m.).

In this method, the at least one atomizer may comprise: a first fluid passage having a first fluid inlet and a first fluid outlet disposed about a longitudinal axis of the apparatus, the first fluid passage defining a working nozzle, a second fluid passage having a second fluid inlet and a second fluid outlet, the second fluid passage disposed about the longitudinal axis of the apparatus and co-axial with the first fluid passage, the second fluid passage defining a transport nozzle, a solid protrusion disposed in the second fluid passage so that the transport nozzle defines a divergent flow pattern with respect to the longitudinal axis, and a chamber in communication with the working nozzle and transport nozzle.

This method may further comprise generating liquid droplets forming the liquid mist, wherein a majority of the droplets have a diameter ranging from 1 to 5 microns. This method may further comprise generating turbulence in the volume so as to induce air currents capable of transporting and dispersing the liquid mist. In this method, the gas may be discharged at a supersonic speed. In this method, the discharging may include defining a total liquid volume to extinguish a normalized fire size measured in kilowatts per cubic meter (kW/cu. m.), the total extinguishing volume ranging respectively from about 0.57 liters per cubic meter (0.57 liters/cu. m.) (0.0042 gallons per cubic foot (0.0042 gal./cu. ft.)) to 0.057 liters per cubic meter (0.057 liters/cu. m.) (0.00042 gallons per cubic foot (0.00042 gal./cu. ft.)) for a normalized range of fire sizes ranging from about one (1 kW/m3) to about eight (8 kW/m3).

The discharging may be a function of the space being protected, which may have a volume of about 260 cubic meter (cu. m.) and the liquid mist may define an extinguishment volume of about four gallons (4 gal.) of liquid to about forty gallons (40 gal.).

In this method, discharging a liquid mist extinguishes a fire and defines a range of extinguishing times ranging respectively from about 780 seconds to about 80 seconds for normalized fire sizes ranging between about (1 kW/cu. m.) to about (8 kW/cu. m.).

In this method, preferably, discharging a liquid mist extinguishes a fire and defines a range of extinguishing times from about 500 seconds to about 80 seconds for normalized fire sizes ranging between about (1 kW/cu. m.) to about (8 kW/cu. m.).

In this method, more preferably, discharging a liquid mist extinguishes a fire and defines a range of extinguishing times from about, 420 seconds to about 80 seconds for normalized fire sizes ranging between about (1 kW/cu. m.) to about (8 kW/cu. m.).

In another embodiment of this aspect of the invention, a method of generating a mist is provided. This method comprises: passing a first fluid through a first fluid passage of a mist generating apparatus, wherein the first fluid passage has a first fluid outlet, causing a second fluid to flow through a second fluid passage of the mist generating apparatus, wherein the second fluid passage has a second fluid outlet and a throat portion, the throat portion having a smaller cross sectional area than the second fluid outlet, wherein the first and second fluid outlets are oriented relative to one another such that they have an angle of incidence between 5 and 30 degrees, accelerating the flow of second fluid through the throat portion of the second fluid passage, and ejecting the first and second fluids from their respective outlets such that a stream of accelerated second fluid issuing from the second fluid outlet imparts a shear force on a stream of first fluid issuing from the first fluid outlet, thereby at least partially atomising the first fluid to create a dispersed droplet flow regime.

Another embodiment of this aspect of the invention is a method of generating a mist. This method comprises: passing a first fluid through a first fluid passage of a mist generating apparatus, wherein the first fluid passage has a first fluid outlet, causing a second fluid to flow through a second fluid passage of the mist generating apparatus, wherein the second fluid passage has a second fluid outlet and a throat portion, the throat portion having a smaller cross sectional area than the second fluid outlet such that the area ratio between the throat portion and the second fluid outlet is between 2:3 and 1:4, wherein the first and second fluid outlets are oriented relative to one another such that they have an angle of incidence of less than 90 degrees, accelerating the flow of second fluid through the throat portion of the second fluid passage, and ejecting the first and second fluids from their respective outlets such that a stream of accelerated second fluid issuing from the second fluid outlet imparts a shear force on a stream of first fluid issuing from the first fluid outlet, thereby at least partially atomising the first fluid to create a dispersed droplet flow regime.

The previous two embodiments may further comprise: creating a turbulent region in the second fluid downstream of the outlets and passing the dispersed droplet flow regime through the turbulent region, thereby further atomising the first fluid in the dispersed droplet flow regime.

The methods of the present invention may further comprise the step of controlling the momentum flux ratio between the first and second fluids by varying the velocity and/or density of the first and/or second fluid.

The methods of present invention may further comprise the step of adjusting the cross sectional area of the first fluid outlet in order to vary the exit velocity of the first fluid stream. Preferably, the exit velocity is supersonic.

Assembly Methods

In another embodiment of the present invention, a method of assembling a mist generating apparatus is provided. This method comprises the steps of: forming a base member containing first and second fluid supply channels, forming a funnel member containing a bore, and axially and concentrically locating the funnel member on the base member such that the bore communicates with the second fluid supply channel, forming an elongate plug member, and axially and concentrically attaching the plug member to the base member such that a portion of the plug member lies within the bore and a second fluid passage is defined between the concentric funnel and plug members, forming a cover member, the cover member having a first end adapted to enclose the funnel and plug members, and adapted to axially and concentrically locate on the base member, the cover member further comprising a second end having an outlet, and attaching the cover member to the base member such that a first fluid passage is defined between an external surface of the funnel member and an internal surface of the cover member, and a first fluid outlet of the first fluid passage and the second fluid outlet communicate with the outlet of the cover member.

In one aspect of this embodiment, the step of forming the funnel may include forming a flange portion projecting radially therefrom, and wherein the step of attaching the cover member to the base includes sandwiching the flange portion of the funnel between the cover member and the base.

In another aspect of this embodiment, the step of attaching the cover member to the base includes adapting the cover member such that the axial position of the cover member may be adjusted relative to the base.

In a aspect of this embodiment, the step of attaching the plug member to the base includes threading the plug member onto the base such that the axial position of the plug may be adjusted relative to the base and the funnel.

The Atomizing Device

In another embodiment of the present invention, an atomizing device is provided. This device comprises: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm., a second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between 24,300 cu. mm. to about 25,500 cu. mm., the second fluid passage defining a transport nozzle, and a chamber in communication with the first and second fluid outlets, wherein the first and second fluid outlets are oriented relative to one another such that they have an angle of incidence between about 5 degrees and about 30 degrees.

In another embodiment of this aspect of the present invention, an atomizing device is provided, which device comprises: a first fluid passage having a first fluid inlet and a first fluid outlet disposed about a longitudinal axis of the device, the first fluid passage defining a smooth curving profile that converges toward the longitudinal axis such that a flow path decreases in a direction from the first fluid inlet to the first fluid outlet, the first fluid passage defining a total volume ranging between about 119,000 cu. mm. to about 121,500 cu. mm. and a second fluid passage having a second fluid inlet and a second fluid outlet through which a second fluid passes, the second fluid passage disposed about the longitudinal axis concentric with the first fluid passage, the second fluid passage defining an equivalent angle of expansion ranging from about 1 to about 40 degrees, the second fluid passage defining a total volume ranging between 24,300 cu. mm. to about 25,500 cu. mm., the second fluid passage defining a transport nozzle, the second fluid passage being disposed at angle of incidence between the first and second fluid flow paths, the angle of incidence ranging between about 5 degrees and about 30 degrees.

In another embodiment of this aspect of the invention, an atomizing device for generating a mist from a liquid and a gas is provided. The atomizing device comprises: a first fluid passage having a first fluid inlet for receipt of the liquid at a flow rate between about 1-4 gpm, such as e.g., between about 3.8 lpm to about 7.61 lpm (1-2 gpm), the first fluid passage having a first fluid outlet disposed about a longitudinal axis of the apparatus for discharge from the first fluid passage as annulus, a second fluid passage having a second fluid inlet for receipt of the gas at a pressure of about 6.9 bar (100 psi.), the second fluid passage having a second fluid outlet for discharge of the gas, the second fluid passage isolated from the first passage disposed about the longitudinal axis of the apparatus and co-axial with the first fluid passage, a solid protrusion disposed in the second fluid passage so that the second fluid passage defines a divergent flow pattern with respect to the longitudinal axis. In this embodiment, the liquid and gas are discharged from the first and second fluid outlets so as to form a mist, which forms a substantially conical spray pattern. The spray pattern defining an included angle with the longitudinal axis of about 15 degrees. Preferably, the device further comprises a chamber in communication with the first and second fluid outlets for mixture of the liquid and gas discharge so as to form the mist.

In another embodiment of this aspect of the present invention, there is provided a mist generating apparatus having a longitudinal axis. This apparatus comprises: a first fluid passage having a first fluid inlet and a first fluid outlet and a second fluid passage having a second fluid inlet and a second fluid outlet. The first fluid passage surrounds the second fluid passage, and the first and second fluid outlets are oriented relative to one another such that they have an angle of incidence between 5 and 30 degrees. The second fluid passage has a throat portion located between the second fluid inlet and the second fluid outlet, wherein the throat portion has a smaller cross sectional area than that of either the second fluid inlet or second fluid outlet.

In this embodiment, preferably the area ratio between the throat portion and the second fluid outlet is between 2:3 and 1:4.

In this embodiment, the first fluid passage may be located radially outward from the second fluid passage.

Preferably, the first and second fluid passages are coaxial with the longitudinal axis of the apparatus.

In this embodiment, the first fluid passage may comprise an intermediate portion located between the first fluid inlet and the first fluid outlet, wherein the intermediate portion has a cross sectional area which is larger than that of either the first fluid inlet or the first fluid outlet.

In this embodiment, the apparatus may further comprise: a first fluid supply channel having a first end adapted to be connected to a supply of a first fluid and a second end connected to the first fluid inlet and a second fluid supply channel having a first end adapted to be connected to a supply of a second fluid and a second end connected to the second fluid inlet, wherein the first and second supply channels are substantially parallel to the longitudinal axis of the apparatus. Preferably, the apparatus further comprises a base member that contains the first and second fluid supply channels.

The apparatus may further comprise a funnel member and an elongate plug member, wherein the funnel member has a bore and is adapted to coaxially locate upon the base member such that the bore communicates with the second fluid supply channel, and wherein the plug member is adapted to be attached to the base member such that a portion of the plug lies within the bore and the second fluid passage is defined between the funnel and the plug.

The apparatus may further comprise a cover member which encloses the base member, the funnel member and the plug member such that the first fluid passage is defined between an outer surface of the funnel and an inner surface of the cover member. Preferably, the cover member has a first end adapted to coaxially locate upon the base member and be attached thereto, and a second end having an outlet adapted to communicate with the first and second fluid outlets. Preferably, the second end of the cover includes an axially projecting lip portion, the lip portion defining an aperture in communication with the first and second fluid outlets.

In the apparatus, the plug member has a first end which attaches to the base member and a second end which defines the second fluid passage, wherein the second end has an end face which is concave.

In the apparatus, the funnel member may include a radially projecting flange portion, wherein the flange portion is sandwiched between the base member and the cover member to maintain the axial position of the funnel member relative to the base member.

The apparatus may be adapted such that the axial position of the cover member may be adjusted relative to the base.

In the apparatus, the plug member may be threaded onto the base such that the axial position of the plug member may be adjusted relative to the base and the funnel.

In another embodiment of this aspect of the present invention, there is provided a mist generating apparatus having a longitudinal axis. The apparatus comprises: a first fluid passage having a first fluid inlet and a first fluid outlet and a second fluid passage having a second fluid inlet and a second fluid outlet. The first fluid passage surrounds the second fluid passage and the first and second fluid outlets are oriented relative to one another such that they have an angle of incidence of less than 90 degrees. In this apparatus, the second fluid passage includes a throat portion located between the second fluid inlet and the second fluid outlet, the throat portion having a smaller cross sectional area than that of either the second fluid inlet or second fluid outlet such that the area ratio between the throat portion and the second fluid outlet is between 2:3 and 1:4. The apparatus includes the first fluid passage being located radially outward from the second fluid passage.

In this embodiment, the first and second fluid passages are coaxial with the longitudinal axis of the apparatus.

In this embodiment, the first fluid passage includes an intermediate portion located between the first fluid inlet and the first fluid outlet, the intermediate portion having a cross sectional area which is larger than that of either the first fluid inlet or the first fluid outlet.

The apparatus of this embodiment further comprises: a first fluid supply channel having a first end adapted to be connected to a supply of a first fluid and a second end connected to the first fluid inlet and a second fluid supply channel having a first end adapted to be connected to a supply of a second fluid and a second end connected to the second fluid inlet, wherein the first and second supply channels are substantially parallel to the longitudinal axis of the apparatus. In this embodiment, the apparatus further comprises a base member that contains the first and second fluid supply channels.

The apparatus may comprise a funnel member and an elongate plug member, wherein the funnel member has a bore and is adapted to coaxially locate upon the base member such that the bore communicates with the second fluid supply channel, and wherein the plug member is adapted to be attached to the base member such that a portion of the plug lies within the bore and the second fluid passage is defined between the funnel and the plug.

In this embodiment, the apparatus further comprises a cover member which encloses the base member, the funnel member and the plug member such that the first fluid passage is defined between an outer surface of the funnel and an inner surface of the cover member. Preferably, the cover member has a first end adapted to coaxially locate upon the base member and be attached thereto, and a second end having an outlet adapted to communicate with the first and second fluid outlets. In the apparatus of this embodiment, the second end of the cover includes an axially projecting lip portion, the lip portion defining an aperture in communication with the first and second fluid outlets.

In this embodiment, the plug member has a first end which attaches to the base member and a second end which defines the second fluid passage, wherein the second end has an end face which is concave.

In this embodiment, the funnel member includes a radially projecting flange portion, wherein the flange portion is sandwiched between the base member and the cover member to maintain the axial position of the funnel member relative to the base member. Preferably, the apparatus is adapted such that the axial position of the cover member may be adjusted relative to the base. In the apparatus of embodiment, the plug member may be threaded onto the base such that the axial position of the plug member may be adjusted relative to the base and the funnel.

Other alternative features of the mist generating apparatus are possible. For example, the cross sectional area of the throat portion may be between 20 and 35 $mm^2$, and an equivalent angle of expansion of the second fluid passage between the throat and the second fluid outlet may be between 5 and 10 degrees. The cross sectional area of the second fluid outlet may be between 4 and 7 times larger than the cross sectional area of the first fluid outlet. Moreover, the first and second fluid outlets may be located adjacent one another.

BRIEF DESCRIPTIONS OF THE DRAWINGS

The accompanying drawings, which are incorporated herein and constitute part of this specification, illustrate exemplary embodiments of the invention, and, together with the general description given above and the detailed description given below, serve to explain the features of the invention.

FIGS. 5-7 are respectively elevation, plan and side views of a self-contained fluid supply skid for use in the systems of FIGS. 1 and 3A-3D.

FIG. 12A is another detailed view of the atomizer assembly of FIG. 11.

FIG. 12B is a diagram of the relationship between the passages of the atomizer of FIG. 11.

FIG. 18A is a detailed view of the atomizer assembly of FIG. 18.

MODE(S) FOR CARRYING OUT THE INVENTION

Preferred Systems

Figure 1:
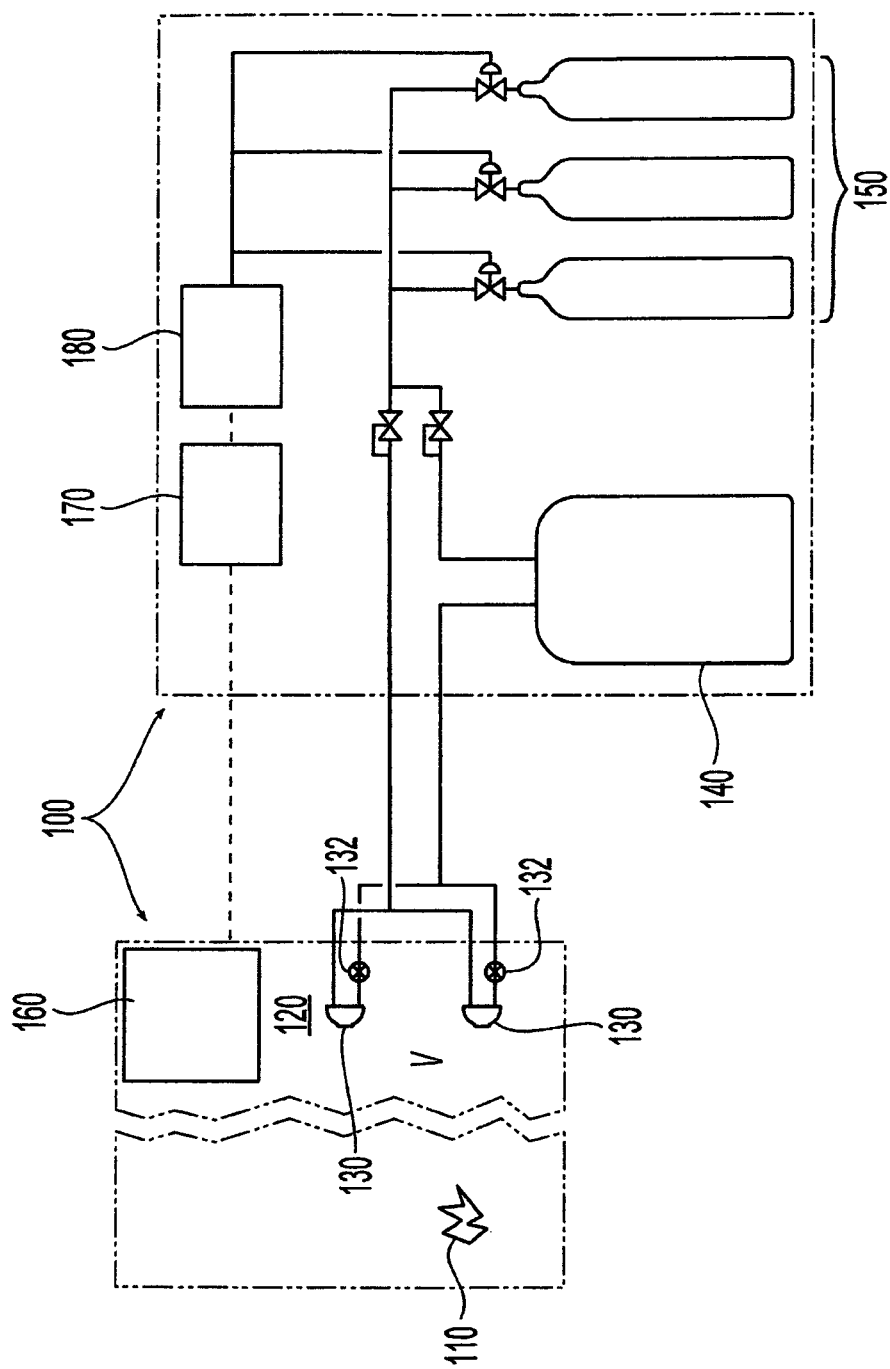
FIG. 1 is a schematic illustration of a preferred liquid mist fire protection system.

Shown in FIG. 1 is a preferred mist system 100, preferably a liquid mist, for providing total flooding mist fire protection of an enclosed space 120. More specifically, the mist system 100 provides for droplets of a fire fighting agent suspended in a gas that is distributed throughout the enclosed space in a concentration effective to address, preferably control or suppress and more preferably extinguish a fire. The fire fighting agent is preferably a liquid such as, for example, water. Alternatively, the fire fighting agent can be steam or further in the alternative, the fire fighting agent can be a foam such as, for example, an aqueous film forming foam (AFFF). The AFFF can be made from a synthetically produced material such as, for example, a liquid detergent mixed with water.

Examples of an enclosed space 120 for which the mist system 100 is suited includes, but are not limited to: engine rooms, turbo machinery rooms, or any other enclosure requiring fire protection of flammable liquid hazards in machinery spaces, special hazard machinery spaces, and/or combustion turbine enclosures. The enclosed space 120 can be characterized by various dimensional characteristics such as, for example, a total free volume V measured in cubic meters (cu. m.) or cubic feet (cu. ft.); or by its linear dimensions meters (m.) or feet (ft.) of length, height and width. The total free volume V is defined as the volume of the enclosure or room minus the fixed volume, in which the fixed volume is defined by the fixed or permanent equipment or other solid obstruction located in the enclosure.

The enclosed spaced 120 is preferably sealed off to prevent any ventilated exchange between the interior of the enclosed space and the outside environment. Alternatively, the maximum total area of all natural ventilation openings into the space, i.e., doorways, is no more than 4.0 square meters (sq. m.) (43.1 square feet (sq. ft.)). Further in the alternative, the maximum area of natural ventilation openings can increase provided the enclosed space has fire rated closures that automatically close upon actuation of the system 100. To the extent the enclosed space has forced ventilation systems, i.e., fans and/or dampers, the forced ventilation systems are preferably configured to shut off upon actuation of the preferred fire protection system 100.

The preferred system 100 includes at least one, and preferably two or more, devices 130 for generating and discharging a mist into a substantially enclosed space 120 to be protected which defines an enclosure volume V. The discharging devices 130 are preferably liquid atomizing devices or atomizers. In the liquid mist system 100, each of the atomizers 130 is in communication with a liquid source 140 of fire fighting fluid, preferably water, and a pressurized gas source 150, preferably nitrogen or some other compressible fluid. The gas source 150 preferably serves as an atomizing gas to generate the liquid mist and as a carrier gas for distribution of the liquid droplets forming the liquid mist. The gas source 150 is preferably inert and therefore the gas can further serve as an inerting agent, enhancing fire suppression performance.

Preferably, the liquid source 140 and the gas source 150 of the system 100 form a self-contained assembly such that the system 100 has an independent source of liquid and gas. In the preferred system 100, the liquid source 140 is preferably a dedicated stand alone tank of fire fighting liquid, and the gas source 150 is preferably a bank of inert gas cylinders. The gas source 150 is connected to a feed line which is coupled to, preferably in parallel, to the tank of water 140 and each one of the atomizers 130. The gas source 150 pressurizes the liquid source 140 so that the water can be provided to each atomizer 130 at a desired working pressure. The separate gas feed to the atomizers 130 provides the gas with which to atomize and entrain the liquid for mist generation. The gas discharge from the atomizers further provide for the high velocity, preferably sonic to supersonic velocity gas to transport and distribute the mist throughout the enclosure volume V. The liquid source 140 and gas source 150 are preferably sized to provide for a discharge duration from the atomizers of at least about ten minutes, although the system 100 can be configured for total discharge of the available liquid and gas supplies in a time that is either greater or less than ten minutes.

Figure 2:
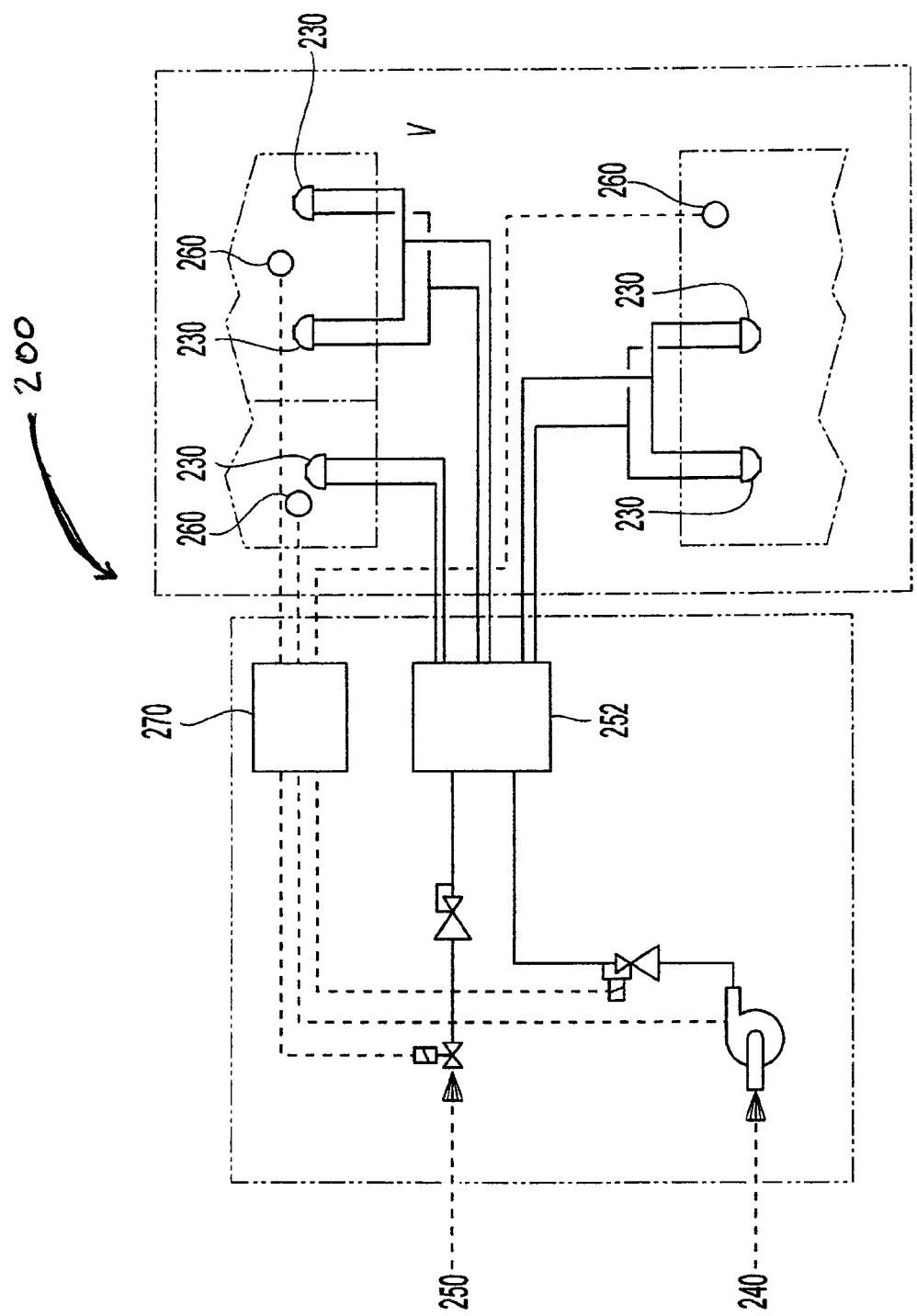
FIG. 2 is a schematic illustration of another embodiment of a preferred liquid mist fire protection system.

Shown in FIG. 2 is an alternate embodiment 200 of the preferred mist system. Instead of utilizing self-contained liquid and gas supplies, the system 200 uses available water and gas supplies of the facility being protected. For example, the system 200 and each of its atomizers 230 can be connected, via a manifold 252, to the main water supply 240 and the gas supply 250 of the facility, such as a plant, being protected by the preferred system.

Referring again to FIG. 1, the preferred system 100 provides, within the enclosed space 120, one or more detectors 160 capable of detecting the presence of a fire 110 in the enclosed space 120. The detectors 160 (260 in FIG. 2) are further preferably coupled to a pneumatic actuator 180 to provide automatic operation of the system 100. The detectors are further preferably configured to generate a signal to operate the pneumatic actuator 180. The detectors 160 are further preferably coupled to alarm panel 170 (270 in FIG. 2) to alert system operators for manual operation of the system. The detectors 160 can be configured as any one of a heat detector, infrared detector, fixed temperature detector, rate of temperature rise detector, smoke detector, chemical vapor detector, optical detector or a combination thereof. The detectors provide the system 100 redundancy or a double interlock configuration to prevent false trips of the system 100. In operation, the heat detectors 160 are preferably configured to generate a signal to trip an alarm signal at the panel 170 in order to provide audible and/or visual alarm signals that a fire 110 has been detected in the space 120.

The operation of the actuator 180 preferably initiates a discharge of gas from the gas source 150. The discharged gas pressurizes the liquid source 140 for delivery of the liquid fire fighting agent to each of the atomizers 130 at a desired working pressure or a preferred flow rate. In the preferred system 100, an in-line orifice 132 is disposed between the liquid source 140 and each of the atomizers 130 to provide the liquid to the atomizers 130 at a substantially constant flow rate and substantially constant operating pressure. Each of the atomizers 130 atomizes the incoming liquid to generate the liquid mist for discharge into the space 120 to address a fire 110. The gas is also delivered directly to the atomizer 130 to atomize the incoming fluid and for discharge as a high velocity jet stream. The liquid mist and gas is discharged with sufficient momentum to dislodge a protective cap disposed about the outlet of the atomizer. The protective cap 1002, shown for example in FIG. 21 (along with a preferred embodiment of an atomizer 1000), covers the outlet of the atomizer to protect the internals of the atomizer in its non-actuated state from any debris or contaminants that may be in the enclosed space 120. The gas is preferably discharged at a sonic to supersonic velocity, capable of creating turbulence within the enclosed space 120 and/or inducing low velocity currents that can transport and distribute the liquid mist throughout the enclosed space 120 to provide for preferred liquid mist total flooding fire protection.

The liquid mist is preferably composed of a large quantity of liquid droplets ranging in size from about 1 micron to about 10 microns and more preferably 1 to about 5 microns that are capable of being transported by the induced air currents. The discharged liquid droplets are dispersed throughout the enclosed space 120 so as to surround the fire 110. The droplets engage the fire, evaporate and generate a large volume of steam or liquid vapor capable of displacing oxygen. The rate of discharge of liquid mist and its density or concentration throughout the space is such that the rate of evaporation can effectively displace the oxygen so as to address the fire, preferably control or suppress the fire, and even more preferably extinguish the fire. In addition to displacing oxygen, the liquid vapor dilutes flammable vapors by the entrainment of the liquid vapor. As the liquid is converted to vapor, heat is extracted from the fire to cool the fuel.

Figures 3A, 3B:
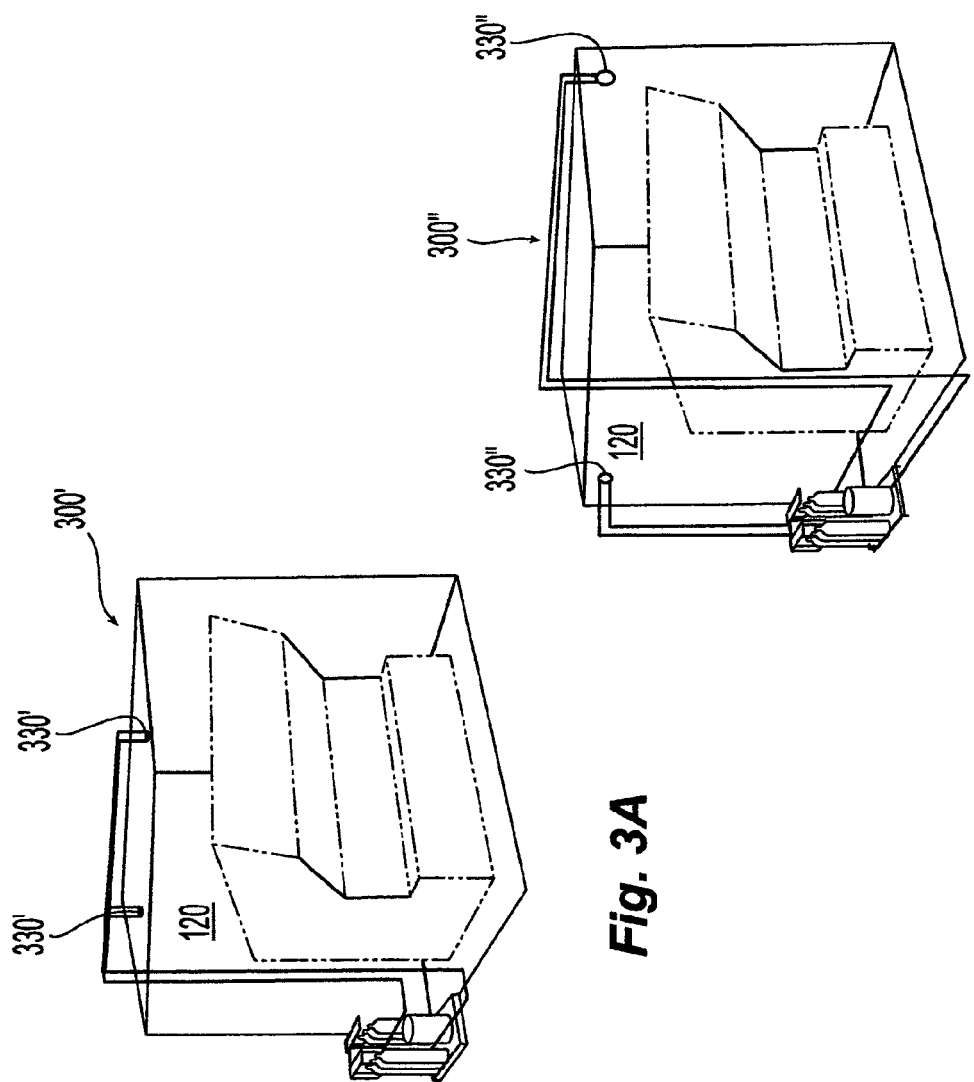
FIG. 3A is an isometric schematic illustration of an embodiment of the system of FIG. 1.
FIG. 3B is an isometric schematic illustration of another embodiment of the system of FIG. 1.
Figure 3C:
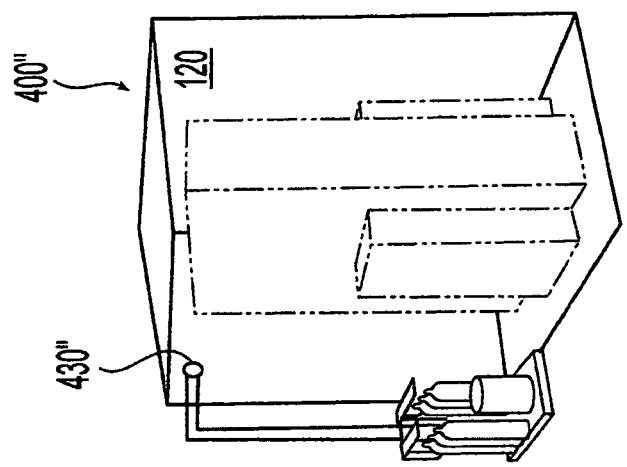
FIG. 3C is an isometric schematic illustration of another embodiment of the system of FIG. 1.
Figure 3D:
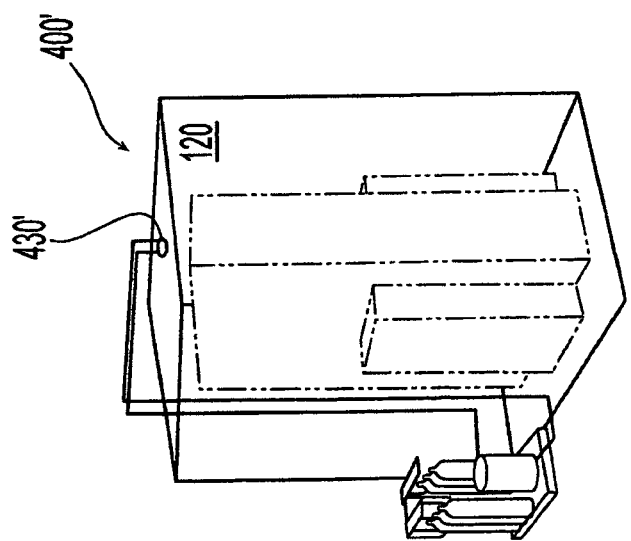
FIG. 3D is an isometric schematic illustration of yet another embodiment of the system of FIG. 1.

Further preferred embodiments of a liquid mist fire protection system with a self-contained fluid supply are shown schematically in FIGS. 3A-D, 4A and 4B and described in TYCO FIRE & BUILDING PRODUCTS draft Data Sheet TFP2280 entitled, "Aquasonic™: Total Flooding Water Mist Type 130 and 260 Systems" (Draft-November, 2007), which is attached to U.S. Provisional Patent Application No. 60/989,083 and incorporated by reference in its entirety. The system 300' of FIG. 3A is preferably configured with two atomizers 330' pendent mounted for protection of a substantially enclosed space defining a free volume up to 260 cubic meters (cu. m.) (9180 cu. ft.). The system 300" of FIG. 3B is preferably configured with two atomizers 330" sidewall mounted for protection of a substantially enclosed space defining a free volume up to 260 cubic meters (cu. m.) (9180 cu. ft.). The system 400' of FIG. 3C is preferably configured with a single atomizer 430' that is pendent mounted for protection of a substantially enclosed space defining a free volume up to 130 cubic meters (cu. m.) (4590 cu. ft.). The system 400" of FIG. 3D is preferably configured with a single atomizer 430" sidewall mounted for protection of an area up to 130 cubic meters (cu. m.) (4590 cu. ft.). For the pendent mounted systems 300', 400', fire protection is preferably provided to the enclosed space 120 in which the enclosure height can vary from about 3.0 meters to about 5.0 meters (about 9.8 ft. to about 16.4 ft.) up to about 8.0 meters (26.2 ft.). For the sidewall systems 300", 400", fire protection is preferably provided to the enclosed space 120 in which the enclosure height can vary from about 1.0 meter to about 3.0 meters to more preferably about 5.0 meter (about 3.3 to about 16.4 ft.) up to about 8.0 meters (26.2 ft.).

Although, testing of the preferred mist systems has demonstrated the ability to provide fire protection independent of the atomizer location within the enclosed space 120. The inventors have identified preferred locations for atomizer installation within the enclosed space 120. In the pendent systems 300', 400', the atomizers are preferably located at a minimum of about 1.2 m. (4 ft.), preferably a minimum of 0.3 m. (1 ft.) and a maximum 3.4 m. (11 ft.) from any enclosure wall such that the atomizer has an unobstructed discharge path of about 1.2 m. (4 ft. and more preferably 0.9 m. (3 ft.) in diameter from the atomizer to the floor of the enclosure. In the case of the dual pendent atomizer system 300' the atomizers are preferably located on opposite adjacent quadrants or corner areas of the enclosure 20' as shown, for example, in the plan installation schematic of FIG. 4A disposed about the fixed equipment 127. More preferably, the two atomizers 330 have a space D in between their centers of about 3.4 meters (11 ft.) and no greater than about 9.3 meters (30.4 ft).

A preferred installation for the sidewall mounted systems 300", 400" provide that the atomizers are preferably mounted on the shorter width walls of the enclosed space 120 where the enclosure space has a rectangular floor plan. The atomizers of the preferred sidewall systems are mounted at a minimum of about 1.0 meter (3.3 ft.) from any enclosure corner, and further at a minimum of 3.8 meters (12.5 ft.) to a maximum 12.0 meters (39.3 ft) from the opposing enclosure wall. Moreover, the atomizers 430' are preferably mounted at a minimum of about 1.0 meter (3.3 ft.) below the ceiling to no greater than half the enclosure height from the ceiling with an unobstructed discharge path of about 1.5 meters (4.9 ft.) diameter from atomizer to opposing enclosure wall.

Alternatively or in addition to, where a system installation cannot avoid an obstruction in the discharge path in either the pendent or sidewall configuration, the atomizers are preferably located such that the cross-sectional area of a discharged spray pattern contains no more than a 40% obstruction in the spray pattern development zone, and no more than 50% obstruction beyond the spray pattern development zone. The spray pattern development zone is defined as the region from the outlet end of the atomizer to a distance DZ distal of the atomizer where the spray pattern is fully developed. In the schematic of the preferred atomizer 1000 shown in FIG. 20, the spray pattern is considered fully developed about 64 inches from the outlet end of the atomizer at which point the spray pattern defines a circular cross-section having a diameter D1A of about 36 inches.

Figure 4A:
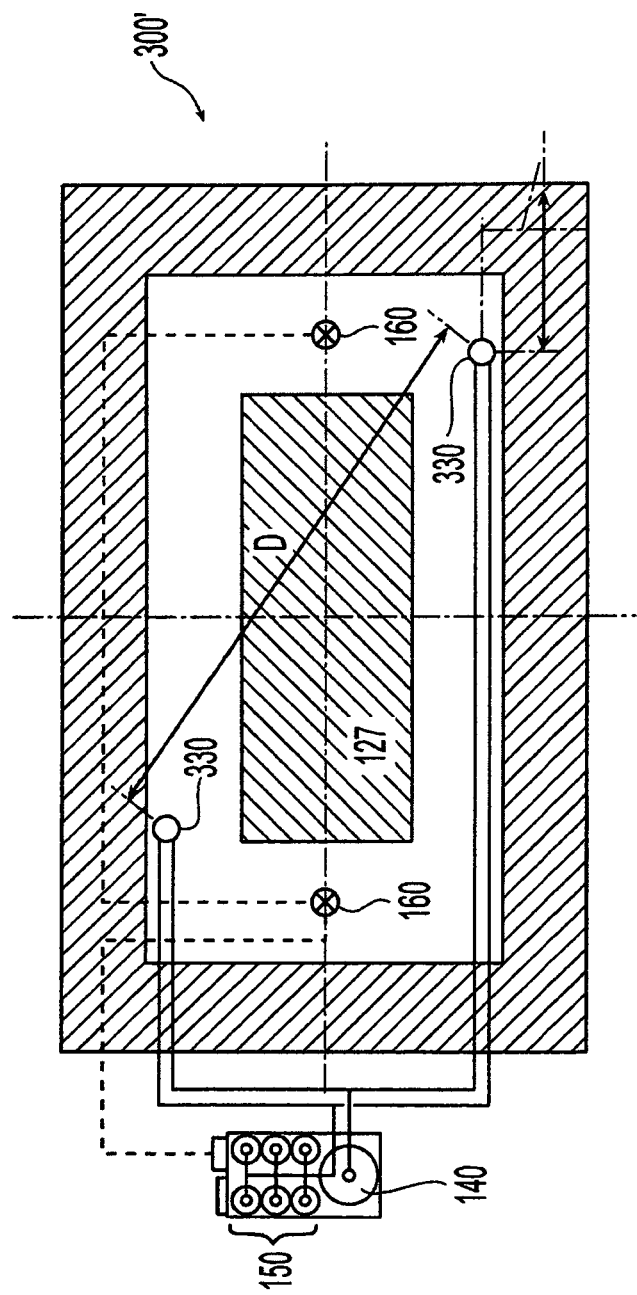
FIG. 4A is an installation schematic for the system of FIG. 3A.
Figure 4B:
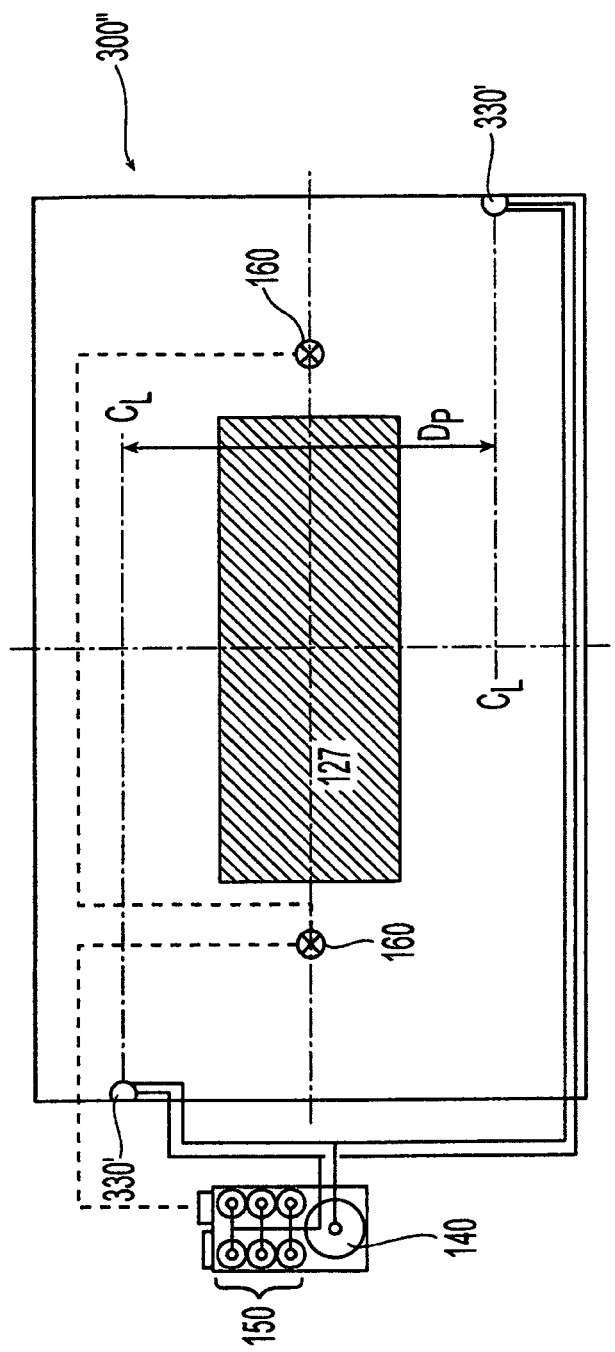
FIG. 4B is an installation schematic for the system of FIG. 3B.

In the case of the dual sidewall atomizer system 300", the atomizers 330' are preferably located on opposite adjacent quadrants or corner areas of the enclosure 20' as shown, for example, in the plan installation schematic of FIG. 4B. More preferably, the two atomizers 330' should have a space in between so as to define a perpendicular distance Dp between the atomizers' centerlines CL of discharge ranging between a minimum of about 1.0 meters (3 ft-3 in.) to a maximum of about 4.6 meters (15 ft-1 in.).

Preferred Piping Installation of the Water Mist Systems

Each of the atomizers in a preferred liquid mist system is preferably coupled to the fluid supply to ensure that the liquid is delivered to the atomizers at a preferred substantially constant flow rate and the gas is delivered to the atomizers at a desired operating pressure. A more preferred installation of a mist fire protection system having two atomizers for the protection of a 260 cubic meter space (9180 cu. ft.) with a self-contained fluid supply of gas and nitrogen gas is described in ANSUL INC. publication, Ansul Part No. 435650, entitled "Aquasonic™ Water-Atomizing Fire Suppression System Design, Installation, Recharge and Maintenance Manual" (2008), which is incorporated by reference in its entirety. The preferred installation provides for a system in conformance with the requirements of the NATIONAL FIRE PROTECTION ASSOCIATION published standard, "NFPA 750: Standard on Water Mist Fire Protection Systems" (May 2006). The preferred system is installed so as to provide automatic, manual and optional remote operation. As a self-contained system, the preferred installation provides for a portable skid mount for the liquid supply, gas supply and associated system controls. The skid is preferably configured for outdoor or indoor mounting, wherein particular, the skid defines a fluid supply and control assembly having a foot print or overall dimension such that the assembly can be moved through standard size doorways.

Shown at FIGS. 5-7 is a preferred self-contained fluid supply skid 500 for use in any one of the above described fluid mist systems. The preferred supply skid 500 includes a liquid source configured as a tank 502 having with a capacity of at least 95 liters (25 gallons) and more preferably capacity of about 191 liters (50 gallons) containing a fire fighting liquid, preferably water, for protection of at least a 130 cu. m. (4590 cu. ft.) enclosed space, and more preferably a 260 cu. m. (9180 cu. ft.) enclosed space. The tank 502 may be alternatively sized to provide a water supply based on the volume of the protected enclosure; however the tank should be sufficiently sized to provide for a mist discharge duration of at least ten minutes. The tank 502 is a pressure vessel, preferably ASME certified, to at least about 14.8 bar (215 psi.). The tank 502 further includes a fill inlet 506 and an outlet 508 for connection to system piping in communication with one or more atomizers.

The supply skid 500 further includes a gas source 510 that is preferably configured as a bank of cylinders of a substantially inert gas, for example, nitrogen gas. In the supply skid 500 shown, the bank of cylinders includes a total of six 11.3 cu. m. (400 cu. ft.) nitrogen gas cylinders staged for the protection of the 260 cu. m. (9180 cu. ft.) enclosed space. More or fewer cylinders may be provided depending upon the size of the space being protected, for example, the supply skid for protection of the 130 cu. m. (4590 cu. ft.) enclosed space includes a total of three 11.3 cu. m. (400 cu. ft.) cylinders. Regardless of the number or size of cylinders, the gas supply is preferably selected to provide a mist discharge duration of at least 10 minutes.

The tank 502 and cylinders 510 are housed within a skid supply frame 522 that is sized so that the entire skid assembly can fit through a standard size doorway. For the preferred skid assembly 502 shown, the skid has a maximum height H of about 22 m. (6.5 ft.) a maximum width W of about 0.9 m. (3 ft) and a maximum length L of about 1.6 m. (5.3 ft.)

In a preferred piping arrangement for any one of the above described self-contained water mist systems, the gas supply 510 pressurizes the liquid supply 502 such that the liquid and gas are delivered to the atomizer at the same operating pressure, preferably ranging between about 2.1 bar to 24.1 bar (30 psi. to 350 psi.), such as e.g., about 8.3 bar (120 psi.) to about 6.9 bar (100 psi.), between about 7.9 bar (115 psi.) and about 6.9 bar (100 psi.), between about 7.7 bar (112 psi) and about 6.9 bar (100 psi.), between about 7.6 bar (110 psi.) and about 6.9 bar (100 psi.), and is more preferably about 6.9 bar (100 psi.) More specifically, each of the gas cylinders 510 of the skid 500 is preferably equipped with a gas regulator 512 preferably set to a flowing pressure range between about 7.7 bar (112 psi.). to about 8.3 bar (120 psi.) for a pressurized gas feed into a piping manifold 514. The piping manifold 514 includes one discharge outlet end 516 to supply the gas to the atomizers of the system with a preferred minimum pressure of about 7.6 bar (110 psi.).

The manifold 514 further preferably includes a branched discharge outlet end 513 for coupling to the water tank 502 to pressurize the tank 502 of water or other liquid supply to a discharge pressure at the water feed outlet 508 of at least about 7.6 bar (110 psi.). Given the preferred size of the liquid and gas supplies in the preferred self-contained fluid supply skid 500, the piping between the feed outlet and each of the atomizers is sized so as to have a maximum piping volume of no more than about 50 liters (13 gal.) using pipe ranging from 15 mm. (½ inch) to 25 mm. (1 inch) pipe in diameter. Referring back to the system schematic of FIG. 1, the water supply piping further preferably includes an in-line orifice device 132 proximate the inlet of each atomizer inlet to step down the fluid pressure to the atomizer to a preferably substantially constant pressure of about 0.5 bar (7 psi.) and a more preferred flow rate of about 5.7 lpm (1.5 gpm). The preferred in-line restriction orifice has a restriction orifice diameter preferably ranging from about 0.080 inches to about 0.092 inches with a coefficient of flow efficiency (Cd) of approximately 0.78. Alternatively or in addition to, the in-line orifice defines a range of K-factors ranging from about 2.13 lpm./(bar)$^{1/2}$ (0.148 gpm./(psi) %) to about 2.13 lpm./(bar)$^{1/2}$ (0.196 gpm./(psi)$^{1/2}$), wherein the total flow from the atomizer and orifice assembly is equal to the K-factor multiplied by the square root of the water supply pressure. Accordingly, the gas regulator and the liquid orifice facilitate a constant preferred liquid to gas mass flow ratio in each of the atomizers.

The liquid mist systems preferably provide for manual, automatic and/or remote actuation of the system. Accordingly, as seen in FIG. 5, the supply skid 500 preferably includes a control panel 515 that automatically actuates the liquid mist system after receiving an input signal from one or more initiating devices, i.e., a manual actuator or one of the detectors 160. The control panel 515 further preferably provides for manual actuation of the system with a manual operating switch that can be operated locally or remotely.

Figure 8:
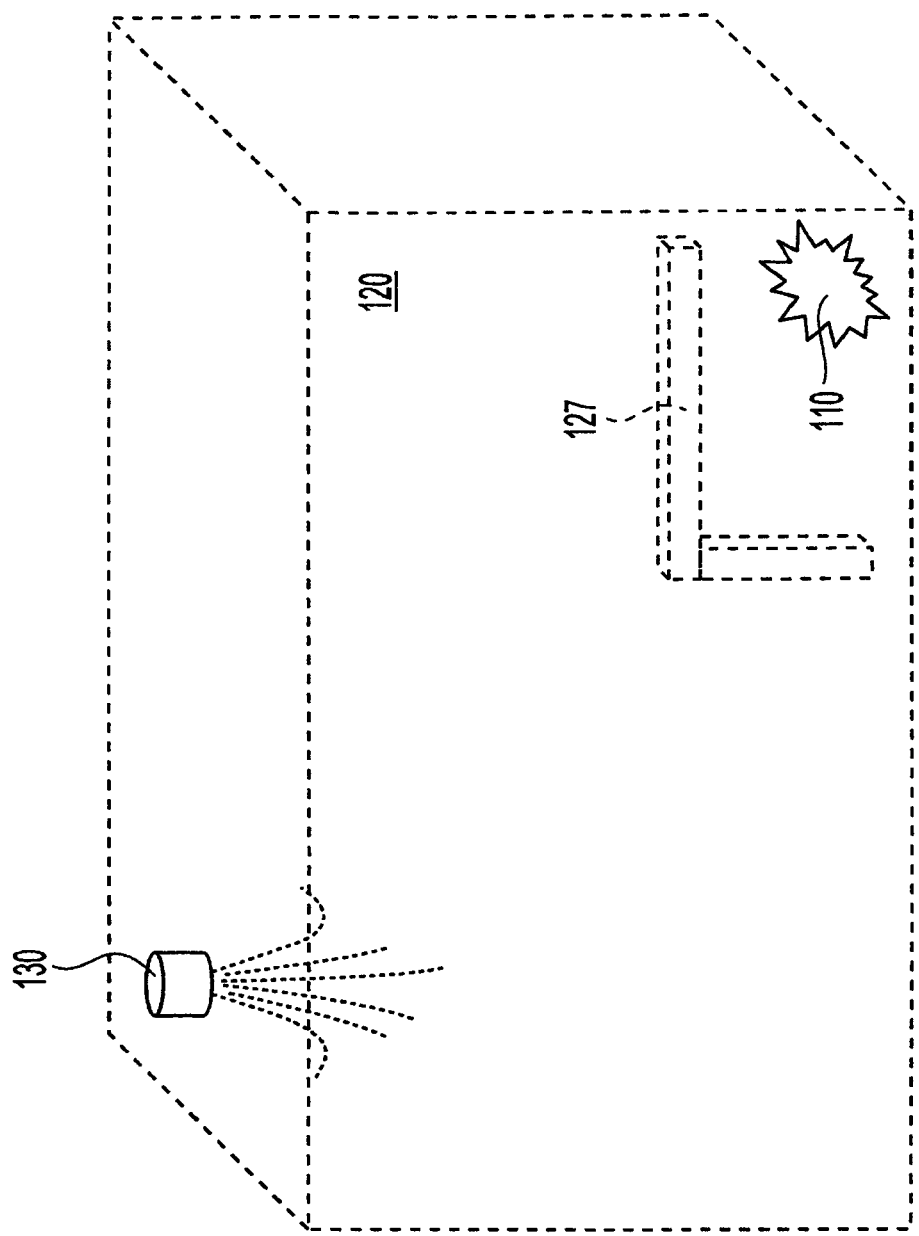
FIG. 8 is a schematic illustration of the operation of the systems of FIGS. 1 and 2.

A preferred method of operation for each of the preferred water mist systems is shown in the schematic illustration of FIG. 8. The preferred method provides generating a liquid mist to effectively do at least one of address, control, suppress or more preferably extinguish a fire 110 in the enclosed area to be protected. In addition, the preferred method includes distributing the mist throughout the enclosed space 120 to effectively do at least one of address, control, suppress or more preferably extinguish a fire 110 in the enclosed area to be protected. The distribution of the liquid mist throughout the enclosed space 120 preferably provides total flooding of the mist within the enclosed spaces so as to substantially distribute the mist evenly or homogeneously throughout the enclosed space such that each unit volume of the enclosed space contains at least an amount or concentration of mist to effectively address the fire 110 regardless of the location or orientation of the mist generating device relative to the fire.

Distributing the liquid mist further preferably includes generating turbulence in the enclosed space so as to induce currents capable of transporting and dispersing the liquid mist. Preferably, the atomizers of the system discharge a gas in the enclosed space 120 at a high velocity ranging from sonic to a more preferably supersonic speed so as to provide for the preferred turbulence.

Generating the liquid mist preferably defines an average volume or mass of mist for each unit of volume of space (mist density), or at least each 130 cu. m. (4590 cu. ft.) of enclosure volume V in the enclosed space 120 that is capable of addressing a fire 110 located anywhere in the enclosed space 120 via total flooding. Accordingly, the preferred method can adequately address a fire 110 that is either shielded or obstructed by an object from the atomizer 130 or alternatively address a fire located outside the direct discharge path of the atomizer 130. Thus, the preferred method provides fire protection throughout substantially the entire enclosed space 120, independent of the location of the atomizer 130 relative to the fire. Moreover because the minimum amount of mist sufficient to address a fire is a function of the enclosure volume V of the enclosed space 120, the method of mist protection is independent of any particular linear dimensional characteristic of the enclosed space 120.

In addition, the minimum mist density may be a function of the manner in which a fire is to be addressed. For example, the preferred method can provide for a mist density configured to address a fire by any one of: control, suppression and/or extinguishment of a fire. More specifically, the preferred system and its method of generating a liquid mist that includes providing an appropriate distribution of droplets having a droplet size effective to address a fire. Preferably, the liquid mist is substantially composed of liquid droplets having a diameter under 50 microns, more preferably under 10 microns and even more preferably ranging from about 1 to about 5 microns. The small water droplet size makes it possible for low velocity air currents, stemming from the preferably generated turbulence, to transport and evenly distribute these droplets in multiple directions within the enclosed space 120.

It is believed that generating a liquid mist having liquid droplets in the preferred size range in combination with homogeneous distribution of the liquid mist throughout the enclosed space 120 can effectively address a fire independent of the location or orientation of the atomizer 130 by taking advantage of the evaporative capability of the liquid, for example water, to displace oxygen so as to starve a fire of oxygen in order to address, control, suppress or more preferably extinguish it. The oxygen displacement by water vapor occurs both locally, i.e., within the flame of the fire, and globally, i.e., outside the flame and within the enclosed space 120. Moreover the conversion of the water to vapor provides for the other fire fighting mechanism described above, for example, extracting heat from the fire cooling the fuel.

Water displaces oxygen by its evaporation, conversion and expansion from liquid to vapor. A liter of liquid water at atmospheric pressure expands to approximately 1600-1700 liters of water vapor upon evaporation. Accordingly, the displacement capability of liquid mist for a unit volume of liquid mist is directly related to the proportion of its volume capable of evaporation upon engagement with a fire or the heat emanating therefrom. Thus, the preferred mist systems and their method of operation deliver into the enclosed space 120 a discharge of mist in which a large proportion of the mist is capable of evaporation in a region proximate the fire plume. Typical fire plumes to be addressed by the preferred systems, range in velocity from about 1.5 meters per second (5 ft. per second) to about 15 meters per second (50 ft. per sec.), and the region in which water droplets of a water mist need to evaporate is within the initial 8 cm. to 30 cm. (3 to 12 inches) of the fire plume.

Not wishing to be limited by any particular theory, it is believed that water droplets within this region need to evaporate preferably within a range of 0.02 seconds to about 0.05 seconds to directly extinguish the fire through substantially localized oxygen depletion. By having a water mist in which a large distribution of the water droplets have a size in the preferred droplet size range of under 10 microns, the mist contains a distribution of droplets that can be evaporated within the 0.02 to 0.05 second range upon being within the initial 8 cm. to 30 cm. (3 to 12 inches) of the fire plume.

Moreover, because a greater portion of the discharge mist is used for oxygen depletion, a lesser amount of liquid is required to effectively address a fire as compared to conventional sprinkler systems. The preferred method of liquid mist fire protection, or more specifically total flooding, is believed to also use less water than known water mist fire protection systems to effectively address a fire. The preferred method and its discharged liquid mist includes additional mechanisms with which to address a fire growth, for example, in addition to displacing oxygen, the evaporation of the water droplets extracts heat from the fire thereby cooling the fuel.

The preferred mist systems and methods present an environmentally friendly or "green technology" for fire protection. Specifically, the low volumes of water used by the systems minimizes the water waste and runoff. In addition, the use of the preferred nitrogen gas as an atomizing and transport fluid does not present an additional hazard to the environment, system operators or personnel in the event of a fire and system actuation.

System Parameters

The design and performance of the preferred liquid mist systems as a whole can be defined as a function of one or more system input parameters such as, for example, the pressure and/or flow rate of the fluids to the atomizing devices, the volume and configuration of the enclosed space 120 to be protected, the fuel in the enclosed space to be protected, the anticipated fire type/size to be addressed by the system, and/or the size and configuration of ventilation opening in the enclosed space.

More specifically, the volume, flow, mist density, and/or droplet size of the fluid mist to be discharged by the system into the enclosed space 120 can be defined by, e.g., the inlet characteristics of the gas, the flow rate of liquid and/or the relation between the two. For example, in the mist fire protection systems described above, a given flow rate of liquid can provide for a liquid mist effective for addressing a fire provided there is a sufficient flow and pressure of atomizing gas. The atomizers 130 used in the preferred methods and systems described above are preferably configured as multi-fluid atomizers, for example such as, twin or dual fluid atomizers which preferably use a liquid and a gas for generating the mist. Preferred atomizers for use in the above preferred systems and methods are described in greater detail below. Alternatively, single fluid or other liquid atomizers may be used provided such devices can provide for the desired mist having appropriate volume concentration, droplet size and distribution characteristics as described herein.

Described herein below, for example, with respect to using the preferred atomizer of FIG. 11. Applicants have identified an inlet gas pressure or gas operating pressure for formation of the preferred liquid mist that ranges from about 2.1 bar to 24.1 bar (30 psi to 350 psi.); preferably ranges from about 5.0 bar to 13.8 bar (72 psi. to about 200 psi); more preferably ranges from about 5.9 bar to 9.0 bar (85 psi. to about 130 psi.); yet even more preferably ranges from about 6.9 bar to about 8.4 bar (100 psi. to about 122 psi.); and is most preferably about 7.6 bar (110 psi.). Alternatively or in addition to, these inlet gas pressures define mass flow rates and volumetric gas flow rates that preferably range from about 0.0141 kg/s (25 scfm) to about 0.1667 kg/s; 0.0476 kg/s (84 scfm) to about 0.0619 kg/s (109 scfm) and is preferably about 0.0476 kg/s (84 scfm). The preferred water mist systems and their operation are also more efficient than known water mist systems because the preferred systems 300', 400' operate at lower pressures than the known high pressure water mist systems. Specifically, known high pressure water mist systems require minimum operating pressure of about 70 bar (1015 psi.). Comparatively, the systems 300, 400 only require a minimum operating pressure of about 6.9 bar (100 psi.).

Applicants have determined that in order to generate a fluid mist effective to address a fire growth using the preferred atomizers, an appropriately configured supply of liquid at the atomizer inlet in view of the inlet supply of gas is required. Preferably, the liquid pressure at the liquid inlet of the preferred atomizer is about 0.5 bar (7 psi.) and at a flow rate of about 1-4 gpm, such as e.g., about 3 gpm or about 3.8 lpm to about 7.61 lpm (1-2 gpm). More preferably, the performance of a preferred water mist system and the characteristics of the fluid mist to be discharged are a function of the mass flow ratio of liquid to gas. More specifically, the applicants have determined that the preferred atomizers 130 provide an effective liquid mist where the fluids at the inlet of the atomizer 130 provide a liquid to gas mass flow ratio within the range of about 1:1 to about 3:1, and more preferably from about 1.75:1 to about 2.25:1 to about 2.5:1 for a given inlet mass flow or pressure of gas to the atomizing device. Because such a ratio can be defined by one fluid as a function of the other, the atomizer performance and therefore the fire fighting performance of the system can be determined by the inlet characteristics of at least one fluid, preferably the gas.

Alternatively, system design and performance can be a function of room size. For example, one preferred embodiment of the mist system provides for discharging at least one of a minimum and maximum volume of liquid mist, measured in liters (L) (gallons (gal.)), to address a fire in the enclosed space 120. In one particular embodiment of the preferred mist system a volume of liquid mist discharge ranges from a minimum of about 22.7 liters (6 gal.) of liquid to about 57 liters (15 gal.) for fire protection of an enclosed space 120 having a volume of about 260 cu. m. (9180 cu. ft.). The method further defines for fire protection of an enclosed space 120 having a volume of about 130 cubic meter (cu. m.) (4590 cu. ft.) with a volume of liquid mist discharge ranging from a minimum of 11.4 liters (3 gal.) of liquid to about 28.4 liters (7.5 gal.) for the same concentration of droplets. In one preferred aspect, a total liquid supply volume of a preferred system preferably ranges from fifty-seven liters (57 L.) (fifteen gallons (15 gal.)) to about ninety-five liters (95 L.) (twenty-five gallons (25 gal.)) for each 130 cu. m. (4590 cu. ft.) of enclosed space.

Although the preferred mist systems are sized for a minimum total discharge time, preferably about ten minute, the system can be alternatively sized to provide a minimum total discharge volume of liquid mist as a function of anticipated fire size in the enclosed space to be protected. For example, a preferred system design can provide a total discharging liquid volume of mist to extinguish a fire for a given unit of enclosure volume, the extinguishment volume, measured in liters per cubic meter (l./cu. m.) (gallons per cubic foot (gal./cu. ft.). Preferably, the total extinguishing volume of the liquid mist is less than about eight gallons (8 gal.) per each 130 cu. m. (4590 cu. ft.) of enclosed space. More preferably the total extinguishing volume of the system ranges from 0.57 liters per cubic meter (0.57 liters/cu. m.) (0.0042 gallons per cubic foot (0.0042 gal./cu. ft.)) to 0.057 liters per cubic meter (0.057 liters/cu. m.) (0.00042 gallons per cubic foot (0.00042 gal./cu. ft.)) for a normalized range of fire sizes ranging from about one (1 kW/$m^3$) to about eight (8 kW/$m^3$).

Because the preferred design and method of operation of the preferred systems can provide for a total volume to extinguish a fire, the preferred system parameters can further define a range of times to extinguishment for a range of normalized fire sizes. In one aspect of the preferred method, the extinguishing times for a preferred system ranges from about 780 seconds to about 80 seconds, preferably from about 500 seconds to about 80 seconds, and more preferably from about 420 seconds to about 80 seconds, for a normalized range of fire sizes ranging, from about 1 kW/cu. m. to about 8 kW/cu. m.

Performance & Scalability

Three of the preferred mist systems described above were tested under various fire challenges in an enclosed space 120 measuring 7.72 m. (25.3 ft.) (long) by 6.55 m. (21.5 ft.) (wide) by 5.1 (16.8 ft.) (tall) for a volume V of about 260 cu. m. (9180 cu. ft.) With reference back to FIGS. 3A-3C the following systems: (i) mist system 300' having two ceiling mounted atomizers 330'; (ii) mist systems 300" having two sidewall mounted atomizers 330"; and (iii) mist system 400' with a single ceiling mounted atomizers 430'. The atomizers of each system were located in a preferred manner as described above, with the ceiling mounted atomizers at a minimum clearance of about 1.2 m. (4 ft.) from the enclosure wall, and the sidewall atomizers located on the short walls to maximize its discharge distance.

Each of the systems was tested with a heptane fuel fire in which heat release rate (HRR) is varied as follow: 250 kW, 500 kW, 1000 kW and 2000 kW. For each fire scenario, the fuel was located in a circular pan with a diameter that varied with the amount of fuel, Dia. (cm.)/Amt of Fuel (liters), as follows: 45 cm./(16 liters) for the HRR of 250 kW; 62 cm./(30 liters) for the HRR of 500 kW; 79 cm./(24.5 liters) for the HRR of 1000 kW; and 112 cm./(49 liters) for the HRR of 2000 kW. For each of the 1000 kW and 2000 KW fire, equal parts water was added to the fuel. The test fires were located on the floor in the geometric center of the enclosed space, underneath a (2.0 m.×2.0 m.) steel table obstruction, with the obstruction about 0.7 m. above the circular pan of fuel. Additionally, each fire was allowed to burn (pre-burn) for a predetermined period of time before the water mist suppression system was turned on. The 250 kW and 500 kW fires were allowed to pre-burn for 120 seconds, and the 1000 kW and 2000 kW fires were allowed to pre-burn for 30 seconds.

For each fire scenario, each of the two atomizer systems 300', 400' was tested first with a water flow rate to nitrogen gas pressure of 5.7 lpm (1.5 gpm) for 6.9 bar (100 psi.) delivered to each atomizer, and then subsequently tested with a water flow rate to nitrogen gas pressure of about 9.5 lpm (2.5 gpm) for 12.1 bar (175 psi.) deliver to each atomizer. The single atomizer system was tested first with a water flow rate to nitrogen gas pressure of 11.4 lpm (3 gpm) for 13.8 bar (200 psi.) delivered to each atomizer, Each of the systems was tested with a heptane fuel fire by measuring, for a given heat release rate: (i) the system's time to extinguishment; (ii) total mist volume discharge at the time of extinguishment; and (iii) oxygen concentration in the enclosed space 120 at the time of extinguishment.

Summary of Test Results for Two Ceiling Mount Atomizers

| Fire Size HRR [kW] | Normalized Fire Size [kW/cu. m.] | Pressure to Ea. Atomizer [bar (psi.)] | Total Flow Rate From System [lpm (gpm)] | Time To Ext. [sec.] | Final O2 [%] | Total Flow at Ext. [L. (gal.)] |
|---|---|---|---|---|---|---|
| 2000 | 7.69 | 6.9 (100) | 11.4 (3.0) | 111 | 15.4 | 21.2 (5.6) |
| 2000 | 7.69 | 12.1 (175) | 17.8 (4.7) | 111 | 15.5 | 32.9 (8.7) |
| 1000 | 3.85 | 6.9 (100) | 11.4 (3.0) | 374 | 15.7 | 70.8 (18.7) |
| 1000 | 3.85 | 12.1 (175) | 18.2 (4.8) | 216 | 15.4 | 86.3 (22.8) |
| 500 | 1.92 | 6.9 (100) | 11.4 (3.0) | 455 | 15.4 | 86.3 (22.8) |
| 500 | 1.92 | 12.1 (175) | 18.9 (5.0) | 301 | 15.0 | 95.0 (25.1) |
| 250 | 0.96 | 6.9 (100) | 11.4 (3.0) | 1018 | 15.0 | 193 (50.9) |
| 250 | 0.96 | 12.1 (175) | 18.9 (5.0) | 431 | 15.1 | 136 (35.9) |

Summary of Test Results for Two Sidewall Mount Atomizers

| Fire Size HRR [kW] | Normalized Fire Size [kW/cu. m.] | Pressure to Ea. Atomizer [bar (psi.)] | Total Flow Rate From System [lpm (gpm)] | Time To Ext. [sec.] | Final O2 [%] | Total Flow at Ext. [L. (gal.)] |
|---|---|---|---|---|---|---|
| 2000 | 7.69 | 6.9 (100) | 11.4 (3.0) | 82 | 17.0 | 15.5 (4.1) |
| 2000 | 7.69 | 12.1 (175) | 18.9 (5.0) | 85 | 16.0 | 26.9 (7.1) |
| 1000 | 3.85 | 6.9 (100) | 11.4 (3.0) | 224 | 16.8 | 42.4 (11.2) |
| 1000 | 3.85 | 12.1 (175) | 18.9 (5.0) | 164 | 17.0 | 51.9 (13.7) |
| 500 | 1.92 | 6.9 (100) | 11.4 (3.0) | 349 | 16.5 | 66.2 (17.5) |
| 500 | 1.92 | 12.1 (175) | 18.9 (5.0) | 319 | 15.6 | 101 (26.6) |
| 250 | 0.96 | 6.9 (100) | 11.4 (3.0) | 866 | 15.6 | 164 (43.3) |
| 250 | 0.96 | 12.1 (175) | 18.9 (5.0) | 501 | 15.3 | 158 (41.8) |

Summary of Test Results for Single Ceiling Mount Atomizers

| Fire Size HRR kW] | Normalized Fire Size [kW/cu. m.] | Pressure to Ea. Atomizer [bar (psi.)] | Total Flow Rate From System [lpm (gpm)] | Time To Ext. [sec.] | Final O2 [%] | Total Flow at Ext [L. (gal.)] |
|---|---|---|---|---|---|---|
| 2000 | 7.69 | 13.8 (200) | 11.4 (3.0) | 145 | 14.7 | 27.6 (7.3) |
| 1000 | 3.85 | 13.8 (200) | 11.4 (3.0) | 237 | 15.2 | 45.0 (11.9) |

-continued

| Fire Size HRR kW] | Normalized Fire Size [kW/cu. m.] | Pressure to Ea. Atomizer [bar (psi.)] | Total Flow Rate From System [lpm (gpm)] | Time To Ext. [sec.] | Final O2 [%] | Total Flow at Ext [L. (gal.)] |
|---|---|---|---|---|---|---|
| 500 | 1.92 | 13.8 (200) | 11.4 (3.0) | 500 | 16.1 | 94.6 (25.0) |
| 250 | 0.96 | 13.8 (200) | 11.4 (3.0) | 766 | 16.1 | 145 (38.3) |

Successful fire test results demonstrate the capability of the preferred systems and methods described herein to provide effective fire protection. Moreover, the fire tests demonstrate that the system performance is influenced by, e.g., one or more of the input system parameters discussed above.

Figure 9:
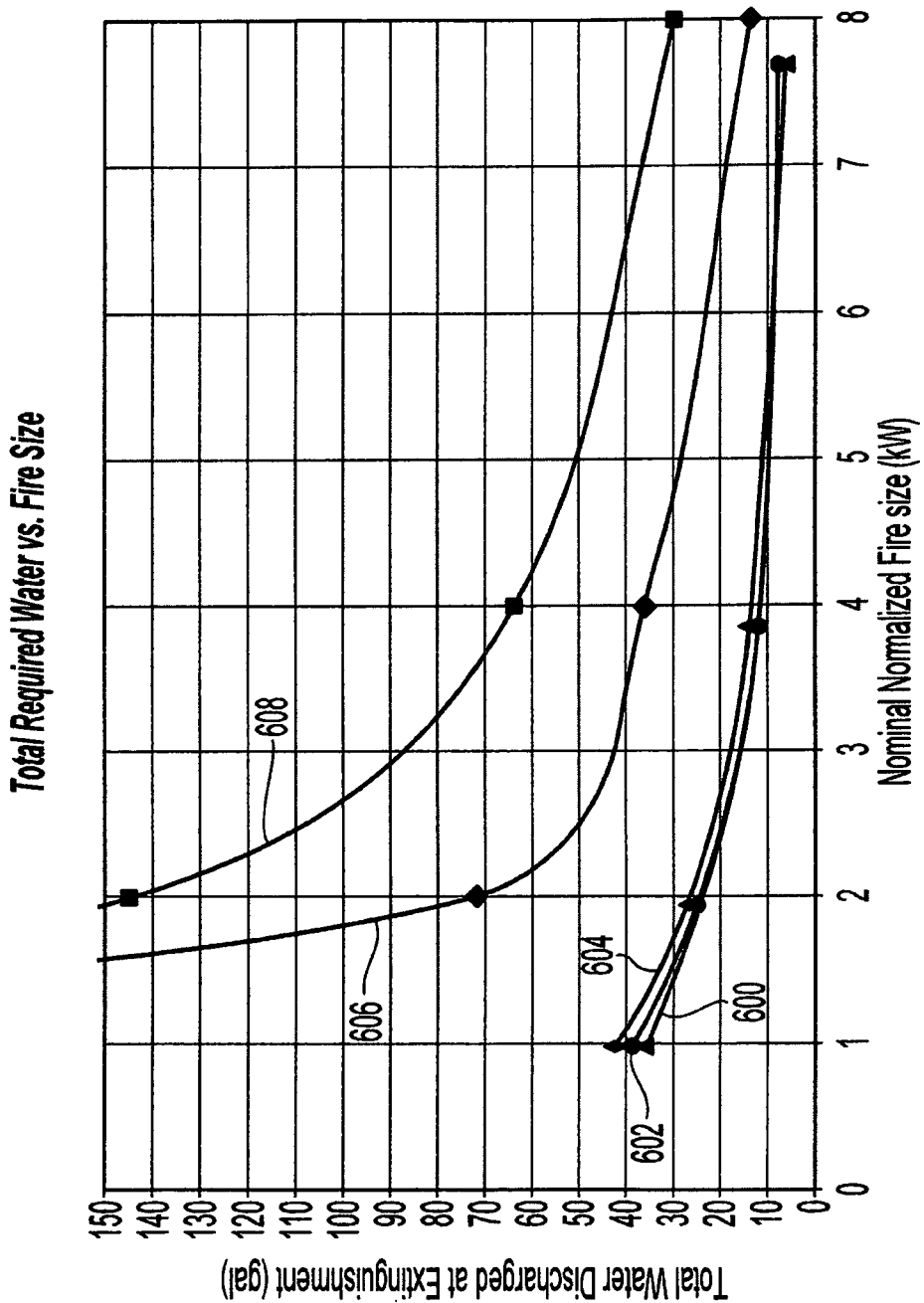
FIG. 9 is a performance plot comparing preferred systems to known systems.

For example, shown in FIG. 9 are three plots for the total water consumption to extinguishment over a range of nominal normalized fire sizes in the preferred systems 300', 300", 400' described above. The normalized fire is the fire size per unit volume of the enclosure measured in kilowatts per cubic meter (kW/cu. m.). Plot 600 shows the water consumption to extinguishment for the preferred system 300' in which two atomizers 330' are ceiling mounted. Plot 602 shows the water consumption to extinguishment for the preferred system 400' in which a single atomizer 430' is ceiling mounted. Plot 604 shows the water consumption to extinguishment for the preferred system 300" in which two atomizers 330" are sidewall mounted.

The three plots 600, 602, 604 are substantially similar over the range of nominal normalized fire sizes. The plots 600, 602, 604 therefore illustrate that the preferred systems and methods provide substantially constant fire protection performance regardless of where or in what manner the atomizers are mounted within the enclosure. More specifically, the plots 600, 602, 604 indicate that a single atomizer system can perform the same as a dual atomizer system, i.e., require substantially the same amount of water to extinguishment, for a common range of nominal fire sizes, preferably ranging from about 1 kW/cu. m. to 8 kW/cu. m. Therefore, it is believed that a preferred system having a single atomizer can perform the same as a system with two atomizers provided their total flow rates are equal. Thus, a system 400' with a single atomizer 430' can be appropriately scaled by discharging liquid at a flow rate of 11.4 lpm (3 gpm) to provide equal fire protection as a system 300', 300" having two atomizers 330', 330" each discharging at a flow rate of 5.7 lpm (1.5 gpm). The other plots 606, 608 respectively show the performance of a known high pressure water mist system and a low pressure water mist system, each of which require a greater amount of water for extinguishment.

Figure 10:
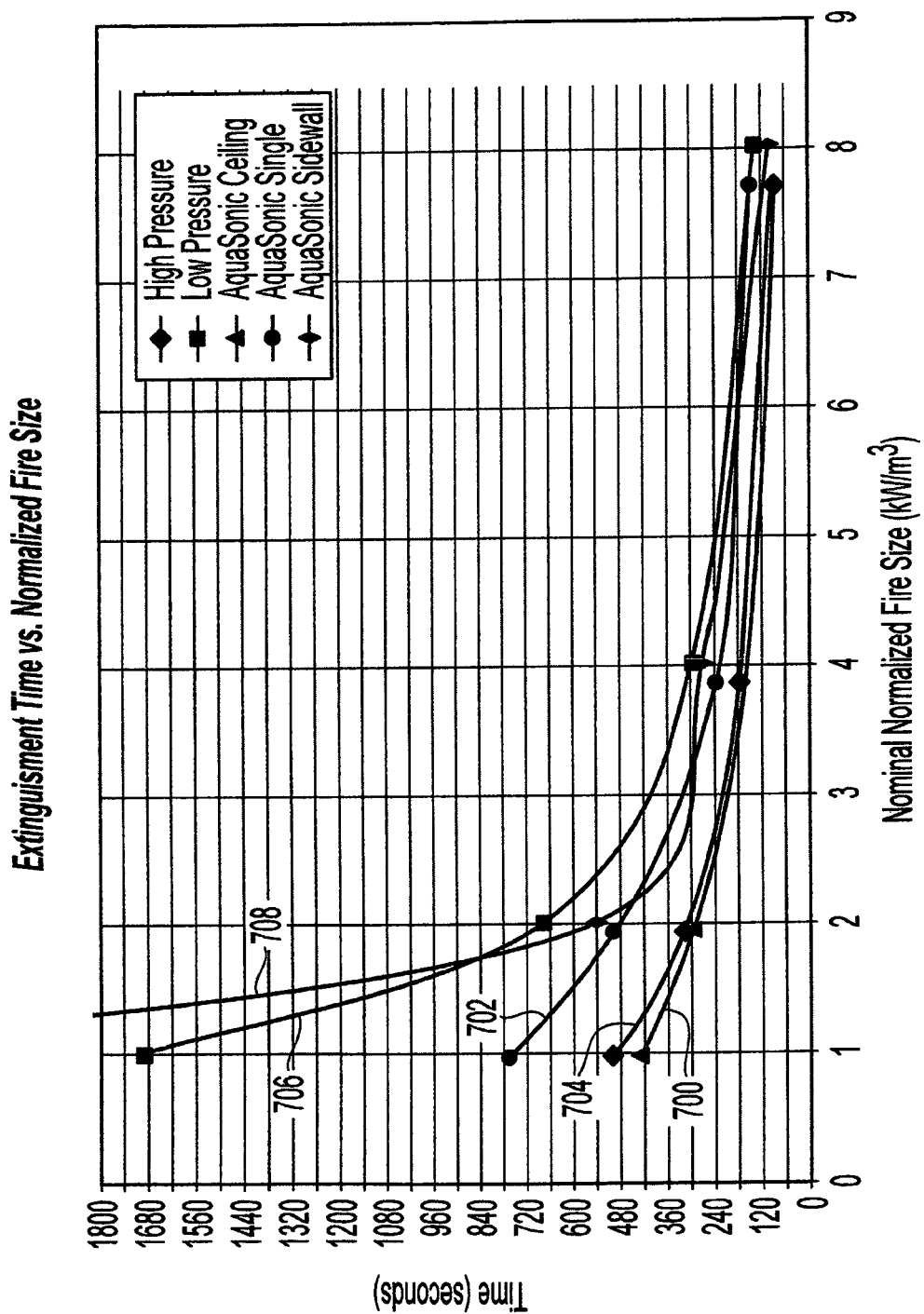
FIG. 10 is another performance plot comparing preferred systems to known systems.

Another set of performance plots 700, 702, 704 is provided at FIG. 10, in which each plot shows the time to extinguishment for a nominal normalized fire heat release rate. Plot 700 shows the time to extinguishment for the preferred system 300' in which two atomizers 330' are ceiling mounted. Plot 702 shows the time to extinguishment for the preferred system 400' in which a single atomizer 430' is ceiling mounted. Plot 704 shows the time to extinguishment for the preferred system 300" in which two atomizers 330" are sidewall mounted. The other plots 706, 708 of FIG. 10 show the time to extinguishment respectively for a known high pressure mist system and a low pressure mist system. The plots 700, 702, 704 for the preferred systems substantially converge for a normalized fire size of about 8 kW/cu. m. and only vary relatively slightly as the normalized fire size decreases. Again, the plots 700, 702, 704 demonstrate that the preferred systems can be configured to provide substantially the same fire protection performance, i.e., time to extinguishment, independent of the mounting orientation and/or location of the atomizers within the enclosure being protected. Moreover, the plots illustrate substantially equal performance from single atomizer as compared to a system with two atomizers provided each system has a substantially constant or equivalent total volume of discharge into the volume. At the lower range of normalized fire sizes, the plots illustrate the ability of the preferred systems 300', 300", 400' to have a shorter time to extinguishment when compared to either the known high pressure water mist system or a low pressure mist system.

Additional tests were conducted to demonstrate the scalability of the preferred systems to provide mist fire protection to larger enclosed systems beyond 260 cu. m. (9180 cu. ft.) In particular, fire tests were conducted to evaluate the performance of the preferred water mist system in an enclosed space measuring 13 m. (42.5 ft.) long by 10. m. (32.8 ft.) wide by 8.0 m. (26.2 ft.) tall for a volume V of about 1040 cu. m. (36,700 cu. ft.) with a ventilation opening of 4 sq. m. on one of the two shorter walls. Ceiling mounted atomizers in a pendent orientation were utilized for all tests. The performance of the two pendent atomizer system 300' for the 260 cu. m. (9180 cu. ft.) enclosure, in which each atomizer was provided with 6.9 bar (100 psi.) of gas pressure and a water flow rate of 5.7 lpm (1.5 gpm) corresponding to a total system flow rate of 11.4 lpm (3 gpm), was used as a comparative basis in order to evaluate the performance of a larger enclosure system.

A test fire with a nominal heat release rate of 2000 kW was utilized for all tests. For each fire, 38 liters (10 gallons) of heptane fuel and approximately 38 liters (10 gallons) of water was located in a circular pan with a diameter of 112 cm. The test fires were located on the floor in the geometric center of the enclosed space, underneath a (2.0 m.×2.0 m.) steel table obstruction, with the obstruction about 0.7 m. above the circular pan of fuel. Each test fire was allowed to pre-burn for 30 seconds prior to initiation of the mist suppression system.

Three tests were conducted on a preferred water mist system configured for the protection of an enclosed spaced having a free volume of 1040 cu. m. (36,700 cu. ft.), four times the volume of the base enclosure 260 cu. m. (9180 cu. ft.). In each test, a system parameter was varied and the performance of the system measured to evaluate the scalability of the preferred water mist systems with respect to the varied parameter.

In the first test, Test 1, the number of atomizers was increased proportionally to the room size. Accordingly, with the free volume increased four times, test 1 increased the number of atomizers from two (2) to a total of eight (8) atomizers. The atomizers were installed in an evenly spaced grid pattern on the enclosure ceiling which consisted of two rows of four atomizers nominally 5.0 m. (16.4 ft.) by 3.25 m (10.7 ft.) apart. The flow rate to each atomizer was held at the constant rate of 5.7 lpm (1.5 gpm) and the operating gas pressure was held at 6.9 bar (100 psi.) Accordingly, the system of Test 1 provided for a total system flow of 45.4 lpm (12 gpm).

In the second test, Test 2, the number of atomizers was increased from two (2) to a total of four (4) atomizers. The eight (8) atomizers utilized in test 1 were left in their original installation location, but the fluid supply to every other atomizer was shut off, resulting in the stated total of four (4) functional atomizers in a staggered pattern. The flow rate to each atomizer was held at the constant rate of 5.7 lpm (1.5 gpm) and the operating gas pressure was held at 6.9 bar (100 psi.) Accordingly, the system of Test 2 provided for a total system flow of 22.7 lpm (6 gpm).

In the third test, Test 3, the test system was again provided with the same four functional atomizers utilized in test 2, but this time the flow rate to each was increased. More specifically, the flow rate of water to each atomizer was doubled from 5.7 lpm (1.5 gpm) to 11.4 lpm (3 gpm). The gas pressure to each atomizer was also doubled from 6.9 bar (100 psi.) to 13.8 bar (200 psi.). Accordingly, the system of Test 3 provided for a total system flow of 45.4 lpm (12 gpm.).

For each test set up, a 2 kW fire was addressed and extinguished by the test system. The time to extinguishment for each system was recorded along with the total water discharged at the time of extinguishment. The final oxygen concentration in the room at the time of extinguishment was also recorded. The system of Test 1 was tested twice; once with the 1040 cu. m. (36,700 cu. ft.) enclosure space vented through a 4.0 square meter (43.1 sq. ft.) ventilation opening and once with the enclosure space not vented. Results of the tests is provided below:

Summary of Results for Ceiling Mounted Atomizers in a 1040 cu. m. Enclosure

The overall time to extinguishment marginally increased while the total quantity of water required to extinguish the fire significantly decreased when the total water flow rate was reduced from 45.4 liters (12 gallons per minute) to 22.7 liters per minute (6 gallons per minute), the number of discharging atomizers was reduced from 8 to 4, and nitrogen pressure was held constant at 6.9 bar (100 psi.)

When tested in the 1040 cubic meter (36,700 cu. ft.) enclosure, the system demonstrated nearly identical performance when tested with 8 atomizers set at 5.7 liters (1.5 gallons per minute) each water flow and 6.9 bar (100 psi) nitrogen pressure, and 4 atomizers set at 11.4 liters per minute (3.0 gallons per minute) each water flow and 13.8 bar (200 psi) nitrogen pressure. These settings corresponded to a water-to-gas mass flow ratio of approximately 2.25:1. Extinguishment times at 200 psi nitrogen pressure were marginally shorter than those observed at 6.9 bar (100 psi) nitrogen pressure. This suggests that overall turbulence increases as a result of the increase in spray plume velocity at increased gas pressures.

Closing off the 4 square meter ventilation opening resulted in an increase of approximately 25-50% in performance (as defined by time to extinguishment and total water discharged at extinguishment). The compressed nitrogen utilized to atomize the water appeared to maintain a higher pressure within the enclosure with respect to the external environment, subsequently reducing the quantity of fresh air which was drawn through the ventilation opening. It is surmised that ventilation effects can be significantly reduced if not eliminated by pressurizing an enclosure with a high enough introduction rate of inert gas such as nitrogen into the space.

| Fire Size HRR [kW] | Normalized Fire Size [kW/cu. m.] | Qty of Atomizers | Pressure to Ea. Atomizer [bar (psi.)] | Total Flow Rate From System [lpm (gpm)] | Time To Ext. [sec.] | Final O2 [%] | Total Flow at Ext. [L. (gal.)] |
|---|---|---|---|---|---|---|---|
| 2000 | 1.9 | 8 | 6.9 (100) | 45.4 (12.0) | 390 | 15.0 | 295 (78.0) |
| 2000 | 1.9 | 8 | 6.9 (100) | 45.4 (12.0) | 390 | 15.0 | 295 (78.0) |
| 2000 | 1.9 | 8 | 6.9 (100) | 45.4 (12.0) | 253 | 15.4 | 192 (50.6) |
| 2000 | 1.9 | 4 | 6.9 (100) | 22.7 (6.0) | 430 | 15.4 | 163 (43.0) |
| 2000 | 1.9 | 4 | 6.9 (100) | 22.7 (6.0) | 459 | 15.2 | 174 (45.9) |
| 2000 | 1.9 | 4 | 6.9 (100) | 22.7 (6.0) | 344 | 15.0 | 130 (34.4) |
| 2000 | 1.9 | 4 | 6.9 (100) | 22.7 (6.0) | 348 | 15.0 | 132 (34.8) |
| 2000 | 1.9 | 4 | 10 (145) | 30.3 (8.0) | 353 | 15.0 | 178 (47.1) |
| 2000 | 1.9 | 4 | 13.8 (200) | 45.4 (12.0) | 381 | 14.8 | 288 (76.2) |
| 2000 | 1.9 | 4 | 13.8 (200) | 45.4 (12.0) | 193 | 14.8 | 146 (38.6) |

From the test results, the applicants have concluded that a 1040 cubic meter (36,700 cu. ft.) enclosure with a 4 square meter (43.1 sq. ft.) ventilation opening can be protected with at least as few as 4 total atomizers and an overall water flow rate of 22.7 lpm (6 gallons per minute). The high velocity spray plume of the atomizer generates a significant amount of turbulence, rapidly filling the protected space with water mist. As a result, fire extinguishment performance appears to be independent of both the number of devices utilized, and their overall orientation within the compartment.

The overall results of the testing in the 1040 cubic meter (36,700 cu. ft.) enclosure were consistent with those of the testing in the 260 cubic meter (9180 cu. ft.) enclosure for a constant normalized fire size. This suggests that the extinguishing performance of the system remains constant as long as the water-to-gas mass flow ratio is held constant, and the total flow rate of water discharged into the protected space is scaled linearly with enclosure volume.

FM Testing

The above referenced fire tests were conducted in accordance with Factory Mutual Global ("FM Global") Standard 5560 (May 2005), Appendices D, E, and F, at pages 127 to page 146. Copies of the FM Standard 5560 and the three test protocols are attached to U.S. Provisional Patent Application No. 60/989,083 and are incorporated by reference in their entireties. Fire tests can be conducted in accordance with alternate standards such as, for example, IMO, VDS, UL, CCCF, etc. More specifically, fire tests were conducted to illustrate the effectiveness of the preferred method in providing water mist fire protection for: (i) Machinery Spaces; (ii) Special Hazard Machinery Spaces; and (iii) Combustion Turbine Enclosures. The three test protocols provide for each one of (i) a diesel and a heptane fuel test, (ii) a total of five fire tests for machinery spaces and (iii) seven tests for insulated combustion turbines. Preferably, the diesel fuel is high flash point diesel used preferably in normal hazard and combustion turbines, and the heptane fuel is of a low flash point special hazard type. Each of the fires tested ranged between about 1 megawatt to just over 2 megawatt (1-2 MW) and was configured as any one of a small shielded fuel spray fire, a soaked insulation matt fire, a ventilated fuel fire, a pool fire and a pan fire.

Each of the fire test scenarios was conducted using two preferred two atomizer mist system 300' and single atomizer mist system 400'. The first preferred system 300' having two atomizers 330" was evaluated in a 260 cubic meter (9180 cu. ft.) enclosed space 120 measuring generally 6.6 m. (21.6 ft.) wide by 7.7 m. (25.3 ft.) long by 5.1 m. (16.8 ft.) high, and the second preferred system 400 having a single atomizer 430 was evaluated in a 130 cu. m. (4590 cu. ft.) enclosure measuring generally 6.6 m. (21.6 ft.). wide by 3.9 m. (12.8 ft.) long by 5.1 m. (16.8 ft.) high. In accordance with the FM test requirements, the enclosed space included a personnel door, preferably (0.81 m. (2.7 ft.)×2.03 m. (6.7 ft.)), located 2.7 m. (9 ft.) from one of the enclosure corners. Along one of the long walls of the enclosure, a preferably removable panel (1.22 m. (4.0 ft.)×2.44 m. (8.0 ft.) is provided to provide enclosure access. The enclosed spaced 120 further included two hinged ceiling hatches (0.91 m. (3.0 ft.)×1.83 m. (6.0 ft.)) in opposite diagonal corners to provide heat and smoke release at the conclusion of the test.

Each of the systems 300', 400' was constructed and tested with its atomizers 330', 430' initially ceiling mounted and then subsequently tested with the atomizers sidewall mounted 300", 400". For each fire test, the atomizers 330', 430' were provided with a flow of water at about 11.4 liters per minute (3 gpm) and a gas flow rate of 4.6 kg/min (150 scfm) at an operating pressure of about 6.9 bar (100 psi.). The total water mist discharge time from the systems was about 10 minutes.

According to the fire test results for each of the preferred systems 300' and 400,' extinguishment of the test fire was achieved in less than five minutes with an end concentration of oxygen per volume within the enclosure space at or above fifteen percent by volume.

According to Appendix D of FM 5560, five tests are conducted: D1) an unshielded 1 MW diesel spray fire; D2) a shielded 1 MW diesel spray fire; D3) a diesel pool fire; D4) a shielded 2 MW diesel spray fire with limited natural ventilation; and D5) a shielded 2 MW diesel spray fire at the smaller enclosure volume.

Summary of FM Appendix D Test Results

| Class 5560 Test Number | Qty. of Nozzles | Nozzle Spacing ft. [m] | Water Flow Rate [gpm (lpm)] | Nitrogen pressure [bar (psi)] | Estimated Fire Size [kW] | Ext. Time [sec] | Total Water at Ext [liters (gal)] | Total Mass Density % Ext. (g/m$^3$) |
|---|---|---|---|---|---|---|---|---|
| D.3.1 | 2 | 9.5 × 13.5 (2.9 × 4.1) | 5.7 (1.5) | 6.9 (100) | 1000 | 145 | 27.4 (7.25) | 105.19 |
| D.3.2 | 2 | 9.5 × 13.5 (2.9 × 4.1) | 5.7 (1.5) | 6.9 (100) | 1000 | 225 | 42.6 (11.25) | 163.23 |
| D.3.2 | 2 | 13.5 × 17.5 (4.1 × 5.3) | 5.7 (1.5) | 6.9 (100) | 1000 | 153 | 29.0 (7.65) | 111.00 |
| D.3.3 | 2 | 9.5 × 13.5 (2.9 × 4.1) | 5.7 (1.5) | 6.9 (100) | 1541 | 145 | 27.4 (7.25) | 105.19 |
| D.3.4 | 2 | 9.5 × 13.5 (2.9 × 4.1) | 5.7 (1.5) | 6.9 (100) | 2000 | 223 | 42.2 (11.15) | 161.78 |
| D.3.5 | 1 | — | 5.7 (1.5) | 6.9 (100) | 2000 | 105 | 19.9 (5.25) | 152.35 |

According to Appendix E of FM 5560, five tests are conducted: E1) an unshielded 1 MW Heptane spray fire; E2) a shielded 1 MW Heptane spray fire; E3) a shielded 10.8 cu. ft. (1 cu. m.) Heptane Pool Fire; E4) a shielded 2 MW Heptane spray fire with limited natural ventilation; and E5) a shielded 2 MW diesel spray fire at the smaller enclosure volume.

Summary of FM Appendix E Test Results

| Class 5560 Test Number | Qty. of Nozzles | Nozzle Spacing ft. [m] | Water Flow Rate [gpm (lpm)] | Nitrogen pressure [bar (psi)] | Estimated Fire Size [kW] | Ext. Time [sec] | Total Water at Ext [liters (gal)] | Total Mass Density % Ext. (g/m$^3$) |
|---|---|---|---|---|---|---|---|---|
| E.3.1 | 2 | 9.5 × 13.5 (2.9 × 4.1) | 5.7 (1.5) | 6.9 (100) | 1000 | 196 | 37.1 (9.8) | 284.38 |
| E.3.2 | 2 | 9.5 × 13.5 (2.9 × 4.1) | 5.7 (1.5) | 6.9 (100) | 1000 | 208 | 39.4 (10.4) | 301.80 |
| E.3.3 | 2 | 9.5 × 13.5 (2.9 × 4.1) | 5.7 (1.5) | 6.9 (100) | 2900 | 133 | 25.2 (6.65) | 192.97 |
| E.3.4 | 2 | 9.5 × 13.5 (2.9 × 4.1) | 5.7 (1.5) | 6.9 (100) | 2000 | 204 | 38.6 (10.2) | 295.99 |
| E.3.4 | 2 | 13.5 × 17.5 (4.1 × 5.3) | 5.7 (1.5) | 6.9 (100) | 2000 | 203 | 38.6 (10.2) | 294.54 |
| E.3.5 | 1 | — | 5.7 (1.5) | 6.9 (100) | 2000 | 105 | 19.9 (5.25) | 152.35 |

According to Appendix F of FM 5560, five tests are conducted: F1) an unshielded 1 MW diesel spray fire; F2) a shielded 1 MW diesel spray fire; F3) a shielded 10.8 cu. ft. (1 cu. m.) diesel Pool Fire; F4) a shielded 2 MW diesel spray fire with limited natural ventilation; and F5) a shielded 2 MW diesel spray fire at the smaller enclosure volume; F7) a saturated insulation mat and spray fire; and F8) a large saturated insulation mat.

Summary of FM Appendix F Test Results booths; (xiii) engine test cells, (xiv) solvent handling cells; and (xv) flammable liquid storerooms.

The preferred systems and methods have a demonstrated ability to provide effective fire protection more efficiently than known water mist systems or conventional water spray or sprinkler systems. In particular, the table below illustrates that the preferred method and system of fire protection provides effective fire protection with at least one of (i) less

| Class 5560 Test Number | Qty. of Nozzles | Nozzle Orientation | Nozzle Spacing ft. [m] | Water Flow Rate [gpm (lpm)] | Nitrogen pressure [bar (psi)] | Estimated Fire Size [kW] | Ext. Time [sec] | Total Water at Ext [liters (gal)] | Total Mass Density % Ext. $(g/m^3)$ |
|---|---|---|---|---|---|---|---|---|---|
| F.3.1 | 2 | Ceiling | 9.5 × 13.5 (2.9 × 4.1) | 5.7 (1.5) | 6.9 (100) | 1000 | 145 | 27.4 (7.25) | 105.19 |
| F.3.2 | 2 | Ceiling | 9.5 × 13.5 (2.9 × 4.1) | 5.7 (1.5) | 6.9 (100) | 1000 | 225 | 42.6 (11.25) | 163.23 |
| F.3.2 | 2 | Ceiling | 13.5 × 17.5 (4.1 × 5.3) | 5.7 (1.5) | 6.9 (100) | 1000 | 153 | 29.0 (7.65) | 111.00 |
| F.3.3 | 2 | Ceiling | 9.5 × 13.5 (2.9 × 4.1) | 5.7 (1.5) | 6.9 (100) | 1541 | 145 | 27.4 (7.25) | 105.19 |
| F.3.4 | 2 | Ceiling | 9.5 × 13.5 (2.9 × 4.1) | 5.7 (1.5) | 6.9 (100) | 2000 | 223 | 42.4 (11.15) | 161.78 |
| F.3.5 | 1 | Ceiling | — | 5.7 (1.5) | 6.9 (100) | 2000 | 105 | 19.9 (5.25) | 152.35 |
| F.3.1 | 2 | Sidewall | 14.9 × 25.5 (4.6 × 6.6) | 5.7 (1.5) | 6.9 (100) | 1000 | 242 | 45.8 (12.1) | 175.56 |
| F.3.2 | 2 | Sidewall | 14.9 × 25.5 (4.6 × 6.6) | 5.7 (1.5) | 6.9 (100) | 1000 | 214 | 40.5 (10.7) | 155.25 |
| F.3.3 | 2 | Sidewall | 14.9 × 25.5 (4.6 × 6.6) | 5.7 (1.5) | 6.9 (100) | 1541 | 242 | 45.8 (12.1) | 175.56 |
| F.3.4 | 2 | Sidewall | 14.9 × 25.5 (4.6 × 6.6) | 6.6 (1.75) | 7.6 (110) | 2000 | 147 | 27.8 (7.35) | 106.64 |
| F.3.5 | 1 | Sidewall | — | 5.7 (1.5) | 6.9 (100) | 2000 | 255 | 48.3 (12.75) | 369.99 |
| F.3.7 | 2 | Ceiling | 9.5 × 13.5 (2.9 × 4.1) | 5.7 (1.5) | 6.9 (100) | 1100 | 183 | 34.6 (9.15) | 265.52 |
| F.3.7 | 2 | Sidewall | 14.9 × 25.5 (4.6 × 6.6) | 5.7 (1.5) | 6.9 (100) | 1100 | 197 | 37.3 (9.85) | 285.83 |
| F.3.8 | 2 | Ceiling | 9.5 × 13.5 (2.9 × 4.1) | 5.7 (1.5) | 6.9 (100) | 1541 | 279 | 52.8 (13.95) | 404.81 |
| F.3.8 | 2 | Ceiling | 13.5 × 17.5 (4.1 × 5.3) | 5.7 (1.5) | 6.9 (100) | 1541 | 240 | 45.4 (12.0) | 348.23 |
| F.3.8 | 2 | Sidewall | 14.9 × 25.5 (4.6 × 6.6) | 5.7 (1.5) | 6.9 (100) | 1541 | 257 | 48.6 (12.85) | 372.89 |

Because of the successful test results, the preferred systems and methods are believed to provide industrial fire protection in enclosed spaces at least up one thousand forty cubic meters (1040 cu. m.) for special hazard applications including, but not limited to: (i) oil pumps and tanks; (ii) fuel filters; (iii) generators; (iv) transformer vaults; (v) diesel driven generators; (vi) gear boxes; (vii) drive shafts; (viii) lubrication skids; (ix) combustion turbines; (x) internal combustion engines; (xi) hydraulic power packs; (xii) paint water; and (ii) at lower pressure; when compared to known high or low pressure water mist systems. Table 1 below shows respectively the total water consumption required and the corresponding pressure required for total flooding extinguishment of a nominal 1 MW fire for each of the preferred water mist system, a known high pressure mist system, and a known low pressure mist system.

| | Test Data - (Sealed Compartment Data Only) | | | | | |
|---|---|---|---|---|---|---|
| | Min. | | Water Consumption [liters (gallons)] | | | |
| System | Operating Pressure [bar (psi)] | Ref. Flow Rate [lpm (gpm)] | 1 $kW/m^3$ (97 $BTU/ft^3$ hr) | 2 $kW/m^3$ (194 $BTU/ft^3$ hr) | 4 $kW/m^3$ (388 $BTU/ft^3$ hr) | 8 $kW/m^3$ (776 $BTU/ft^3$ hr) |
| Preferred System 300, 400* | 6.9 (100) | 11.4 (3.0) | 164 (43.3) | 66.2 (17.5) | 42 (11.2) | 15.5 (4.1) |
| Known High Pressure Mist (HI-FOG ®) | 80 (1160) | 30 (7.9) | 1305 (345) | 270 (71.3) | 135 (36) | 50 (13.2) |
| Known Low Pressure Mist (AQUAMIST ® from TYCO FIRE PRODUCTS LP) | 12.4 (180) | 48.5 (12.8) | 1358 (359) | 548 (145) | 242.5 (64) | 111.5 (29.5) |

Test Data - (Sealed Compartment Data Only)

| System | Min. Operating Pressure [bar (psi)] | Ref. Flow Rate [lpm(gpm)] | Extinguishment Time [seconds] | | | |
|---|---|---|---|---|---|---|
| | | | 1 kW/m$^3$ (97 BTU/ft$^3$ hr) | 2 kW/m$^3$ (194 BTU/ft$^3$ hr) | 4 kW/m$^3$ (388 BTU/ft$^3$ hr) | 8 kW/m$^3$ (776 BTU/ft$^3$ hr) |
| Preferred System 300, 400* | 6.9 (100) | 11.4 (3.0) | 866 | 349 | 224 | 82 |
| Known High Pressure Mist (HI-FOG ®) | 80 (1160) | 30 (7.9) | 2630 | 542 | 270 | 100 |
| Known Low Pressure Mist (AQUAMIST ® from TYCO FIRE PRODUCTS LP) | 12.4 (180) | 48.5 (12.8) | 1691 | 678 | 298 | 137 |

*System tested in a slightly larger compartment than referenced High Pressure and Low Pressure systems.

A Preferred Atomizing Device

One preferred atomizer 1000 for use in the above water mist systems is shown in FIGS. 11, 13, 14 and 15. The atomizer 1000 is a twin fluid mist generating device having a first fluid passage 1080 and a second fluid passage 1090. The first and second fluid passages 1080, 1090 of the atomizer 1000 are defined by the manner in which the components of the device interconnect and interrelate with one another. The components of the atomizer 1000 generally include: a base 1012, a funnel 1030, a plug 1050 and a cover 1070.

The base 1012 is preferably a generally circular member having a rear face 1014, a front face 1016 and first and second fluid inlet passages 1018, 1020 adapted to receive respectively the liquid and gas from their respective fluid supply sources (not shown). Each of the fluid inlet passages 1018, 1020 is substantially parallel with the longitudinal axis L of the apparatus. Extending longitudinally through the centre of the base 1012 is a bore 1017.

The funnel 1030 is engaged with the base 1012 so that the base 1012 and the funnel 1030 are concentrically disposed about the longitudinal axis L. The funnel 1030 has a first end 1044, a second end 1042 and a bore 1046 extending longitudinally through the funnel 1030 from the first end 1044 to the second end 1042 to generally define the second fluid passage 1090. The bore 1046 has an inlet 1047 at the first end 1044, an outlet 1048 at the second end 1042, and a throat portion 1049 intermediate the inlet 1047 and the outlet 1048. At the inlet 1047 the bore 1046 has a diameter D1, at the throat portion 1049 the diameter of the bore 1046 is D2, and at the outlet 1048 the diameter of the bore is D3. The diameter D1 at the inlet 1047 is greater than the diameter D2 or D3, whilst the diameter D2 at the throat portion 1049 is less than the diameters D1 and D3. As a result, the bore 1046 narrows from its widest point at the inlet 1047 to a narrow diameter at the throat portion 1049 before widening again until it reaches the outlet 1048. The funnel 1030 is preferably formed as a single piece member having a radially extending flange portion 1032 and an axially projecting body portion 1034. The body portion 1034 has an outer surface 1037. An annular lip portion 1031 extends rearwards from the flange portion 1032 defining a first fluid passage 1038 and an inspection port 1039.

The plug 1050 is an elongate member having a first end 1051 and a second end 1052. The plug 1050 has a first generally cylindrical portion 1053 and a second conical portion 1055 extending from, and preferably integrally formed with, the cylindrical portion 1053. The conical portion 1055 has a smallest diameter D4 adjacent the cylindrical portion 1053 and its largest diameter D5 at the second end 1052 of the plug 1050. The plug 1050 is engaged with the base 1012 such that the conical portion 1055 of the plug 1050 provides a solid protrusion disposed in the bore 1046 of the funnel 1030. More specifically, the inner surface of the bore 1046 and outer surface of the plug 1050 define a preferred configuration of the second fluid passage 1090.

The inlet 1047 of the funnel bore 1046 acts as the inlet of the second fluid passage 1090. The second fluid passage 1090 further includes a throat portion 1092 adjacent the throat 1049 of the bore 1046 of the funnel, and an outlet 1094 adjacent the respective second ends 1042, 1052 of the funnel 1030 and plug 1050. As a result of the previously mentioned variations in the diameter of the bore 1046 and the outward taper of the conical portion 1055 of the plug 1050, the second fluid passage 1090 has a convergent-divergent internal geometry. In other words, the cross-sectional area of the throat portion 1092 of the passage 1090 is considerably smaller than that of the inlet 1047 and the outlet 1094. The cross sectional area of the passage 1090 at the outlet 1094 is preferably greater than that at the throat portion 1092, but less than that at the inlet 1047. The total volume of the second fluid passage 1090 from inlet 1047 to outlet 1094 may be about 24,900 cu. mm. and is more preferably between 24.3 cu. cm. (1.48 cu. in.) and 25.500 cu. cm (1.56 cu. in.).

Figure 21:
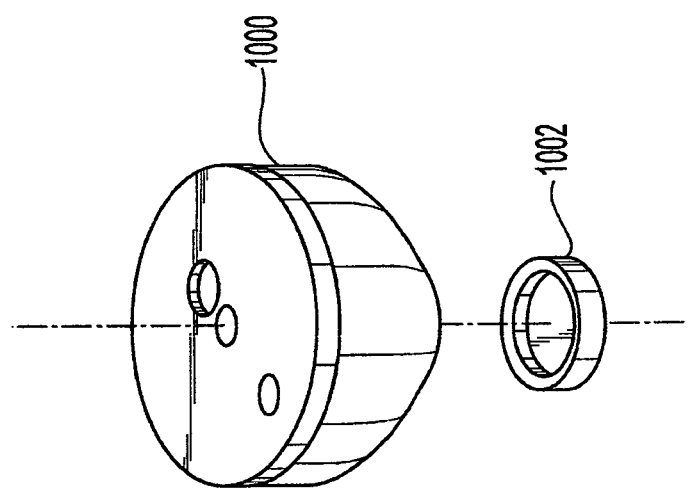
FIG. 21 is an exploded view of the atomizer of FIG. 11 and a protective cap.

The cover 1070 is axially placed on the base 1012 such that the cover is then concentric with the other components about the axis L. The cover 1070 is generally dome-shaped, having a first end 1072 of larger diameter than a second end 1074. Projecting axially from the second end 1074 of the cover 1070 is an annular lip 1076. Referring to FIG. 21, the lip 1076 forms an outer surface to the cover 1070 over which a dust cap 1002 or other protective covering that can be secured to prevent contaminant from entering the atomizer through the discharge space 508 when the system is in a non-actuated state. As discussed above, the cover 1002 is disposed about the lip 1076 such that the discharge fluids from the atomizer dislodge the dust cap 1002 from the lip 1076.

Referring back to FIG. 16, the lip 1076 has an internal surface 1078 which defines a chamber or bore of substantially constant diameter. The cover 1070 has a first section adjacent the first end 1072 which has a first inner surface 1073 of substantially constant diameter. A second section of the cover 1070 extending between the first section and the lip 1076 has a second inner surface 1075. The diameter of the second section reduces in the direction of the second end 1074. More preferably, the second inner surface 1075 has a smooth inwardly curving profile as it progresses towards the second end 1074, with no steps or angles present on the inner surface 1075. The second inner surface 1075 of the cover 1070 and the outer surface 1037 of the funnel 1030 define the first fluid passage 1080 having an inlet 1082 and an outlet 1084. The inlet 1082 of the first fluid passage 1080 is in fluid communication with the first fluid inlet 1018 of the base 1012 and first fluid passage 1038 of the funnel 1030. Due to the contours of the second inner surface 1075 of the cover and outer surface 1037 of the funnel the first fluid passage 1080 has a divergent-convergent internal geometry. In other words, the cross sectional area of a portion of the first fluid passage 1080 intermediate the inlet 1082 and outlet 1084 is greater than the cross sectional area at either the inlet 1082 or outlet 1084. The cross sectional area of the first fluid passage 1080 progressively reduces following the intermediate portion. The total volume of the first fluid passage 1080 from inlet 1082 to outlet 1084 may be between 119000 cu. m. and 121500 cu. m.

FIG. 12A shows a detailed view of the respective outlets 1084,1094 of the first and second fluid passages 1080, 1090. Once the various components are correctly assembled, the outlet 1094 of the second fluid passage 1090 is defined between the second ends 1052, 1042 of the plug 1050 and funnel 1030. The outlet 1084 of the first fluid passage 1080 is defined between the second end 1042 of the funnel 1030 and the inner surface 1078 of the lip 1076.

The way and means in which a mist is generated by the apparatus will now be described with particular reference to FIGS. 11, 12A and 12B. Initially, supplies of first and second fluids are connected to the respective first and second fluid inlets 1018, 1020 of the atomizer 1000. The first fluid, also known as the working fluid, is a liquid fire fighting agent, preferably water. The liquid is preferably introduced at a mass flow rate of between 4 kg/min and 20 kg/min at the first fluid inlet 1018. The liquid passes through the first fluid passage 1080 which narrows considerably in the direction of its outlet 1084 to define a working nozzle. As a result of this narrow gap at the outlet 1084, the liquid ejects out of the outlet 1084 as a thin annulus of liquid, initially following a path represented in FIG. 12A by the dotted line 1200. The initial path of the liquid 1200 from the outlet 1084 of the first passage 1080 is substantially parallel to the inner surface 1078 of the lip 1076.

The second fluid, also known as the transport or carrier fluid, is preferably a gas such as compressed air, nitrogen or helium, for example. The gas is preferably introduced to the second fluid inlet 1020 at a pressure of between 4 bar and 18 bar for passage through the second fluid passage 1090 for ejection from the outlet 1094 to define a transport nozzle. Due to the reduction and subsequent increase in the cross sectional area of the second fluid passage 1090 between its inlet 1047, throat 1092 and outlet 1094, the gas entering the inlet 1047 is accelerated to a high, possibly even supersonic, velocity as it exits the outlet 1094. The gas may be discharged at a mass flow rate of between 2 kg/min and 6 kg/min.

The angle of the second fluid passage 1090 is such that the accelerated second fluid stream, whose initial trajectory is shown as dotted line 1220 in FIG. 12A, exits the outlet 1094 and interacts with the annulus of liquid issuing from the outlet 1084. The angle of incidence between the liquid and the gas streams 1200, 1220 is shown in FIG. 12A as angle $\alpha$.

With reference to FIGS. 12A and 12B, an equivalent angle of expansion for the second passage 1090 as it expands between the throat 1092 and the outlet 1094 may be calculated. In particular, FIG. 12B shows schematically how this equivalent angle of expansion for the second fluid passage can be calculated when the cross sectional areas of the throat and outlet, and the equivalent path distance between the throat and outlet are known. E1 is the radius of a circle having the same cross sectional area as the throat of the second fluid passage. E2 is the radius of a circle having the same cross sectional area as the outlet of the second fluid passage. The distance d is the equivalent path distance between the throat and the outlet. An angle $\beta$ is calculated by drawing a line through the top of E2 and E1 which intersects a continuation of the equivalent distance line d. This angle $\beta$ can either be measured from a scale drawing or else calculated from trigonometry using the radii E1, E2 and the distance d. The equivalent angle of expansion for the second fluid passage can then be calculated by multiplying the angle $\beta$ by a factor of two, where $\gamma=2\beta$.

For optimum performance of the apparatus, it has been found that the cross sectional area of the throat portion 1092 of the second fluid passage 1090 should preferably be between 20 mm$^2$ and 35 mm$^2$. The cross sectional area at the outlet 1094 of the second fluid passage may be between 1.1 and 28 times larger than that of the throat portion 1092, such that the area ratio between the throat 1092 and outlet 1094 of the second fluid passage 1090 may be between 10:11 and 1:28. The cross sectional area at the outlet 1094 of the second fluid passage may most preferably be between 1.4 and 5.5 times larger than that of the throat portion 1092, such that the area ratio between the throat 1092 and outlet 1094 of the second fluid passage 1090 is therefore most preferably between 5:7 and 2:11. This increase in cross sectional area between the throat portion 1092 and outlet 1094 creates an equivalent included angle of expansion for the second fluid passage 1090 of between 1 and 40 degrees, and an angle which is most preferably between 2 and 13 degrees. Furthermore, the cross sectional area of the second fluid passage outlet 1094 may be between 0.3 and 12 times larger than the cross sectional area of the first fluid passage outlet 1084, such that the area ratio between the first fluid outlet 1084 and second fluid outlet 1094 is therefore between 10:3 and 1:12. The cross sectional area of the second fluid passage outlet 1094 is most preferably between 1 and 6 times larger than the cross sectional area of the first fluid passage outlet 1084, such that the area ratio between the first fluid outlet 1084 and second fluid outlet 1094 is therefore most preferably between 1:1 and 1:6.

The stream of gas 1220 coming into contact with the stream of liquid 1200 causes shear stripping of droplets from the annulus of liquid 1200 due to Kelvin-Helmholtz and Raleigh-Taylor instabilities on the first fluid surface. These instabilities cause ligaments of the liquid to break off from the annulus and form a dispersed droplet flow regime of the liquid and gas. In other words, a dispersed phase of the first fluid droplets is dispersed in a continuous phase of the second fluid. As the droplets are torn from the liquid stream 1200 they are accelerated by the gas, causing further shear break-up. Where the gas exits the outlet 1094 at a supersonic velocity, a supersonic shockwave may be created distal of the apparatus which may be beneficial to the atomization mechanism. The shockwave is created as the gas transitions from supersonic to subsonic speed. The shockwave is created at the point of transition from supersonic to subsonic speed. In this instance, the first fluid is further atomized by the shockwave at the point of transition.

The gas creates a turbulent region 1240 as it moves away from the apparatus and induces low velocity currents capable of transporting the droplets of first fluid preferably through the surrounding space, preferably in a homogenous manner. This turbulent region 1240 is caused by rapid changes in the pressure and velocity of the gas generating numerous unsteady vortices and a swirling of the gas. The turbulent region 1240 applies acceleration and deceleration forces on the droplets of the liquid, leading to a further atomization of the droplets being carried by the second fluid. This atomization mechanism can be controlled by, amongst other things, controlling the momentum flux ratio between the first and second fluids.

The momentum flux ratio M is defined by the equation $$M \equiv \frac{(\rho_s \times U_s^2)}{(\rho_f \times U_f^2)}$$

where
ρ=Fluid density
U=Fluid velocity
s represents second fluid (gas)
f represents first fluid (liquid)

Thus, the momentum flux ratio between the liquid and gas can be controlled by varying the density or velocity of the fluids. The velocity can be varied by adjusting the feed pressure while the density can be varied by changing the temperature of the fluid.

Figure 14:
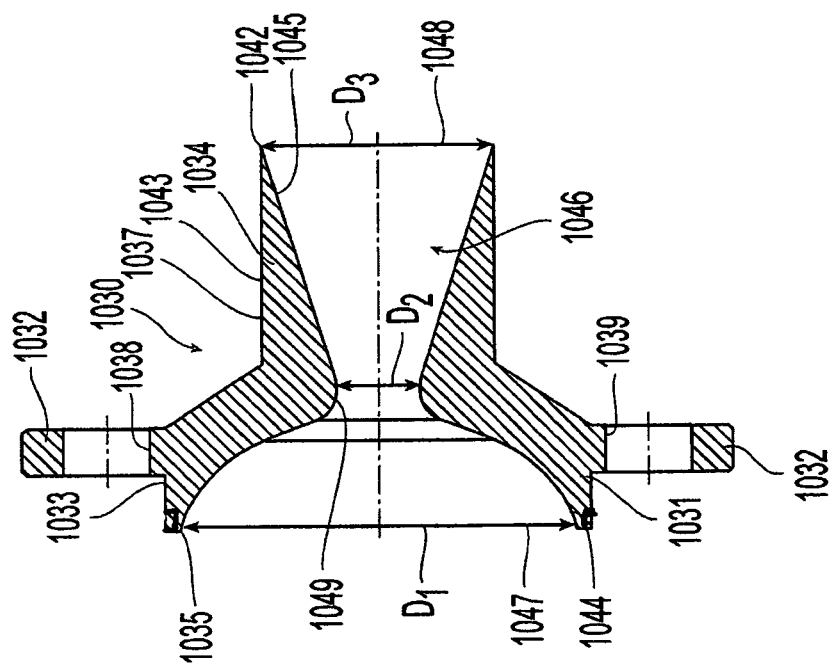
FIG. 14 is a cross-sectional view of the funnel of the atomizer of FIG. 11.

As most clearly shown in FIG. 12A, the liquid and gas streams 1200, 1220 issuing from their respective outlets 1084, 1094 are angled relative to one another at an angle of incidence α. The angle of incidence α is the angle between the initial trajectories of the streams 1200, 1220, shown as dotted lines in FIG. 12A. These initial trajectories are dictated by the inner wall 1043 of the first fluid passage 1080 and the outer wall 1045 of the second fluid passage 1090 at their respective outlets 1084, 1094. Thus, to obtain an angle of incidence in a desired range, the angle between these passage walls 1043, 1045 at the first and second fluid outlets 1084, 1094 should be in the same range. In the embodiment illustrated, both the inner first passage wall 1043 and outer second passage wall 1045 are defined by the funnel 1030, as best seen in FIG. 14. Referring again to FIG. 12A, the angle of incidence α causes the second fluid stream 122 to impinge on the annulus forming the first fluid stream 120. The angle of incidence α is less than 90 degrees, and preferably between 5 and 30 degrees. Most preferably, the angle of incidence α is between 10 and 20 degrees.

Figure 11:
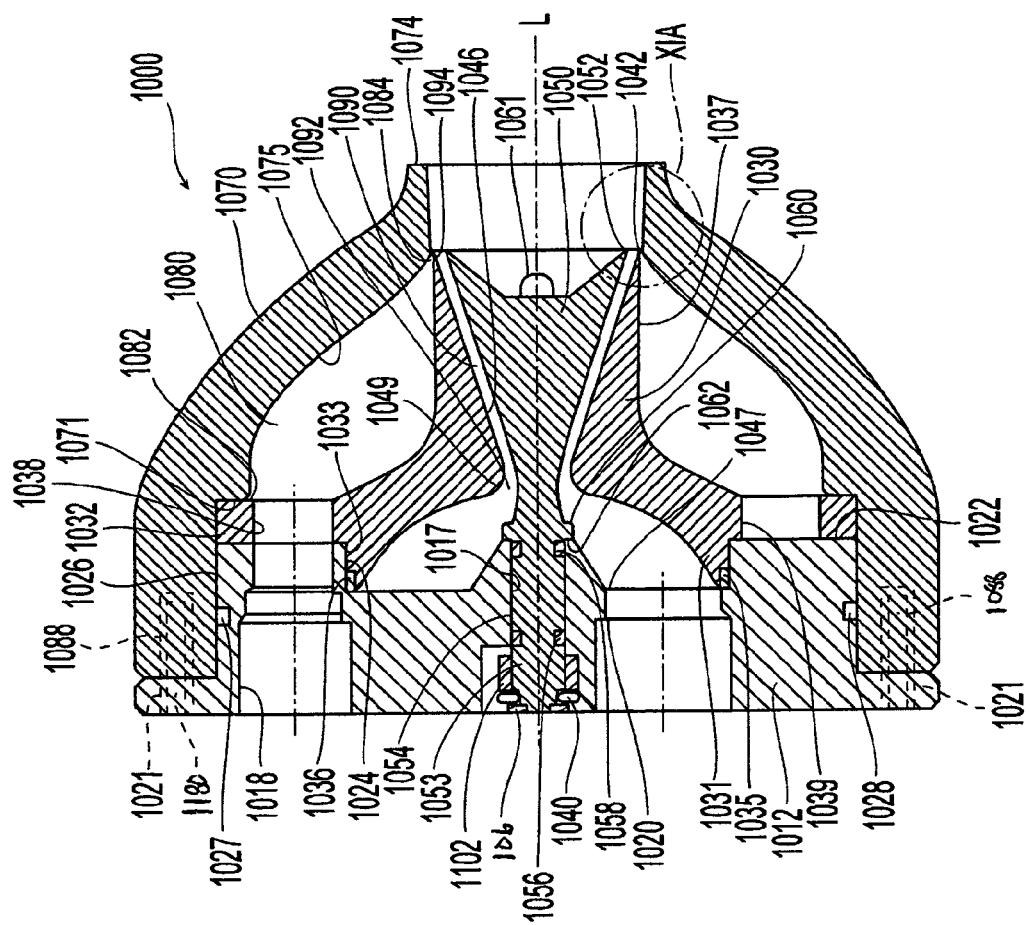
FIG. 11 is a cross-sectional view of one embodiment of an atomizer assembly.
Figure 17A:
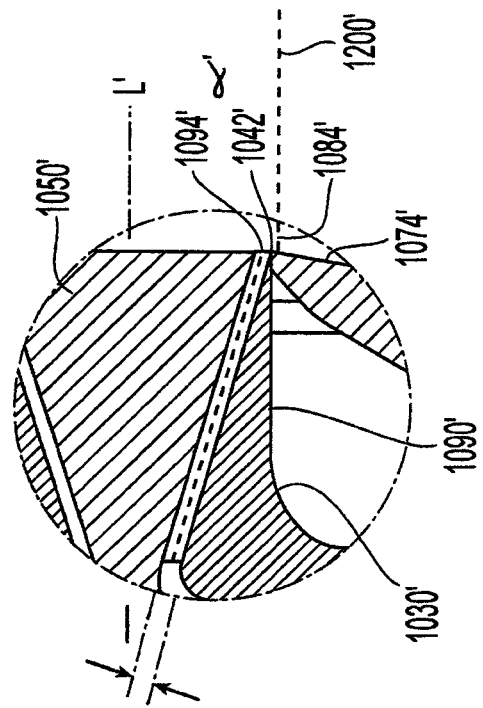
FIG. 17A is a detailed view of the atomizer assembly of FIG. 17.
Figure 17:
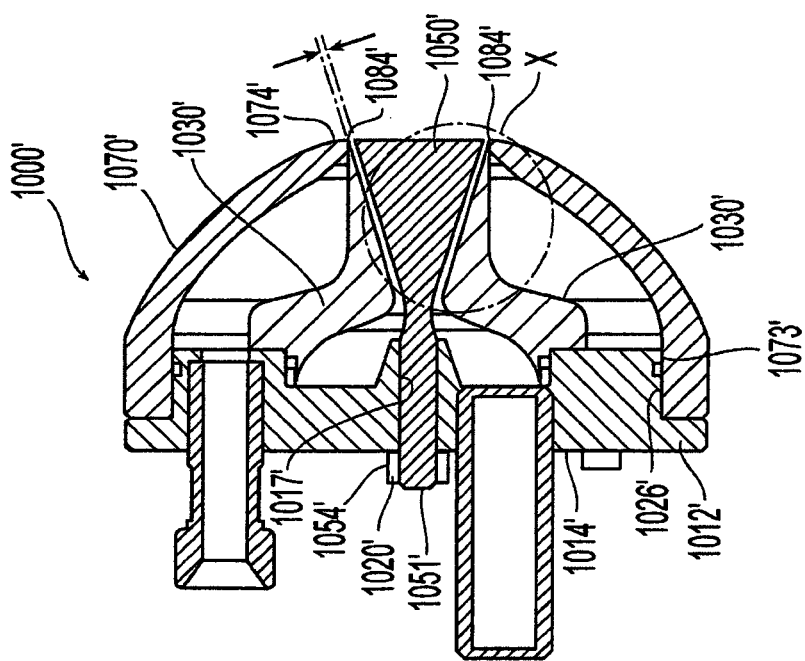
FIG. 17 is a cross-sectional view of an embodiment of another atomizer assembly.
Figure 18:
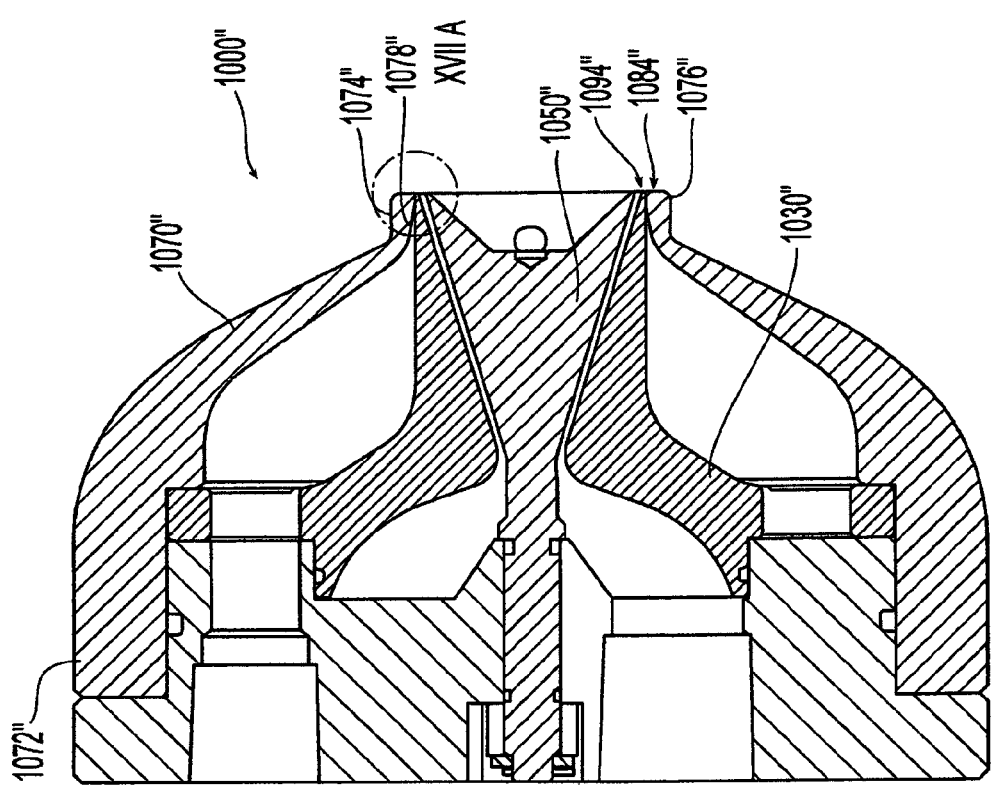
FIG. 18 is a cross-sectional view of an embodiment of another atomizer assembly.
Figure 19:
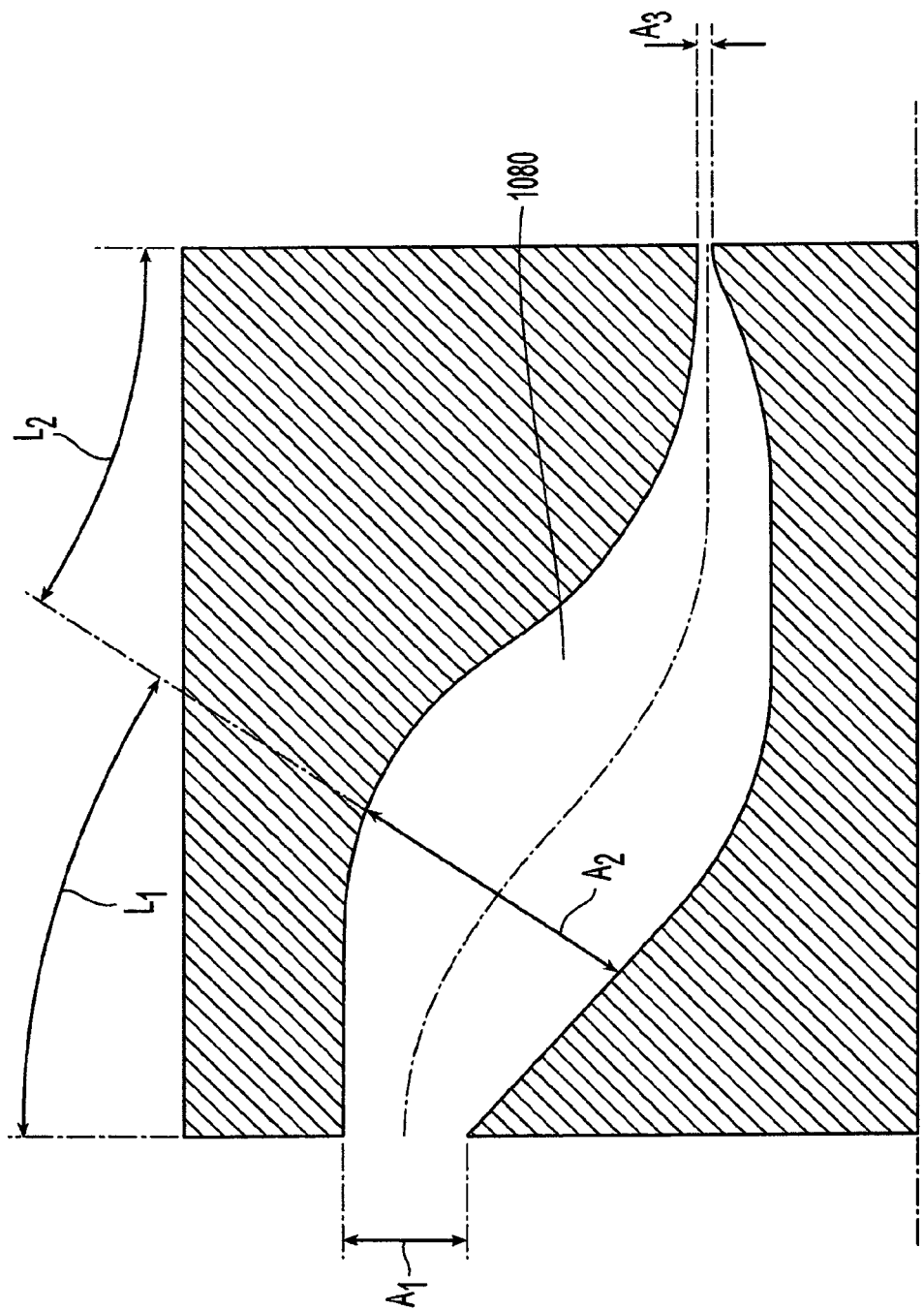
FIG. 19 is a cross-sectional view of a fluid passage in the atomizer of FIG. 11.
Figure 19A:
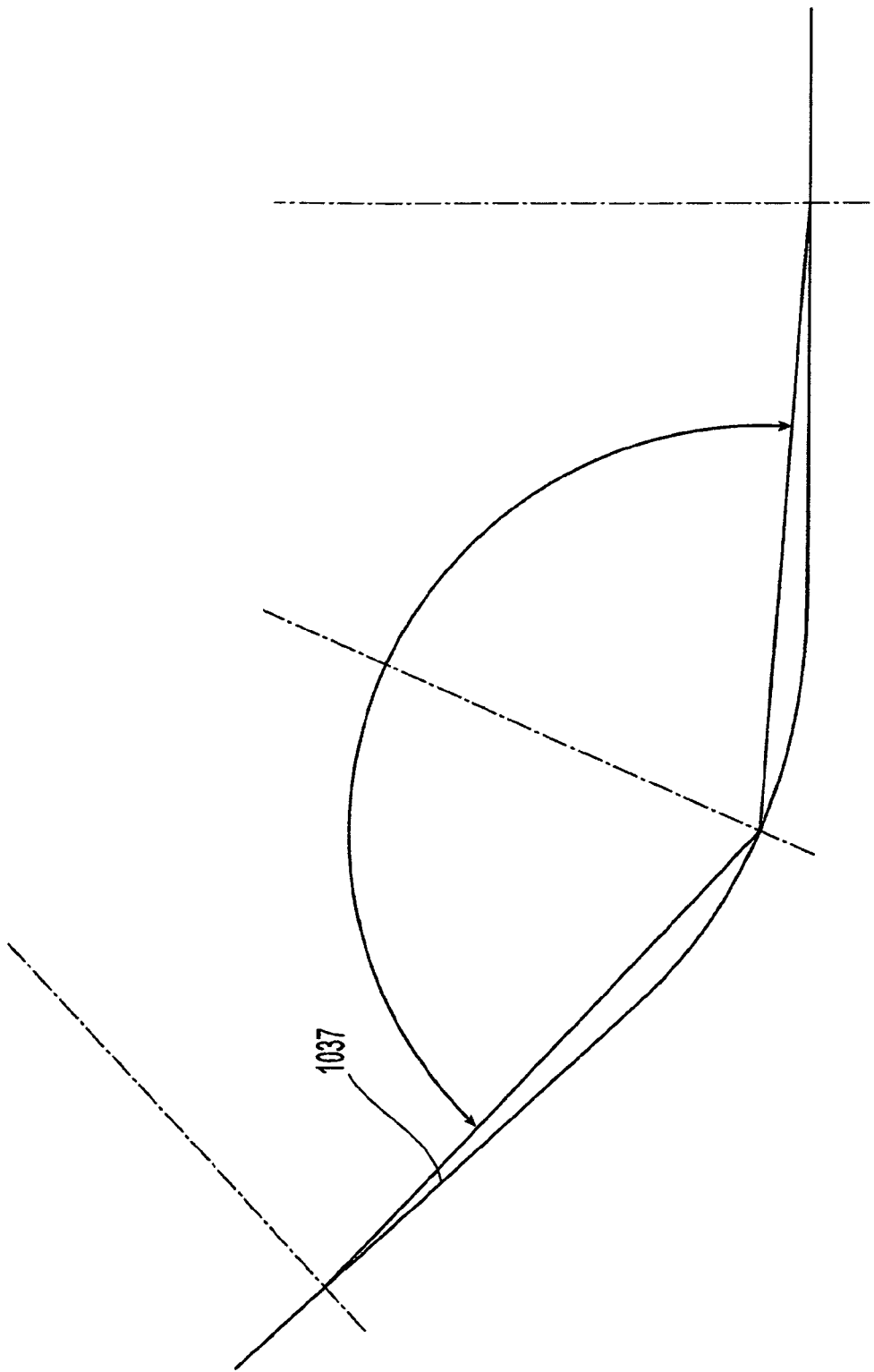
FIG. 19A is a detailed view of the fluid passage of FIG. 11.

The atomizers 1000, 1000' and 1000" of FIGS. 11, 17 and 18 provide means for atomizing a first fluid with a second fluid. In particular, each of the atomizers include first and second fluid passages 1080, 1090 each defining a fluid path and volume to discharge, engage and mix a stream of a liquid with a high velocity gas for atomization of the liquid stream for generation and distribution of a mist. However, alternative means can be provided to produce and engage a liquid stream and high velocity gas to atomize and disperse the liquid as a mist. In view of the atomizers described herein, known mist generating devices could be modified to discharge a liquid annulus from one fluid passage and accelerate and discharge an inert gas from another fluid passage to atomize the liquid annulus for generation and distribution of a liquid mist in an enclosed space to be protected, and thus provide a means for atomizing a first fluid with a second fluid.

Referring again to FIG. 11, the inner surface 1078 of the lip 1076 of cover 1070 ensures that larger droplets torn from the first fluid stream 1200 that could be projected away from the longitudinal axis L of the apparatus by the second fluid stream 1220 are prevented from doing so to provide for mixing of the liquid and the gas in the chamber of the lip 1076. Furthermore, droplets held against the inner surface 1078 of the lip 1076 are more easily atomized as they are subject to both the force of the second fluid and the friction forces from the inner surface 1078.

Figure 20:
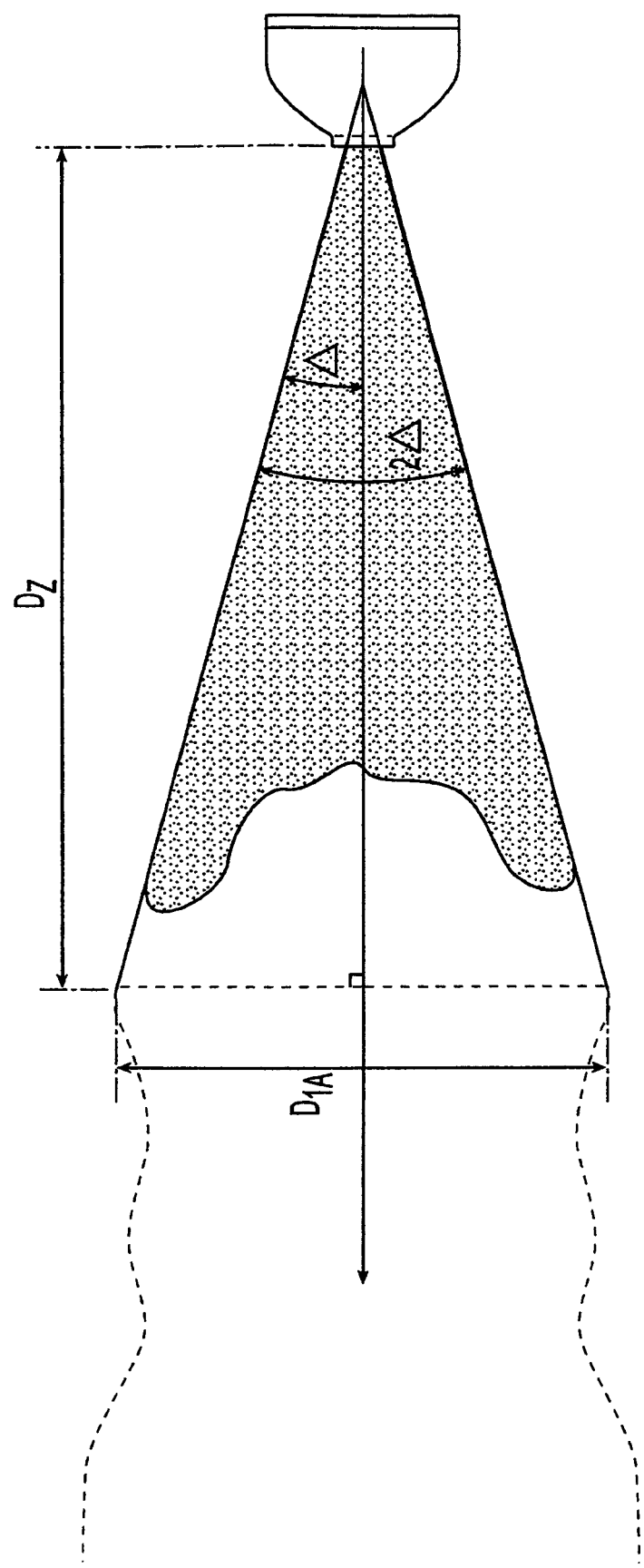
FIG. 20 is a schematic diagram of a spray pattern from the atomizer of FIG. 11.
Figure 22:
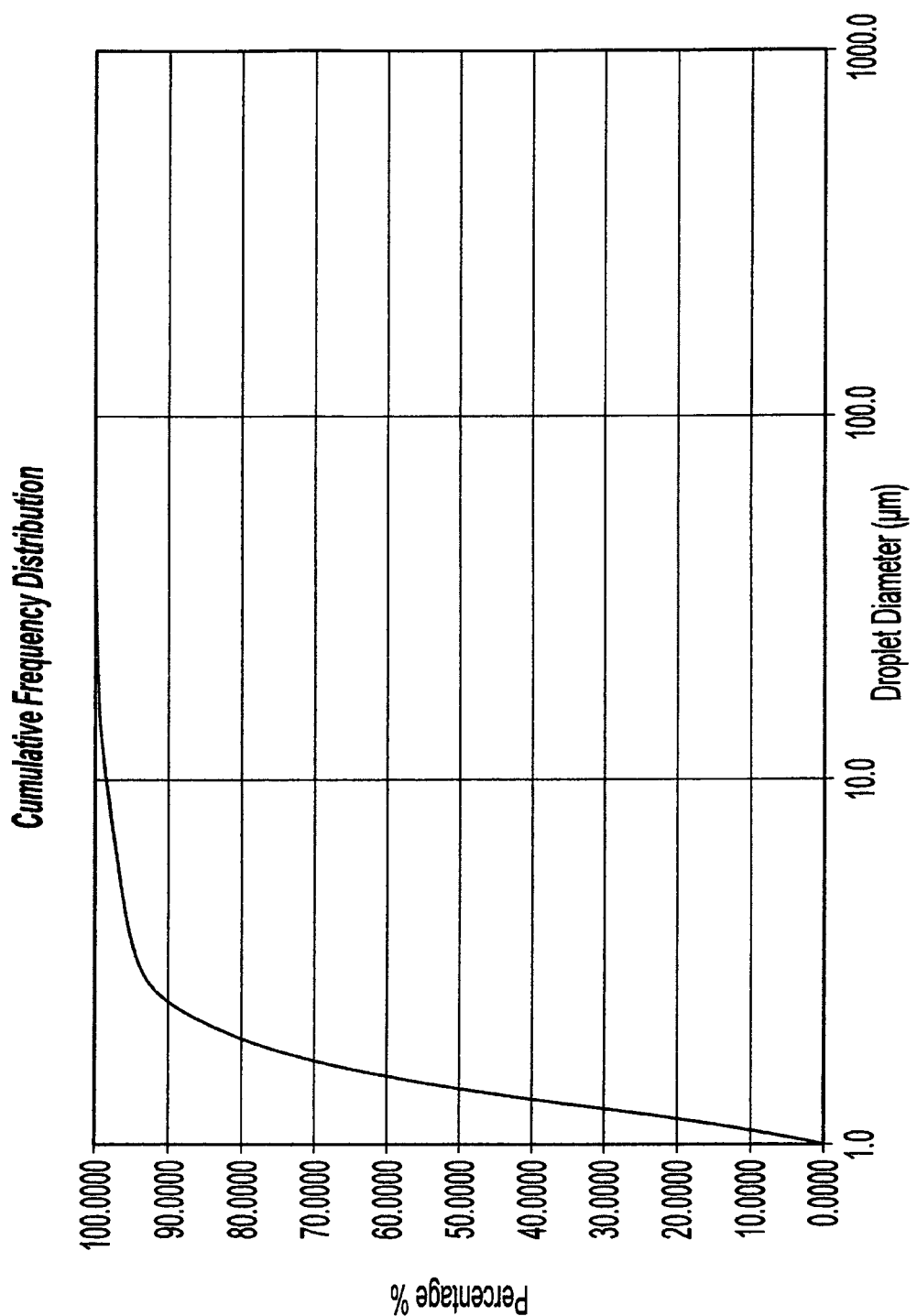
FIG. 22 is a plot showing the cumulative frequency distribution of droplet sizes in a spray pattern from the atomizer of FIG. 11.

The atomization mechanism of the present invention is capable of atomizing the liquid into a mist in which a large proportion, preferably greater than 80% of the droplets, range in size from about 1 micron to about 10 microns and more preferably ranging from about 1 micron to about 5 microns. Shown in FIG. 22, for purposes of illustration is a cumulative frequency size distribution of the droplets in the mist produced by a preferred atomizer. According to the plot, the mist includes a distribution of droplets in which more than 90% have a droplet size ranging between 1 to 10 microns in diameter. The discharging gas and annulus of liquid together preferably define a substantially conical mist spray pattern. Referring to FIG. 20, the mist spray pattern for a preferred atomizer is illustrated in a side cross-sectional view. The perimeter of the mist spray pattern define the cross-sectional area defines an included angle Δ of about 15° degrees (±2°) with the central axis of the atomizer, and therefore included angle of 2Δ about 30° degrees (±2°) between the perimeter of the spray pattern defining the conical shape of the mist.

It has been determined that the conical spray pattern is substantially fully developed at an axial distance DZ of about 1.1 m. (42 inches) from the discharge end of the atomizer and more preferably fully developed at an axial distance DZ of about 1.6 m. (64 inches) from the discharge end of the atomizer. By "substantially fully developed" it is understood that the conical spray pattern has maximized its radial distance from the central axis of the atomizer so as to find an end circle of the conical spray pattern having a diameter D1A of about 0.6 m. (24 inches) at the axial distance of about 1.1 m. (42 inches) from the atomizer, and more preferably having a diameter DIA of about 0.9 m. (36 inches) at the axial distance of about 1.6 m. (64 inches) from the atomizer.

For the atomizing device 1000 shown in FIG. 11, applicants supplied a flow of water at 11.3 lpm (3 gpm) with a supply of nitrogen gas at 6.9 bar (100 psi.) The resultant mist spray pattern was observed against a black background and photographed. Shape and included angles of the mist spray pattern is calculated based upon the scale relationship between the photograph and an actual dimensioned feature of the atomizer. For example, where the discharge end of the atomizer has a diameter of about 40 mm. (1.57 inches) and in the photograph has a diameter of about 5.9 mm. (0.232 inches) to define a photo scale factor of about 6.75.

Figure 13A:
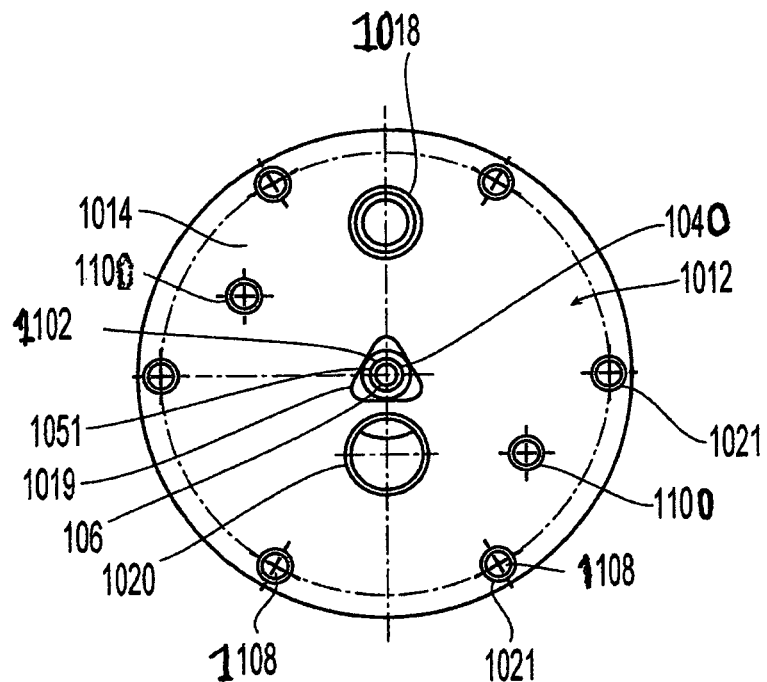
FIG. 13A is a plan end view of the base of FIG. 13.
Figure 13:
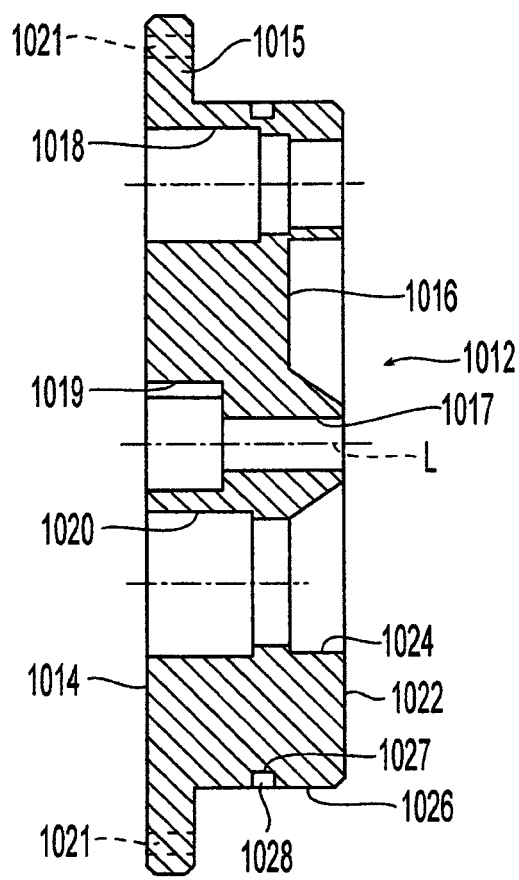
FIG. 13 is a cross-sectional view of the base of the atomizer of FIG. 11.

The components of the atomizer 1000 will be described in greater detail. Referring to FIG. 13 is a longitudinal section view through the base 1012. As noted above, the base 1012 is generally circular and has a rear face 1014, a front face 1016 and first and second fluid inlet passages 1018, 1020 adapted to receive the first and second fluids from their respective sources (not shown). Each of the fluid inlet passages 1018, 1020 is substantially parallel with the longitudinal axis L of the apparatus. Each fluid inlet passage 1018, 1020 has an internal thread adapted to receive the external thread of respective fluid supply pipes (not shown). Extending longitudinally through the centre of the base 1012 is the bore 1017. Referring to FIG. 13A, the bore 1017 has a generally triangular-shaped recess 1019 opening on the rear face 1014 of the base 1012. The base 1012 includes a radially extending flange portion 1015 and an axially projecting annular projection 1022 which projects forwards from the front face 1016. A plurality of circumferentially spaced apertures 1021 extend longitudinally through the flange portion 1015. The annular projection 1022 has an inner surface 1024 and an outer surface 1026. The outer surface 1026 contains a groove 1027 in which an O-ring seal 1028 is located.

FIG. 14 shows the funnel 1030 as a projecting member preferably formed as a single piece having a radially extending flange portion 1032 and an axially projecting body portion 1034. The body portion 1034 has an outer surface 1037. An annular lip portion 1031 extends rearwards from the flange portion 1032 and defines an outer surface 1033. The outer surface 1033 contains a groove 1035 in which an O-ring seal 1036 is located. The flange portion 1032 is annular and extends around the entire circumference of the projecting member 1030. Defined within the flange portion 1032 are a first fluid passage 1038 and an inspection port 1039.

As described above, the funnel 1030 has a first end 1044 and a second end 1042 and a bore 1046 extending longitudinally through the funnel 1030 from the first end 1044 to the second end 1042. The bore 1046 has the inlet 1047 at the first end 1044, the outlet 1048 at the second end 1042, and the throat portion 1049 intermediate the inlet 1047 and outlet 1048. The bore 1046 may have an axial length of between 52 mm and 55 mm. At the inlet 1047 the bore 1046 has a diameter D1 which may be between 53 mm and 59 mm. At the throat portion 1049 the diameter of the bore 1046 is D2 which may be between 7.5 mm and 13 mm, and at the outlet 1048 the diameter of the bore is D3 which may be between 30 mm and 34 mm. The diameter D1 at the inlet 1047 is greater than the diameter D2 or D3, whilst the diameter D2 at the throat portion 1049 is less than the diameters D1 and D3. As a result, the bore 1046 narrows from its widest point at the inlet 1047 to a narrow diameter at the throat portion 1049 before widening again until it reaches the outlet 1048.

Figure 15:
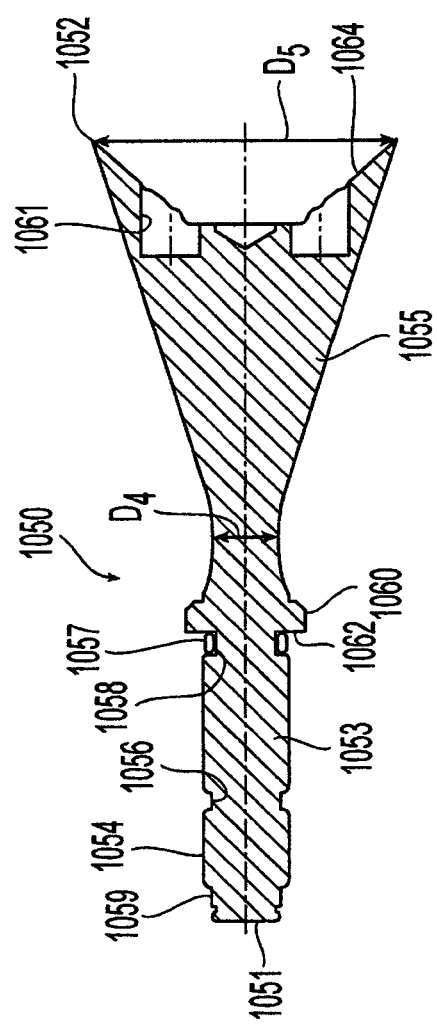
FIG. 15 is a cross-sectional view of the plug of the atomizer of FIG. 11.

FIG. 15 shows the plug 1050 forming a further part of the mist-generating apparatus. As described generally above, the plug 1050 is an elongate member having a first end 1051 and a second end 1052. The plug 1050 has a first generally cylindrical portion 1053 and a second conical portion 1055 extending from, and preferably integrally formed with, the cylindrical portion 1053. More preferably, part of the cylindrical portion 1053 adjacent the first end 1051 is provided with an external thread 1054. The conical portion 1055 is in the shape of an inverted cone, with the narrowest point of the cone adjacent the cylindrical portion 1053 and the widest point of the cone at the second end 1052 of the plug 1050. The conical portion 1055 has a smallest diameter D4 adjacent the cylindrical portion 1053 and a largest diameter D5 at the second end 1052 of the plug 1050. The cylindrical portion 1053 has first and second grooves 1056, 1058 longitudinally spaced from one another and extending around the circumference of the cylindrical portion 1053. The first groove 1056 is a thread relief groove co-operating with the external thread 1054. Also formed part way along the cylindrical portion 1053 is a radially projecting lip 1060, which defines an abutment surface 1062 facing towards the first end 1051 of the plug 1050. The second groove 1058 holds an O-ring seal 1057. A further groove 1059 is provided in the cylindrical portion 1053 of the plug 1050 adjacent the first end 1051.

The second end 1052 of the plug 1050, which is also the widest part of the conical portion 1055, has an end face which is concave. Thus, a dish-shaped cavity 1064 is formed in the second end face of the plug 1050. The end face of the second end 1052 also includes a pair of locating holes 1061.

Figure 16:
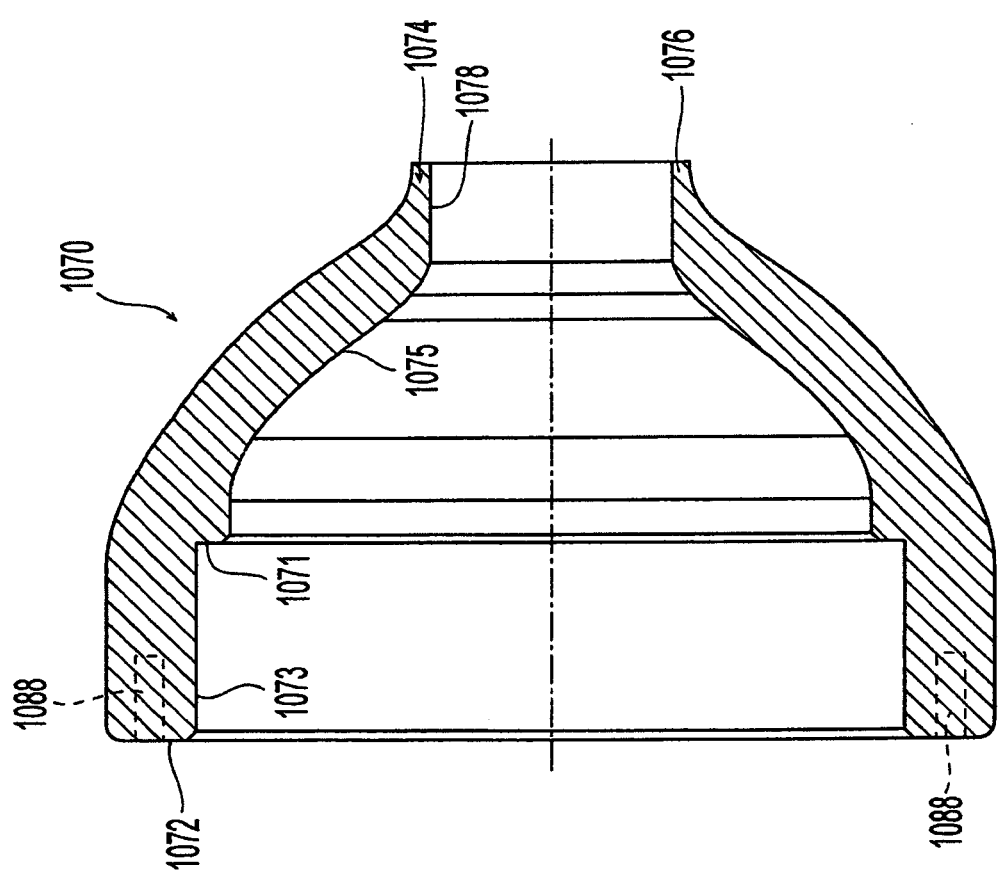
FIG. 16 is a cross-sectional view of the cover of the atomizer of FIG. 11.

FIG. 16 shows the cover 1070 forming part of the mist-generating apparatus. The cover 1070 is preferably generally dome-shaped, having a first end 1072 of larger diameter than a second end 1074. Projecting axially from the second end 1074 of the cover 1070 is an annular lip 1076. The lip 1076 has an internal surface 1078 which defines a bore of substantially constant diameter. In other words, the lip 1076 has internal walls which are substantially parallel when viewed in vertical cross-section, such as here in FIG. 16. The cover 1070 has a first section adjacent the first end 1072 which has a first inner surface 1073 of substantially constant diameter. Located in the first end 1072 of the cover 1070 at circumferentially spaced intervals are a plurality of axially extending threaded holes 1088. A second section of the cover 1070 extending between the first section and the lip 1076 has a second inner surface 1075. The portion of the second section adjoining the first section has a smaller diameter than that of the first section, such that a rearward facing abutment 1071 is defined between the first and second sections of the cover 1070. The diameter of the second section reduces in the direction of the second end 1074. In other words, the second inner surface 1075 tapers inwardly from the abutment 1071 until it reaches the internal surface 1078 of the lip 1076. Thus, the second inner surface 1075 has a smooth inwardly curving profile as it progresses towards the second end 1074, with no steps or angles present on the inner surface 1075.

Figure 11A:
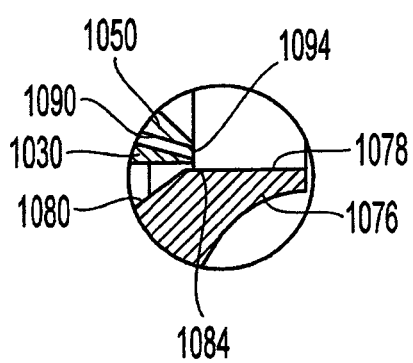
FIG. 11A is a detailed view of the atomizer assembly of FIG. 11.

The manner in which the mist-generating apparatus, generally designated 1000, is assembled will now be described with particular reference to FIGS. 11 and 11A. Firstly, each of the components shown in FIGS. 13-16 is formed from a suitable material, which is preferably stainless steel. In the first step of assembling the apparatus 1000, the funnel 1030 is axially inserted onto the base 1012 so that the base 1012 and funnel 1030 are concentric about the longitudinal axis L, with the outer surface 1033 of the funnel lip 1031 being guided by the inner surface 1024 of the annular projection 1022, until the rear face of the flange portion 1032 abuts the surface of the annular projection 1022. The O-ring seal 1036 located in the groove 1035 on the outer surface 1033 ensures a sealing fit between the two components. When the base 1012 and funnel 1030 are correctly positioned, the first fluid inlet passage 1018 of the base 1012 and first fluid passage 1038 of the funnel are aligned and capable of fluid communication with one another. Furthermore, the inlet 1047 of the funnel bore 1046 and the second fluid inlet passage 1020 of the base 1012 are now in fluid communication with one another as well. Once the base 1012 and funnel 1030 have been correctly oriented with respect to one another, a temporary locking ring (not shown) is secured over the flange portion 1032 of the funnel 1030 such that the base 1012 and funnel 1030 are locked together.

Once the base 1012 and funnel 1030 are temporarily locked together, the plug 1050 can be introduced, firstly via the bore 1046 of the funnel 1030 and then the bore 1017 of the base 1012. As best seen in FIG. 13A, a locking nut 1102 is inserted into the recess 1019. As the plug 1050 is inserted through the bores 1046,1017 it is rotated by a suitable tool (not shown) which locates in the locating holes 1061. As the plug 1050 is rotated the threaded surface 1054 of the plug 1050 marries with the internal thread of the locking nut 1102. The outer faces of the nut 1020 contact the inner surfaces of the triangular recess 1019 such that the recess 1019 prevents the nut 1020 from rotating as the first end 1051 and threaded surface 1054 of the plug 1050 are threaded through. The lip 1060 of the plug 1050 has a larger diameter than the bore 1017. Consequently, once the abutment surface 1062 of the lip 1060 comes into contact with the base 1012, the plug 1050 cannot be threaded any further through the nut 1020. At this point, a washer 1040 and circlip 106 are fitted to the first end 1051 of the plug 1050 so that the nut 1020 cannot work itself loose. The circlip 106 locates in the groove 1059 provided at the first end 1051 of the plug 1050. The O-ring seal 1057 located in the cylindrical portion 1053 of the plug 1050 ensures a sealing fit between the plug 1050 and the bore 1017.

As can be seen in FIG. 11, once the plug 1050 is axially and concentrically located in the bore 1017, the conical portion 1055 of the plug 1050 lies between the throat portion 1049 and outlet 1048 of the bore 1046 in the funnel 1030. Consequently, the inner surface of the bore 1046 and outer surface of the plug 1050 now define a second fluid passage 1090.

Once the plug 1050 has been fixed to the base 12, the inspection port 1039 can be used to measure the axial distance between the top surface of the annular projection 1022 and the remote second ends 1042, 1052 of the funnel 1030 and plug 1050. This ensures that the base 1012, funnel 1030 and plug 1050 are all correctly positioned relative to one another. At the same time, measuring instruments can be used to check the gap between the funnel 1030 and plug 1050 which forms the second fluid passage 1090.

Once the measurement and positioning checks have been completed, the temporary locking ring can be removed and replaced with the cover 1070. The cover 1070 is axially placed on the base 1012 such that the abutment 1071 contacts the flange portion 1032 of the funnel 1030, and the cover is then concentric with the other components and the axis L. This sandwiches the flange portion 1032 between the base 1012 and cover 1070, holding the base 1012 and funnel 1030 against one another. At the same time, the O-ring seal 1028 ensures a sealing fit between the base 1012 and cover 1070. The cover 1070 is aligned with the base 1012 so that the threaded apertures 1088 align with the apertures 1021 in the base 1012. A plurality of fixing screws 1180 are then tightened into the threaded apertures 1088 via the apertures 1021 in the base 1012. Once the screws 1180 are fully tightened the heads of the screws 1180 are at least flush with the rear face 1014. A number of blind mounting holes 1100 with internal threads are also provided on the rear face 1014 of the base 1012 for attaching the apparatus to a suitable mounting skid or the like.

As seen best in FIG. 11, once the cover 1070 is successfully fitted, the second inner surface 1075 of the cover 1070 and the outer surface 1037 of the funnel 1030 define a first fluid passage 1080 having an inlet 1082 and an outlet 1084. The inlet 1082 is in fluid communication with the first fluid inlet 1018 and first fluid passage 1038. Due to the contours of the second inner surface 1075 and outer surface 1037 the first fluid passage 1080 has a divergent-convergent internal geometry. In other words, the cross sectional area of a portion of the first fluid passage 1080 intermediate the inlet 1082 and outlet 1084 is greater than the cross sectional area at either the inlet 1082 or outlet 1084. The cross sectional area of the first fluid passage 1080 progressively reduces following the intermediate portion. The total volume of the first fluid passage 1080 from inlet 1082 to outlet 1084 is about 120,400 cu. mm., and may be more preferably between 119,000 cu. mm. and 121,500 cu. mm.

The ability of the atomizer 1000 to generate a mist, as described above, having the preferred droplet size distribution for the preferred water flow rates and low gas pressures is believed to be a function of the geometry of the first and second fluid passages 1080, 1090. The ability of the liquid to form the desired thin annulus is a function of the first fluid passage 1080. Shown in FIG. 19 is detailed cross-sectional view of the first fluid flow passage 1080. The profile of the passage 1080 can be defined by a curve that is a function of the three critical areas: (i) the inlet area A1 at the inlet area of the passage 1080; (ii) the outlet area A3 at the outlet area of the passage 1080; and (iii) the maximum intermediate area A3 between the inlet area A1 and the outlet area A3. Each of the critical areas A1, A2, A3 define a substantially circular area coaxially disposed along the central fluid path FP of the passage 1080. The areas A1, A2 and A3 are separated from one another along the path FP by a first fluid path distance L1 between areas A1 and A2 and a second fluid path distance L2 between areas A2 and A3.

Using the radii of the critical areas, A1, A2 and A3, the angular rate of change in radii from one area to the next adjacent can be determined by their trigonometric relationship. The radii increases from the inlet area A1 to the intermediate area A2. In the preferred embodiment, the equivalent area A2 is larger than A1 by a factor of between 1 to 50, is preferably between 1 to 5 and is more preferably about 1 to 1.5, so as to define a preferable angular change between the radii from A1 to A2 of about 83° degrees (82.7°). The radii increases from the outlet area A3 to the intermediate area A2. In the preferred embodiment, the equivalent area A2 is larger than A1 by a factor of between 50 to 400, preferably 100 to 300, and more preferably 270 to 280, so as to define an angular change between the radii from A3 to A1 of about 84° degrees (83.6°).

The profile of the passage 1080 is preferably smooth. Smoothness can be defined as the angular spacing between adjacent discrete segments which can approximate the surface profile. Referring to FIG. 19A, shown is a detailed view of the wall profile of the passage 1080 has been broken up into discrete segments and the angle of change between each segment is measured. The discrete segments are each about 1 percent of the fluid path FP length. In a surface profile is smooth, then there is a small angular change from one segment to the next having a maximum change of about 90°, preferably a maximum of 45°, even more preferably a max of 45°, and is yet even more preferably less than 30 degrees. In contrast, if there is a sudden step in the profile, then the angular change is greater. In the preferred embodiment of the atomizer, the segmented profile of the passage 1080 has a maximum angular change that is less than 30 degrees. More specifically, the surface of the passage 1080 defined by the inner surface of the cover has a maximum angular change between adjacent segments of about 27° Degrees. The surface of the passage 1080 defined by the outer surface of the funnel has a maximum angular change between adjacent segments of about 4.5° Degrees.

Returning again to FIG. 11, once the various components are correctly assembled, the outlet 1094 of the second fluid passage 1090 is defined between the second ends 1052, 1042 of the plug 1050 and funnel 1030. The outlet 1084 of the first fluid passage 1080 is defined between the second end 1042 of the funnel 1030 and the inner surface 1078 of the lip 1076.

An alternative embodiment of the atomizer is shown in FIGS. 18 and 18A. In the atomizer 1000", the components are the same as those of the atomizer 1000 shown in FIG. 11. However, in this alternative embodiment, the funnel 1030" and plug 1050" are dimensioned so that the funnel and plug occupy the bore of the annular lip 1074" at the second end 1074" of the cover 1070". The configuration of the atomizer 1000" effectively eliminate the protruding lip by locating the first and second fluid outlets 1084", 1094" adjacent the second end 1074" of the cover 70".

FIGS. 17 and 17A show views of another alternative embodiment of a mist-generating apparatus in accordance with the present invention. The alternative embodiment of the apparatus, generally designated 1000', shares a number of components with the previously described embodiment and atomizes the first fluid in the same manner as described above. However, the alternative embodiment does also have a number of differences from the first embodiment. Most noticeably, the second end 1074' of the cover 1070' does not have a protruding lip. The second end 1074' is therefore adjacent the first and second fluid outlets 1084', 1094'. The funnel 1030' of this alternative embodiment does not have a radially projecting flange portion which is sandwiched between the cover 1070' and the base 1012'. Instead, the funnel 1030' is secured directly to the base 1012' by a number of fixing screws (not shown). Additionally, instead of being secured together by screw fixings the cover 1070' has an internal thread on its inner surface 1073' which cooperates with an external thread on the outer surface 1026' of the base 1012'. The cover 1070' can therefore be threaded onto the base 1012', and turning the cover 1070' relative to the base 1012' will adjust the axial distance between the cover 1070' and both the base 1012' and the funnel 1030' directly secured to the base 1012'.

As seen best in FIG. 17A, the first fluid outlet 1084' has been adapted in several ways in the alternative embodiment. Firstly, the width of the gap between the second ends 1042', 1074' of the funnel 1030' and cover 1070' which forms the first fluid outlet 1084' has been increased. Increasing the gap widens the first fluid outlet 1084' and reduces the exit velocity of the first fluid for the same flow rate condition. Secondly, as the axial distance between the cover 1070' and the funnel 1030' can be adjusted in this embodiment, the angle of projection and exit velocity of the first fluid can also be adjusted. Adjusting the axial position of the cover 1070'relative to the base 1012' and funnel 1030' adjusts the relative axial positions of the second end 1074' of the cover 1070' and the second end 1042' of the funnel 1030', both of which define the first fluid outlet 1084'. The adjustment of these components therefore also adjusts the gap size of the first fluid outlet 1084' and initial path 1200' of the first fluid stream as it exits through the first fluid outlet 1084'. As a result, the more the cover 1070' is screwed onto the base 1012' the more the initial path of the first fluid stream 1200' issuing from the outlet 1084' will diverge from the longitudinal axis L' of the apparatus 1000'. In the first embodiment, the angle of projection was substantially parallel with the longitudinal axis of the apparatus. The variation in the angle of projection also reduces the angle of incidence α' between the first and second fluid streams 1200',1220' issuing from their respective outlets 1084', 1094'.

The plug 1050' in the alternative embodiment has a longer threaded surface 1054' and no lip portion limiting its axial position relative to the base 1012'. The bore 1017' in the base 1012' has an internal thread which engages the threaded surface 1054' of the plug 1050'. As a result, the axial position of the plug 1050' relative to the base 1012' and the other main components can be adjusted depending upon the amount that the plug 1050' is screwed into the base 1012'. This also allows the width of the second fluid passage 1090' and outlet 1094' to be adjusted, as the position of the plug 50' can be adjusted relative to the funnel 30'. Consequently, the adjustment of the plug 1050' also adjusts the area ratio between the throat and outlet of the second fluid passage, as well as the equivalent angle of expansion of the second fluid passage. Once the plug 1050' has been positioned such that the area ratio between the first and second outlets and the equivalent angle of expansion are within the ranges set forth above, a lock nut 1020' is fitted over the first end 1051' of the plug 1050' protruding from the rear face 1014' of the base 1012'.

The present invention provides a mist generating apparatus which has a single supply channel for each of the first and second fluids. The supply channels are substantially parallel with the longitudinal axis of the apparatus, thereby reducing the supply pressures needed to supply the fluids. Having single supply channels for each fluid which are substantially parallel to the longitudinal axis of the apparatus allows the apparatus and supply lines to be more easily manufactured and installed on a mounting skid or the like, in comparison to mist generators which have one or more supply channels which enter the apparatus perpendicular to the longitudinal axis.

The geometry of the fluid passages and their respective outlets also provides the present invention with improved performance compared with existing mist generators in terms of efficiency (the amount of second fluid used to atomize the first fluid) and the degree of atomization of the first fluid. Specifically, the area ratio between the first and second fluid outlets, and the angle of incidence between the two streams of the fluid exiting the outlets improve atomization performance in the present invention. By providing an area ratio between the respective outlets as detailed above, the present invention provides a thin film sheet of first fluid which can be atomized more efficiently by the second fluid. The smaller exit area of the first fluid outlet also increases the exit velocity of the first fluid, which in itself can lead to a degree of atomization of the first fluid as it exits the apparatus. Providing an angle of incidence between the two streams which falls within the ranges detailed above provides improved atomization of the first fluid (in terms of droplet size and droplet distribution) whilst reducing the risk of the atomized first fluid droplets coalescing together again. The greater the angle of incidence between the streams, the greater the initial momentum transfer from the second fluid to the first fluid. However, a large angle of incidence also can lead to the first fluid film sheet converging when it comes into contact with the second fluid stream, increasing the risk that some of the atomized first fluid droplets will coalesce back together.

Using the second fluid stream to create a turbulent region outside the apparatus ensures further atomization of the first fluid, again improving the atomization performance of the present invention. Thus, the present invention provides a mist-generating apparatus which (i) generates a mist with the desired water droplet size, and (ii) generates turbulence in the protection space for substantially homogenous distribution of the water droplets throughout the volume of the surrounding space.

The method in which the apparatus is assembled also has benefits. The base, funnel, plug and cover are all assembled concentrically in such a way that the gaps defining the fluid passages and outlets between the components are consistent along the length and around the circumference of the apparatus. Furthermore, as each of the funnel, plug and cover are attached or mounted to the base plate, the components have a common reference point. This ensures that tolerance errors are minimized instead of being multiplied, as is often the case in prior art assemblies where the components are assembled together without a common reference.

In the embodiment having the cover member with an axially projecting lip, the lip prevents damage to the funnel and plug if the apparatus is dropped. The relative positions of these components, and hence the geometry of the first and second passages, is therefore protected. Additionally, the inner surface of the lip ensures that the apparatus has directionality, i.e. the atomized droplets can be directed towards a chosen location. Although as discussed above, such directionality is not necessary for the purpose of effective fluid mist fire protection.

Furthermore, droplets held against the inner surface of the lip are more easily atomized as they are subject to both the force of the second fluid and the friction forces from the inner surface. However, it should be understood that this first embodiment may alternatively have a lip which projects a relatively short distance, e.g. a few millimeters, or the lip may be omitted from the first embodiment. In these instances, the atomizing process described above will take place substantially outside of the mist-generating apparatus.

In the embodiment in which the cover member has no projecting lip, there is no radial constriction of the fluid streams. Therefore the streams are allowed to expand radially away from the longitudinal axis L of the apparatus at an earlier stage than they would if there was a lip present. This creates a greater degree of turbulence in the second fluid, which can enhance the atomization of the first fluid. Additionally, the resulting mist plume has a wider spread, which can be beneficial in a situation where the apparatus is to fill a particular volume with the mist as opposed to directing the plume towards a specific location.

One or more of the fixing screws used in the assembly of the apparatus may be replaced with an alternative mechanical fixture where appropriate. Suitable examples include fixing bolts, clamps, or a combination thereof. One or more of the mechanical fixtures may be a tamper proof or tamper evident fixture in order to either prevent or highlight disassembly of the apparatus following installation.

Instead of using a threaded arrangement as in the alternative embodiment, the adjustment of the axial position of the cover relative to the base may alternatively be achieved by inserting shims between the two components and then tightening the two components together using mechanical fixtures in the same manner as that of the first embodiment.

It should be recognized that the adapted features of the second illustrated embodiment are not limited to being used in combination. These features may therefore be incorporated individually in the first embodiment if desired. For example, an embodiment of the apparatus having no lip present need not also be provided with the adjustment arrangement for the cover member as well.

Whilst it is preferred that the apparatus is formed in the manner described from a base, funnel, plug and cover member, it should be recognized that the apparatus of the present invention is not limited to the formation of the various fluid channels and passages using these specific components. The desired fluid channels and passages may be created within the apparatus in an alternative manner to that described. For example, the channels and passages may be formed by drilling the apparatus, or else by casting the apparatus with the channels and passages formed therein.

Although the apparatus is preferably manufactured from stainless steel, alternative materials sharing the same properties may also be used instead. The primary requirements of the material are resistance to corrosion, chemicals and wear. It is also preferable that the material is easily machined or formed, and relatively inexpensive. Possible alternative materials include metals such as aluminum and brass, and metal alloys such as tungsten. Plastics or ceramic materials having the aforementioned properties may also be used.

Again, whilst the preferred first fluid has been described as water, the present invention is not limited to this specific first fluid. For example, the first fluid could be a liquid fire retardant instead. Similarly, whilst the second fluid is preferably a gas, it is not to be considered as limited to the examples of gas given in the foregoing disclosure. Other compressible fluids having similar properties to the gases disclosed may also be used without affecting the manner of operation of the present invention. The second fluid should preferably be easily obtainable, relatively inexpensive and non-corrosive. It may also be beneficial to use a second fluid which has the additional benefits of being generated on site (e.g. via a compressor) and/or has inerting benefits when used in fire suppression.

The inventors have provided methods, systems and devices for liquid mist-type fire protection that provides improved performance over previously known mist systems and technology. In particular, the preferred methods, systems and devices provide for liquid mist fire protection independent of the discharge device or atomizer location relative to any one of the floor space geometry and/or the hazard or fire location. In addition, the preferred system and methods provide for equal performance independent of the number of atomizers utilized provided that the total volume being discharged for the various system configurations is substantially equal. Finally, the preferred systems have demonstrated performance over known mist systems by (i) requiring less water and pressure consumption; and (ii) reducing the time to extinguishment over previously known mist systems.

While the present invention has been disclosed with reference to certain preferred embodiments, numerous modifications, alterations, and changes to the described embodiments are possible without departing from the sphere and scope of the present invention, as described herein.

The invention claimed is:

1. An atomizer for fire protection using a first fluid and a second fluid, the atomizer comprising:

a base, a cover coupled to the base and an internal fluid defining assembly disposed along a longitudinal axis between the base and the cover, the base at a proximal end of the atomizer including a first inlet for receipt of the first fluid and a second inlet for receipt of the second fluid, and the cover defining an outlet at a distal end of the atomizer for discharging the first and second fluid, the fluid defining assembly keeping the first and second fluids isolated from one another from the proximal to the distal end of the atomizer, the assembly including an outer funnel having an inner surface and an outer surface, the outer surface of the outer funnel defining a first fluid flow passageway in communication with the first inlet, the first fluid passage having a divergent-convergent internal geometry and the outer surface defining a continuous curved profile along the longitudinal axis that converges to a first fluid outlet, the first fluid passage the inner surface of the outer funnel defining a second passageway in communication with the second inlet, the assembly including an inner plug member disposed within the passageway and having an outer surface spaced from the inner surface of the outer funnel to define at least a portion of a second fluid flow passageway therebetween extending axially to the outlet, the second fluid flow passageway diverging in the proximal to distal direction to define a discharge orifice for the second fluid in communication with the outlet.

2. The atomizer of claim 1, Wherein the space between the outer surface of the inner plug member and the inner surface of the outer funnel is constant along its length.

3. The atomizer of claim 1, wherein the second fluid flow passageway is frustoconical having a proximal end and a distal end.

4. A mist generating apparatus having a longitudinal axis, the apparatus comprising:
   a first fluid passage having a first fluid inlet and a first fluid outlet;
   the first fluid passage having a divergent-convergent internal geometry and an outer surface defining a continuous curved profile along the longitudinal axis that converges to the first fluid outlet; and
   a second fluid passage having a second fluid inlet and a second fluid outlet;
   wherein the first fluid passage surrounds the second fluid passage, and the first and second fluid outlets are oriented relative to one another such that they have an angle of incidence between 5 and 30 degrees; and
   the second fluid passage having a throat portion located between the second fluid inlet and the second fluid outlet, the throat portion having a smaller cross sectional area than that of either the second fluid inlet or second fluid outlet.

5. The apparatus of claim 4, wherein the area ratio between the throat portion and the second fluid outlet is between 2:3 and 1:4.

6. The apparatus of claim 4, wherein the first fluid passage is located radially outward from the second fluid passage.

7. The apparatus of claim 6, wherein the first and second fluid passages are coaxial with the longitudinal axis of the apparatus.

8. The apparatus of claim 4, wherein the first fluid passage further comprises an intermediate portion located between the first fluid inlet and the first fluid outlet, the intermediate portion having a cross sectional area which is larger than that of either the first fluid inlet or the first fluid outlet.

9. The apparatus of claim 4, further comprising:
   a first fluid supply channel having a first end adapted to be connected to a supply of a first fluid and a second end connected to the first fluid inlet and
   a second fluid supply channel having a first end adapted to be connected to a supply of a second fluid and a second end connected to the second fluid inlet;
   wherein the first and second supply channels are substantially parallel to the longitudinal axis of the apparatus.

10. The apparatus of claim 9, further comprising a base member that contains the first and second fluid supply channels.

11. The apparatus of claim 10, further comprising a funnel member and an elongate plug member, wherein the funnel member has a bore and is adapted to coaxially locate upon the base member such that the bore communicates with the second fluid supply channel, and wherein the plug member is adapted to be attached to the base member such that a portion of the plug lies within the bore and the second fluid passage is defined between the funnel and the plug.

12. The apparatus of claim 11, further comprising a cover member which encloses the base member, the funnel member and the plug member such that the first fluid passage is defined between an outer surface of the funnel and an inner surface of the cover member.

13. The apparatus of claim 12, wherein the cover member has a first end adapted to coaxially locate upon the base member and be attached thereto, and a second end having an outlet adapted to communicate with the first and second fluid outlets.

14. The apparatus of claim 13, wherein the second end of the cover includes an axially projecting lip portion, the lip portion defining an aperture in communication with the first and second fluid outlets.

15. The apparatus of claim 12, wherein the plug member has a first end which attaches to the base member and a second end which defines the second fluid passage, wherein the second end has an end face which is concave.

16. The apparatus of claim 12, wherein the funnel member includes a radially projecting flange portion, wherein the flange portion is sandwiched between the base member and the cover member to maintain the axial position of the funnel member relative to the base member.

17. The apparatus of claim 12, wherein the apparatus is adapted such that the axial position of the cover member may be adjusted relative to the base.

18. The apparatus of claim 11, wherein the plug member may be threaded onto the base such that the axial position of the plug member may be adjusted relative to the base and the funnel.

19. A mist generating apparatus having a longitudinal axis, the apparatus comprising:
   a first fluid passage having a first fluid inlet and a first fluid outlet;
   the first fluid passage having a divergent-convergent internal geometry and an outer surface defining a continuous curved profile along, the longitudinal axis that converges to the first fluid outlet, and
   a second fluid passage having a second fluid inlet and a second fluid outlet;
   wherein the first fluid passage surrounds the second fluid passage, and the first and second fluid outlets are oriented relative to one another such that they have an angle of incidence of less than 90 degrees; and
   the second fluid passage includes a throat portion located between the second fluid inlet and the second fluid outlet, the throat portion having a smaller cross sectional area than that of either the second fluid inlet or second fluid outlet such that the area ratio between the throat portion and the second fluid outlet is between 2:3 and 1:4.

20. The apparatus of claim 19, wherein the first fluid passage is located radially outward from the second fluid passage.

21. The apparatus of claim 20, wherein the first and second fluid passages are coaxial with the longitudinal axis of the apparatus.

22. The apparatus of claim 19, wherein the first fluid passage includes an intermediate portion located between the first fluid inlet and the first fluid outlet, the intermediate portion having a cross sectional area which is larger than that of either the first fluid inlet or the first fluid outlet.

23. The apparatus of claim 19, further comprising:
   a first fluid supply channel having a first end adapted to be connected to a supply of a first fluid and a second end connected to the first fluid inlet; and
   a second fluid supply channel having a first end adapted to be connected to a supply of a second fluid and a second end connected to the second fluid inlet;

wherein the first and second supply channels are substantially parallel to the longitudinal axis of the apparatus.

24. The apparatus of claim 23, further comprising a base member that contains the first and second fluid supply channels.

25. The apparatus of claim 24, further comprising a funnel member and an elongate plug member, wherein the funnel member has a bore and is adapted to coaxially locate upon the base member such that the bore communicates with the second fluid supply channel, and wherein the plug member is adapted to be attached to the base member such that a portion of the plug member lies within the bore and the second fluid passage is defined between the funnel member and the plug member.

26. The apparatus of claim 25, further comprising a cover member which encloses the base member, the funnel member and the plug member such that the first fluid passage is defined between an outer surface of the funnel member and an inner surface of the cover member.

27. The apparatus of claim 26, wherein the cover member has a first end adapted to coaxially locate upon the base member and be attached thereto, and a second end having an outlet adapted to communicate with the first and second fluid outlets.

28. The apparatus of claim 27, wherein the second end of the cover member includes an axially projecting lip portion, the lip portion defining an aperture in communication with the first and second fluid outlets.

29. The apparatus of claim 25, wherein the plug member has a first end which attaches to the base member and a second end which defines the second fluid passage, wherein the second end has an end face which is concave.

30. The apparatus of claim 26, wherein the funnel member includes a radially projecting flange portion, wherein the flange portion is sandwiched between the base member and the cover member to maintain the axial position of the funnel member relative to the base member.

31. The apparatus of claim 26, wherein the apparatus is adapted such that the axial position of the cover member may be adjusted relative to the base member.

32. The apparatus of claim 25, wherein the plug member may be threaded onto the base member such that the axial position of the plug member may be adjusted relative to the base member and the funnel member.

33. A mist generating device comprising: a first fluid passage having a first fluid inlet and a first fluid outlet disposed about a longitudinal axis of the device;
the first fluid passage having a divergent-convergent internal geometry and an outer surface defining a continuous curved profile along the longitudinal axis that converges to the first fluid outlet, and a second fluid passage having a second fluid inlet and a second fluid outlet through which a second fluid passes, the second fluid passage disposed about the longitudinal axis concentric with the first fluid passage, the second fluid passage defining an equivalent angle of expansion of between 1 and 40 degrees; wherein the second fluid passage includes a throat portion located between the second fluid inlet and the second fluid outlet, the throat portion having a smaller cross sectional area than that of either the second fluid inlet or second fluid outlet such that the area ratio between the throat portion and the second fluid outlet is between 5:7 and 2:11; and wherein the ratio of the cross sectional area of the first fluid outlet to the second fluid outlet is between 10:3 and 1:12.

34. The device of claim 33, wherein the cross sectional area of the second fluid outlet is between 4 and 7 times greater than that of the first fluid outlet.

35. The device of claim 33, wherein the first fluid passage surrounds the second fluid passage, and the first and second fluid outlets are oriented relative to one another such that they have an angle of incidence of less than 90 degrees.

36. The device of claim 35, wherein the first and second fluid outlets are oriented relative to one another such that they have an angle of incidence of between 5 and 30 degrees.

37. The device of claim 33, wherein the first fluid passage is located radially outward from the second fluid passage.

38. The device of claim 33, wherein the first fluid passage includes an intermediate portion located between the first fluid inlet and the first fluid outlet, the intermediate portion having a cross sectional area which is larger than that of either the first fluid inlet or the first fluid outlet.

39. The device of claim 38, wherein the intermediate portion of the first fluid passage has a cross sectional area which is between 50 and 400 times greater than that of the first fluid outlet.

40. The device of claim 33, wherein the first fluid passage defines a smooth curving profile that converges toward the longitudinal axis such that a flow path decreases in a direction from the first fluid inlet to the first fluid outlet.

41. The device of claim 33, wherein the first fluid passage defines a total volume of between 119,000 cu. mm. (7.2 cu. in.) and 121,500 cu. mm. (7.4 cu. in.) and the second fluid passage defines a total volume of between 24,300 cu. mm. (1.5 cu. in.) and 25,500 cu. mm. (1.5 cu. in.).

42. The device of claim 33, further comprising: a first fluid supply channel having a first end adapted to be connected to a supply of a first fluid and a second end connected to the first fluid inlet; and second fluid and a second end connected to the second fluid inlet; wherein the first and second supply channels are substantially parallel to the longitudinal axis of the device.

43. The device of claim 33 further comprising a chamber in communication with the first and second fluid outlets for mixture of the liquid and gas discharge so as to form the mist.

44. The device of claim 33, wherein the cross sectional area of the throat portion of the second passage is between 20 cu. mm. (0.0012 cu, in.) and 35 cu. mm. (0.0021 cu. in.).

* * * * *